(12) United States Patent
Mengiste et al.

(10) Patent No.: US 11,505,804 B2
(45) Date of Patent: Nov. 22, 2022

(54) IMMUNE RECEPTOR CONFERRING BROAD SPECTRUM FUNGAL RESISTANCE IN SORGHUM

(71) Applicant: Purdue Research Foundation, West Lafayette, IN (US)

(72) Inventors: Tesfaye D Mengiste, West Lafayette, IN (US); Fuyou Fu, Saskatoon (CA); Sanghun Lee, West Lafayette, IN (US); Gebisa Ejeta, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/766,218

(22) PCT Filed: Nov. 21, 2018

(86) PCT No.: PCT/US2018/062172
§ 371 (c)(1),
(2) Date: May 21, 2020

(87) PCT Pub. No.: WO2019/104113
PCT Pub. Date: May 31, 2019

(65) Prior Publication Data
US 2021/0163978 A1 Jun. 3, 2021

Related U.S. Application Data

(60) Provisional application No. 62/589,295, filed on Nov. 21, 2017.

(51) Int. Cl.
*C12N 15/82* (2006.01)
*C12Q 1/6895* (2018.01)

(52) U.S. Cl.
CPC ....... *C12N 15/8282* (2013.01); *C12Q 1/6895* (2013.01); *C12Q 2600/13* (2013.01); *C12Q 2600/156* (2013.01)

(58) Field of Classification Search
CPC .................................................. C12N 15/8282
USPC .......................................................... 800/279
See application file for complete search history.

(56) References Cited

U.S. PATENT DOCUMENTS

| | | | |
|---|---|---|---|
| 7,365,185 B2 * | 4/2008 | Boukharov | C12N 15/8216 536/24.1 |
| 7,825,297 B2 | 11/2010 | Shah et al. | |
| 9,051,581 B2 | 6/2015 | Fang et al. | |
| 9,222,104 B2 | 12/2015 | Schweizer et al. | |
| 2010/0011467 A1 * | 1/2010 | Douchkov | C12N 15/8282 800/279 |

FOREIGN PATENT DOCUMENTS

| | | |
|---|---|---|
| WO | 2003044201 A1 | 5/2003 |
| WO | 2012023099 A1 | 2/2012 |

OTHER PUBLICATIONS

International Searching Authority, International Search Report, PCT Application Serial No. PCT/US2018/062172, dated Feb. 15, 2019.
International Searching Authority, Written Opinion of the International Searching Authority, PCT Application Serial No. PCT/US2018/062172, dated Feb. 15, 2019.

* cited by examiner

*Primary Examiner* — Li Zheng
(74) *Attorney, Agent, or Firm* — Reichel Stohry Dean LLP; Natalie J. Dean; Mark C Reichel

(57) ABSTRACT

Disclosed herein is a unique molecular marker in sorghum genome for conferring broad range fungal resistance trait, and the use of the molecular marker to manipulate resistance in sorghum. A disease resistance gene called ANTHRACNOSE RESISTANCE GENE 1 (ARG1) and a negative regulator, i.e. antisense transcripts of ARG1, called CARRIER OF ARG (CARG) for the fungi resistance gene are knocked out within a quantitative trait locus (QTL).

10 Claims, 84 Drawing Sheets

Specification includes a Sequence Listing.

FIGURE 12 Cont'd

Figure 14
FIG. 14A
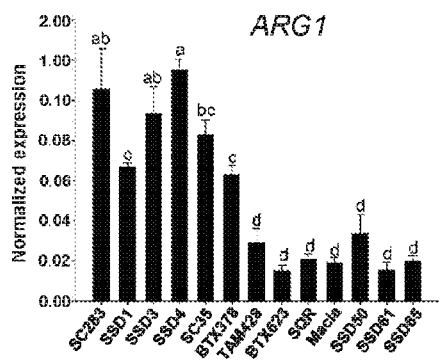
FIG. 14B
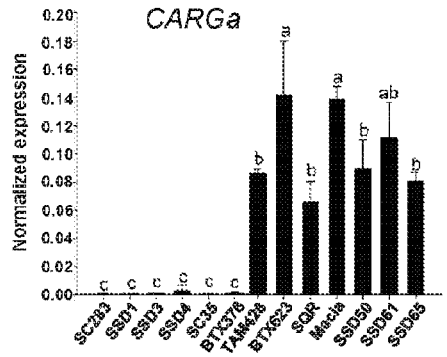
FIG. 14C
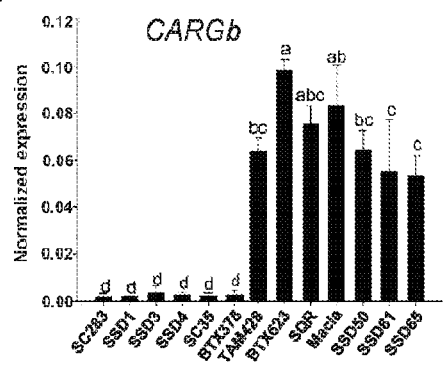

FIGURE 15

```
SC283      ATGGGCTCAGTGTTGTTTAGTCTATCATCCAAATGCCTTGACAAGCTTGCTGTACTGCTGGAGGAGGA
TAM428-U   ATGGGCTCAGTGTTGTTTAGTCTATCATCCAAATGCCTTGACAAGCTTGCTGTACTGCTGGAGGAGGA
TAM428-D   ATGGGCTCAGTGTTGTTTAGTCTATCATCCAAATGCCTTGACAAGCTTGCTGTACTGCTGGAGGAGGA
           ********************************************************************

SC283      GGTTATGATGACGCTTTCTGTGCGTAAAGATATCAGGAAGCTCCATGACTACCTCAAGTACTTCAATT
TAM428-U   GATTATGATGACGCTATCTGTGCGTAAAGAGATCAGGAAGCTCCATGACTACCTCAAGTACTTTGATT
TAM428-D   GATTATGATGACGCTATCTGTGCGTAAAGAGATCAGGAAGCTCCATGACTACCTCAAGTACTTTGATT
           *.************* ************* **************************.****** .***

SC283      CCATTCGTGAGGATGCTGATGCTCGGGCAATGGAACACAGAGAGACGACAGGAATATGGTGGGGTGAC
TAM428-U   CCATTCATGAGGATGCTGATGCTCGGGCAATGGAACACAGAGAGATGACAGGAATATGGTGGGGTGAC
TAM428-D   CCATTCATGAGGATGCTGATGCTCGGGCAATGGAACACAGAGAGATGACAGGAATATGGTGGGGTGAC
           ******.************************************** .*********************

SC283      GTGAAAGATGTCATGTATGATGTTGATGACATCATAGATCTTTTGAGGGCTCACTCTCAGAAGCAACG
TAM428-U   GTGAAAGATGTCATGTATGATGTTGATGACATCATAGATCTTTTGAGGGCTCACTCTCAGAAGCAACG
TAM428-D   GTGAAAGATGTCATGTATGATGTTGATGACATCATAGATCTTTTGAGGGCTCACTCTCAGAAGCAACG
           ********************************************************************

SC283      ATGTTGTGATTTACGCATGCTCTCTAGGTTTGCACAACTTCAATTTGACCACATGATTGCCAGAAAAA
TAM428-U   ATGTTGTGATTTACGCATGCTCTCTAGGTTTGCACAACTTCAATTTGACCACATGATTGCCAGAAAAA
TAM428-D   ATGTTGTGATTTACGCATGCTCTCTAGGTTTGCACAACTTCAATTTGACCACATGATTGCCAGAAAAA
           ********************************************************************

SC283      TCAAGGGTGTAAACGAAAGGCTTGTAGAAATCCAAAAGAACAGAGATATGTTCCTTCCTCCGGGGTTG
TAM428-U   TCAAGGGTGTAAACGAAAGGCTTGTAGAAATCCAAAAGAACAGAGATATGTTCCTTCCTCCGGGGTTG
TAM428-D   TCAAGGGTGTAAACGAAAGGCTTGTAGAAATCCAAAAGAACAGAGATATGTTCCTTCCTCCGGGGTTG
           ********************************************************************

SC283      TATCCTCAGGCTCAGGCCCCTCAAACAAACAGAGTTGATAGCAGGCATCTGGCTGCTTCGGTTGATGA
TAM428-U   TATCCTCAGGCTCAGGCCCCTCAAACAAACGGAGTTGATAGCAGGCATCTGGCTGCTTCGGTTGATGA
TAM428-D   TATCCTCAGGCTCAGGCCCCTCAAACAAACGGAGTTGATAGCAGGCATCTGGCTGCTTCGGTTGATGA
           ******************************.*************************************

SC283      AATCCATGTTGTTGGAGCAGAAATCAAGGAAGCTACTGATAGTATGGTAGAAATGATCGTCGGCTATG
TAM428-U   AATCCATGTTGTTGGAGCAGAAATCAAGGAAGCTACTGATAGTATGGTAGAAATGATTGTCGGTTATG
TAM428-D   AATCCATGTTGTTGGAGCAGAAATCAAGGAAGCTACTGATAGTATGGTAGAAATGATTGTCGGTTATG
           *********************************************************.*****.****

SC283      GCCATCAGAGCAGGATATCAGTTTATGGGATCGTTGGGATGGGAGGAATTGGCAAGACAACTTTAGCT
TAM428-U   GCCATCAGAGCAGGATATCAGTTTATGGGATCGTTGGGATGGGAGGAATTGGTAAGACAACTTTAGCT
TAM428-D   GCCATCAGAGCAGGATATCAGTTTATGGGATCGTTGGGATGGGAGGAATTGGTAAGACAACTTTAGCT
           ****************************************************.***************

SC283      CAGAAGATATACAATGATCGTAGGATAAGAGAGAGATTTCACCAGGTCCTCATCTGGCTGTCCATTTC
TAM428-U   CAGAAGATATACAATGATCGTAGGATAAGAGAGAGATTTCACCAGGTCCTCATCTGGCTGTCCATTTC
TAM428-D   CAGAAGATATACAATGATCGTAGGATAAGAGAGAGATTTCACCAGGTCCTCATCTGGCTGTCCATTTC
           ********************************************************************

SC283      ACAGAGCATTGCCGAGAATGATCTACTCAAGGAGGCCATCGAAAGGCAGGAGGGCAGTGCAATCAGC
TAM428-U   ACAGAGCATTGCCGAGAATGATCTACTCAAGGAGGCCATCGAAAGGCAGGAGGGCAGTGCAATCAGC
TAM428-D   ACAGAGCATTGCCGAGAATGATCTACTCAAGGAGGCCATCGAAAGGCAGGAGGGCAGTGCAATCAGC
```

SC283    ACAAGAGTAAGGATCAGCTCGTGCAAATTCTGCTACATTCCATCAGTGGGAAGAGTGTCTTTCTTGTG
TAM428-U ACAAGAGCAAGGATCAGCTCGTGCAAATTCTGCTACATTCCATCAGTGGGAAGAGTGTCTTTCTTGTG
TAM428-D ACAAGAGCAAGGATCAGCTCGTGCAAATTCTGCTACATTCCATCAGTGGGAAGAGTGTCTTTCTTGTG
         ******.*************************************************************

SC283    CTGGATAACGTTACCAACCCTGATGTGTGGATCGATCTTCTCCGCTCTCCGATGGAGAGGTGTTTGGA
TAM428-U CTGGATAACGTTACCAACCCTGATGTGTGGATCGATCTTCTCCGCTCTCCGATGGAGAGGTGTTTGGA
TAM428-D CTGGATAACGTTACCAACCCTGATGTGTGGATCGATCTTCTCCGCTCTCCGATGGAGAGGTGTTTGGA
         ********************************************************************

SC283    TGCTCATGTACTTGTTACCACAAGGAGCGGTCACGTATTGTCACAGATGAATGCGGTTCATGTCAAGG
TAM428-U TGCTCATGTACTTGTTACCACAAGGAGCGGTCACGTATTGTCACAGATGAATGCGGTGCATGTCAAGG
TAM428-D TGCTCATGTACTTGTTACCACAAGGAGCGGTCACGTATTGTCACAGATGAATGCGGTGCATGTCAAGG
         ********************************************************* **********

SC283    AAATGCATAGACTAAAGGATGCTGATGGCCTAGAACTGCTTATGAAGAGATCTTTCAGAACTGAAGAT
TAM428-U AAATGCACAGACTAAAGGATGCTGATGGCCTAGAACTGCTTATGAAGAGATCTTTCAGAACCAAAGAC
TAM428-D AAATGCACAGACTAAAGGATGCTGATGGCCTAGAACTGCTTATGAAGAGATCTTTCAGAACCAAAGAC
         *******.*****************************************************..****.

SC283    GAAGTAAATGTATTCAGTGATATTGGAGCAAAAATTGTTAAGAAATGTGATGGCCTTCCGCTTGCCAT
TAM428-U GAAGTAAATGTATTCAGTGATATTGGAGCAAAAATTGTTAAGAAATGTGATGGCCTTCCTCTTGCCAT
TAM428-D GAAGTAAATGTATTCAGTGATATTGGAGCAAAAATTGTTAAGAAATGTGATGGCCTTCCTCTTGCCAT
         ***********************************************************.********

SC283    CAAGGTCATTGGGGGCGTCCTATCATCCAGGTCGAGCAAAGAAGAATGGGAGAGAATACTGGAGAGAA
TAM428-U CAAGGTCATTGGAGGCGTCCTATCATCCAGGTCGAGCAAAGAAGAATGGGAGAGAATACTGGAGAGAA
TAM428-D CAAGGTCATTGGAGGCGTCCTATCATCCAGGTCGAGCAAAGAAGAATGGGAGAGAATACTGGAGAGAA
         ************.*******************************************************

SC283    GATGGTCTATTGATGGGCTTCCAGAAGAACTAGAAGGTGCTTTGTACTTAAGCTACAGTGACTTACAC
TAM428-U GATGGTCTATTGATGGGCTTCCAGAAGAACTAGAAGGTGCTTTGTACTTAAGCTACAGTGACTTACAC
TAM428-D GATGGTCTATTGATGGGCTTCCAGAAGAACTAGAAGGTGCTTTGTACTTAAGCTACAGTGACTTACAC
         ********************************************************************

SC283    CCACAACTGAAACAGTGCTTCCTCTGGTGTGCCTTGTTGCCCCAGAATTTCGATATTCACCGAGATGT
TAM428-U CCACAACTCAAACAGTGCTTCCTCTGCTGTGCCCTGTTGCCCTCAGAATTTCGATATTCACCGAGATGT
TAM428-D CCACAACTCAAACAGTGCTTCCTCTGCTGTGCCCTGTTGCCCTCAGAATTTCGATATTCACCGAGATGT
         ********.*****************.******.*******.*******.*******************

SC283    CACATACTGGTGGATTGCTGAAGGTCTTGTGAAGGAAGAGACCAGTGGACCAATACATAACGTCGCCG
TAM428-U CACATACTGGTGGATTGCTGAAGGTTTTGTGAAGGAAGAGGGCAGCGGACCGATACATAACATTGCCG
TAM428-D CACATACTGGTGGATTGCTGAAGGTTTTGTGAAGGAAGAGGGCAGCGGACCGATACATAACATTGCCG
         *************************.*************.***.*****.*********.*.****

SC283    AAGATTACTACCATGAGCTGATCAAGAGGAATCTGCTACAGGCAAGGCCAGAGTATGTCGACAAGGGA
TAM428-U AAGATTACTACCATGAGCTGATCAAGAGGAATCTGCTACAGGCAAGGCCAGAGTATGTCGACAAGGGA
TAM428-D AAGATTACTACCATGAGCTGATCAAGAGGAATCTGCTACAGGCAAGGCCAGAGTATGTCGACAAGGGA
         ********************************************************************

SC283    ATATCGACAATGCATGACCTGTTAAGGCAACTTGGCCAATTTCTGACAAGGAATGAAGCCGTCTTCAT
TAM428-U GTATCGACAATGCATGACCTGTTGAGGCAACTTGGCCAATTTCTGAAAAGAAATGAAGCCATCTTCAT
TAM428-D GTATCGACAATGCATGACCTGTTGAGGCAACTTGGCCAATTTCTGAAAAGAAATGAAGCCATCTTCA-
         .*********************.*********************** ***.***********.******
```

FIGURE 15 Cont'd

```
SC283      GAACGAGAAGCGTGATCGTTGCCCTTCTAGTATTCGCCGATTAGGTGTCGGGAGCGCTGTTGACGAAA
TAM428-U   GAACGAGAAGCGTGAACGTTGCCTT??????AGTATTCGCCGACTAGGTGTCGGGAGCGCTGTTGACGAAA
TAM428-D   -------------------------------------------------------------------

SC283      TACCTTCTATAGAAGAGAAGAAGCGCCTACGGTGCCTCATTGTCTTGGATCACGACACATGCAGATCG
TAM428-U   TACCTTCTATAGAAGAGAAGAAGCGCCTACGGTGCCTCATTGTCTTGCATCACGACACATGCAGATCG
TAM428-D   -------------------------------------------------------------------

SC283      GTGAAGAGGGACATCTTCAGAAAGCTGGTGCATCTTCGCATCTTAGTTCTACGTGGAGCAGGCCTCGA
TAM428-U   GTGAAGAGGGACATCTTCAGAAAGTTGGTGCATCTTCGCATCTTAGTTCTACGTGGAGCAGGCCTTGA
TAM428-D   -------------------------------------------------------------------

SC283      GAGCATACCTGCATCGGTGGGTTACTTGGCGCTGCTGAGGCTGCTGGATCTCAGCTACAACGAGATCA
TAM428-U   GAGCATACCTGCATCGGTGGGTTACTTGGCGCTGCTGAGGCTGCTGGATCTCAGCTACAATGAGATCA
TAM428-D   -------------------------------------------------------------------

SC283      AGGAGCTTCCGGGGTCCATCGGAAACCTTACCAGCCTTGGTTGCCTTTCAGTGTTTGGTTGCACAAAG
TAM428-U   AGGAGCTTCCAGGGTCCATCGGAAACCTTACCAGCCTTGGTTGCCTTTCAGTGTTTGGTTGCACAAAG
TAM428-D   -------------------------------------------------------------------

SC283      TTGGCAGCTTTGCCACAAAGTCTGATGAGGCTGACCACAATAAGCTTCCTCCAGATAGGAAACACAGG
TAM428-U   TTGGCAGCTTTGCCAACAAGTCTGATGAGGCTGACCACAATAAGCTTCCTCAAAATAGGAAACACAGG
TAM428-D   -------------------------------------------------------------------

SC283      ACTGGCGCAGGTTCCGAAAGGTATTGAGAATTTCAGGCAGATAGATAACCTTAGATCAGTTTTCCAAA
TAM428-U   ACTGGCGCAGGTTCCGAAAGGTATTGAGAATTTCAAGCAGATGGATAACCTTAGATCAGTTTTCCAAA
TAM428-D   -------------------------------------------------------------------

SC283      ACGGTACTGATGGTTTCAGATTAGATGAACTGAGGGCACTCTCCATGATACGACGCCTCTGGGTTATC
TAM428-U   ACGGTACTGATGGTTTCAGATTAGATGAACTGAGGGCACTCTCTATGATACGACGCCTCTGGGTTATC
TAM428-D   -------------------------------------------------------------------

SC283      CGGCTGGAGACAGCGACACCGCCAACTGAGCCCGTATTGTGCGACAAGGGTTACCTGAAAGAGCTAGG
TAM428-U   CGGCTGGAGACAGCGATACCGCCAACTGAGCCCATACTGTGCGACAAGGGTTACCTGAAAGAGCTAGG
TAM428-D   -------------------------------------------------------------------

SC283      CCTGCGCTGTACCATGGGCAAGGAAGCCAATTGTCGAACTCACTACCCGGACAGTAAGGTGAAGAGGA
TAM428-U   CCTGCGCTGCACCATGGGTAAGGAAGCCAATTGTCGAACTCACTATCCGGACAGCAAGGTGAAGAGGA
TAM428-D   -------------------------------------------------------------------

SC283      TTGAGGAGATCTACGAGAGTTTTTGCCCACCGCCAAGCCTAAGCTACGTCTTTATTGATGGGTTCCCT
TAM428-U   TTGAGGAGATCTACGAGAGTTTTTGCCCACCGCCAAGCCTAAGCTACGTCTTCATTGATGGGTTCCCT
TAM428-D   -------------------------------------------------------------------
```

FIGURE 15 Cont'd

```
SC283     GGTCGCATGTTTCCAACTTGGCTATCTTTAGAACCGCAGAATAAACTTCCAAACCTGGCTCATATGCA
TAM428-U  GGTTGCATGTTTCCAACTTGGCTATCTTCAGAACCGCAGAATAAACTGCCAAACCTGGCTCATATGCA
TAM428-D  -------------------------------------------------------------------

SC283     CTTCTATGACTGCATATCCTGCCCGAAGCTTCCCCCAGCAGGCCAGCTACCGTTTCTGCAGGTTCTTC
TAM428-U  CTTCAACGACTGCATATCCTGCCCGAAGCTTCCCCCAGCAGGCCAGCTACCGTTTCTGCAGGTTCTTC
TAM428-D  -------------------------------------------------------------------

SC283     ACGTCAAAGGAGCTGATGCAGTGGTGAACATAGGTGCTGAGCTCCTCGGAAACGGCATCCCATCTGGA
TAM428-U  ACGTCAAAGGAGCTGACGCAGTAGTGAACATAGGTGCTGAGCTCCTCGGAAACAGCATCCCATCCGGA
TAM428-D  -------------------------------------------------------------------

SC283     ACACATACCACTGCTTTTCCAAAGCTCGAGCTGCTTGAGATCCTCGACATGTACAACTGGCAGAATTG
TAM428-U  ACACATACCACTGCTTTTCCAAAGCTCGAGCTGCTTGAGATCCTCGACATGTACAACTGGCAGAATTG
TAM428-D  -------------------------------------------------------------------

SC283     GTCACTAAGCATGGATACCTTGTTCGAGAACACACAACAGCAATTCCTTATGCCATGCCTTACACGCC
TAM428-U  GTCACTAAGCATGGATACCTTGTTCGAGAAAACACAACAGCAATCCCTTATGCCATGCCTTACACGGC
TAM428-D  -------------------------------------------------------------------

SC283     TGCGGCTGATAAATTGCCCCAAGTTGAGAGCTCTCCCTGATCATCTTCACAGAGTTGTCAATCTACAA
TAM428-U  TGCGGCTGATAAATTGCCCCAAGTTGAGAGCTCTCCCTGATCATCTTCACAGAGTTGTCAATCTACAA
TAM428-D  ------------------------------------------------CAGAGTTGTCAATCTACAA
                                                          ******************

SC283     AGGATCCAAATAGAAGGAGCTGACAGCCTGCAGGAGGTTGTCAACCATCCCGGGGTTGTGTGGCTCAA
TAM428-U  AGGATCCAAATAGAAGGAGCTGACAGCCTGCAGGAGATTGTCAACCATCCCGGGGTTGTGTGGCTCAA
TAM428-D  AGGATCCAAATAGAAGGAGCTGACAGCCTGCAGGAGATTGTCAACCATCCCGGGGTTGTGTGGCTCAA
          ************************************.*****************************

SC283     GGTTAAGAACAACAAGTCCTTGAGGAATATATCCAACCTTCCTAAGCTGCGCCTCTTGCTTGCACAAG
TAM428-U  GGTTAAGAACAACAAGTCCTTGAGGAATATATCCAACCTTCCTAAGCTGCGCCTCTTGCTTGCACAAG
TAM428-D  GGTTAAGAACAACAAGTCCTTGAGGAATATATCCAACCTTCCTAAGCTGCGCCTCTTGCTTGCACAAG
          *******************************************************************

SC283     ATTGCCAAGAATTGCAGCAGGCAGAGAACCTTAGCTCACTCAAGGCCTTGTACGTTGTCGATTGCCCT
TAM428-U  ATTGCCAAGAATTGCAGCAGGCAGAGAACCTTAGCTCACTCAAGGCCTTGTACGTTGTCGATTGCCCT
TAM428-D  ATTGCCAAGAATTGCAGCAGGCAGAGAACCTTAGCTCACTCAAGGCCTTGTACGTTGTCGATTGCCCT
          *******************************************************************

SC283     ATGGAGCAGATACTCTGGAAGTGTTTCCCCATAGAACAACAGAGCACGATTGTCCGTGTTGTCACCAC
TAM428-U  ATGGAGCAGATACTCTGGAAGTGTTTCCCCATAGAACAACAGAGCACGATTGTCCGTGTTGTCACCAC
TAM428-D  ATGGAGCAGATACTCTGGAAGTGTTTCCCCATAGAACAACAGAGCACGATTGTCCGTGTTGTCACCAC
          *******************************************************************

SC283     TGGGGCCCATGGTCAGGATATTTATCCTCTTGAATCAGTATTTCATTAA
TAM428-U  TGGGGCCCATGGTCAGGATATTTATCCTCTTGAATCAGTATTTCATTAA
TAM428-D  TGGGGCCCATGGTCAGGATATTTATCCTCTTGAATCAGTATTTCATTAA
          *************************************************
```

```
PI585749     ATGGCTCAGTGTTGTTTAGTCTATCATCCAAATGCCTTGACAAGCTTGCTGTACTGCTG
PI586439     ATGXXCTCGGTGTTGTTTAGTCTATCATCCAAATGCCTTGACAAGCTTGCTGTACTGCTG
XS115        ATGGCTCAGTGTTGTTTAGTCTATCATCCAAATGCCTTGACAAGCTTGCTGTACTGCTG
Greenleaf    ATGGCTCAGTGTTGTTTAGTCTATCATCCAAATGCCTTGACAAGCTTGCTGTACTGCTG
BTX378       ATGGCTCAGTGTTGTTTAGTCTATCATCCAAATGCCTTGACAAGCTTGCTGTACTGCTG
SC35C        ATGGCTCGGTGTTGTTTAGTCTATCATCCAAATGCCTTGACAAGCTTGCTGTACTGCTG
SC283        ATGGCTCAGTGTTGTTTAGTCTATCATCCAAATGCCTTGACAAGCTTGCTGTACTGCTG
PI525695     ATGXXCTCGGTGTTGTTTAGTCTATCATCCAAATGCCTTGACAAGCTTGCTGTACTGCTG
A14          ATGGCTCAGTGTTGTTTAGTCTATCATCCAAATGCCTTGACAAGCTTGCTGTACTGCTG
SQR          ATGGCTCAGTGTTGTTTAGTCTATCATCCAAATGCCTTGACAAGCTTGCTGTACTGCTG
PQ434        ATGGCTCAGTGTTGTTTAGTCTATCATCCAAATGCCTTGACAAGCTTGCTGTACTGCTG
555          ATGXCTCAGTGTTGTTTAGTCTATCATCCAAATGCCTTGACAAGCTTGCTGTACTGCTG
R923         ATGGCTCAGTGTTGTTTAGTCTATCATCCAAATGCCTTGACAAGCTTGCTGTACTGCTG
Tetron       ATGGCTCAGTGTTGTTTAGTCTATCATCCAAATGCCTTGACAAGCTTGCTGTACTGCTG
1085         ATGXXCTCAGTGTTGTTTAGTCTATCATCCAAATGCCTTGACAAGCTTGCTGTACTGCTG
Ajabaido     ATGXXCTCAGTGTTGTTTAGTCTATCATCCAAATGCCTTGACAAGCTTGCTGTACTGCTG
BTX623       ATGGCTCAGTGTTGTTTAGTCTATCATCCAAATGCCTTGACAAGCTTGCTGTACTGCTG
BTX631       ATGGCTCAGTGTTGTTTAGTCTATCATCCAAATGCCTTGACAAGCTTGCTGTACTGCTG
BTX642       ATGGCTCAGTGTTGTTTAGTCTATCATCCAAATGCCTTGACAAGCTTGCTGTACTGCTG
IC9Y745      ATGGCTCAGTGTTGTTTAGTCTATCATCCAAATGCCTTGACAAGCTTGCTGTACTGCTG
IS9830       ATGXXCTCAGTGTTGTTTACTCTATCATCCAAATGCCTTGACAAGCTTGCTGTACTGCTG
J12731       ATGGCTCAGTGTTGTTTAGTCTATCATCCAAATGCCTTGACAAGCTTGCTGTACTGCTG
Keller       ATGGCTCAGTGTTGTTTAGTCTATCATCCAAATGCCTTGACAAGCTTGCTGTACTGCTG
M35-1        ATGGCTCAGTGTTGTTTAGTCTATCATCCAAATGCCTTGACAAGCTTGCTGTACTGCTG
Macia        ATGGCTCAGTGTTGTTTAGTCTATCATCCAAATGCCTTGACAAGCTTGCTGTACTGCTG
PI563516     ATGGCTCAGTGTTGTTTAGTCTATCATCCAAATGCCTTGACAAGCTTGCTGTACTGCTG
Rio          ATGGCTCACTGTTGTTTAGTCTATCATCCAAATGCCTTGACAAGCTTGCTGTACTGCTG
SC23         ATGGCTCAGTGTTGTTTAGTCTATCATCCAAATGCCTTGACAAGCTTGCTGTACTGCTG
SC52         ATGXXCTCAGTGTTGTTTAGTCTATCATCCAAATGCCTTGACAAGCTTGCTGTACTGCTG
SC55         ATGGCTCAGTGTTGTTTAGTCTATCATCCAAATGCCTTGACAAGCTTGCTGTACTGCTG
SC56         ATGXXCTCAGTGTTGTTTAGTCTATCATCCAAATGCCTTGACAAGCTTGCTGTACTGCTG
SC103        ATGXXCTCAGTGTTGTTTAGTCTATCATCCAAATGCCTTGACAAGCTTGCTGTACTGCTG
SC108C       ATGGCTCAGTGTTGTTTAGTCTATCATCCAAATGCCTTGACAAGCTTGCTGTACTGCTG
SC110        ATGGCTCAGTGTTGTTTAGTCTATCATCCAAATGCCTTGACAAGCTTGCTGTACTGCTG
SC155        ATGGCTCAGTGTTGTTTAGTCTATCATCCAAATGCCTTGACAAGCTTGCTGTACTGCTG
SC170        ATGGCTCAGTGTTGTTTAGTCTATCATCCAAATGCCTTGACAAGCTTGCTGTACTGCTG
SC301        ATGGCTCAGTGTTGTTTAGTCTATCATCCAAATGCCTTGACAAGCTTGCTGTACTGCTG
SC326        ATGGCTCAGTGTTGTTTAGTCTATCATCCAAATGCCTTGACAAGCTTGCTGTACTGCTG
SC650        ATGGCTCAGTGTTGTTTAGTCTATCATCCAAATGCCTTGACAAGCTTGCTGTACTGCTG
SC971        ATGGCTCAGTGTTGTTTAGTCTATCATCCAAATGCCTTGACAAGCTTGCTGTACTGCTG
SC1103       ATGGCTCAGTGTTGTTTAGTCTATCATCCAAATGCCTTGACAAGCTTGCTGTACTGCTG
SR839        ATGGCTCAGTGTTGTTTAGTCTATCATCCAAATGCCTTGACAAGCTTGCTGTACTGCTG
TAM428       ATGGCTCAGTGTTGTTTAGTCTATCATCCAAATGCCTTGACAAGCTTGCTGTACTGCTG
TX7000       ATGGCTCAGTGTTGTTTAGTCTATCATCCAAATGCCTTGACAAGCTTGCTGTACTGCTG
             ********  *******************************  *****************

PI585749     GAGGAGGAGGTTATGATGACGCTTTCTGTGCCTAAAGATATCAGGAAGCTCCATGAAAAC
PI586439     GAGGAGGAGGTTATGATGACGCTTTCTGTGCCTAAAGATATCAGGAAGCTCCATGAAAAC
XS115        GAGGAGGAGATTATGATGACGCTATCTGTGCCTAAAGACATCAGGAAGCTCCATGACTAC
Greenleaf    GAGGAGGAGGTTATGATGACGCTTTCTGTGCCTAAAGATATCAGGAAGCTCCATGACTAC
BTX378       GAGGAGGAGGTTATGATGACGCTTTCTGTGCCTAAAGATATCAGGAAGCTCCATGACTAC
SC35C        GAGGAGGAGTTATGATGACGCTTTCTGTGCCTAAAGATATCAGGAAGCTCCATGACTAC
SC283        GAGGAGGAGGTTATGATGACGCTTTCTGTGCCTAAAGATATCAGGAAGCTCCATGACTAC
PI525695     GAGGAGGAGGTTATGATGACGCTTTCTGTGCCTAAAGATATCAGGAAGCTCCATGACTAC
A14          GAGGAGGAGATTATGATGACGCTATCTGTGCCTAAAGACATCAGGAAGCTCCATGAAAAC
SQR          GAGGAGGAGATTATGATGACGCTATCTGTGCCTAAAGAGATCAGGAAGCTCCATGAAAAC
PQ434        GAGGAGGAGATTATGATGACGCTATCTGTGCCTAAAGACATCAGGAAGCTCCATGACTAC
```

| | |
|---|---|
| PI585749 | GATCTTTTGAGGGCTCACTCTCAGAAGCAACGATGTTGTGATTTACCCATGCTCTCTAGG |
| PI586439 | GATCTTTTGAGGGCTCACTCTCAGAAGCAACGATGTTGTGATTTACCCATGCTCTCTAGG |
| KS115 | GATCTTTTGAGGGCTCACTCTCAGAAGCAACGATGTTGTGATTTACCCATGCTCTCTAGG |
| Greenleaf | GATCTTTTGAGGGCTCACTCTCAGAAGCAACGATGTTGTGATTTACCCATGCTCTCTAGG |
| BTX378 | GATCTTTTGAGGGCTCACTCTCAGAAGCAACGATGTTGTGATTTACCCATGCTCTCTAGG |
| SC35C | GATCTTTTGAGGGCTCACTCTCAGAAGCAACGATGTTGTGATTTACCCATGCTCTCTAGG |
| SC283 | GATCTTTTGAGGGCTCACTCTCAGAAGCAACGATGTTGTGATTTACCCATGCTCTCTAGG |
| PI525695 | GATCTTTTGAGGGCTCACTCTCAGAAGCAACGATGTTGTGATTTACCCATGCTCTCTAGG |
| A14 | GATCTTTTGAGGGCTCACTCTCAGAAGCAACGATGTTGTGATTTACCCATGCTCTCTAGG |
| SQR | GATCTTTTGAGGGCTCACTCTCAGAAGCAACGATGTTGTGATTTACCCATGCTCTCTAGG |
| PQ434 | GATCTTTTGAGGGCTCACTCTCAGAAGCAACGATGTTGTGATTTACCCATGCTCTCTAGG |
| SSS | GATCTTTTGAGGGCTCACTCTCAGAAGCAACGATGTTGTGATTTACCCATGCTCTCTAGG |
| RP33 | GATCTTTTGAGGGCTCACTCTCAGAAGCAACGATGTTGTGATTTACCCATGCTCTCTAGG |
| Tetron | GATCTTTTGAGGGCTCACTCTCAGAAGCAACGATGTTGTGATTTACCCATGCTCTCTAGG |
| 1085 | GATCTTTTGAGGGCTCACTCTCAGAAGCAACGATGTTGTGATTTACCCATGCTCTCTAGG |
| Ajabsido | GATCTTTTGAGGGCTCACTCTCAGAAGCAACGATGTTGTGATTTACCCATGCTCTCTAGG |
| BTX623 | GATCTTTTGAGGGCTCACTCTCAGAAGCAACGATGTTGTGATTTACCCATGCTCTCTAGG |
| BTX631 | GATCTTTTGAGGGCTCACTCTCAGAAGCAACGATGTTGTGATTTACCCATGCTCTCTAGG |
| BTX642 | GATCTTTTGAGGGCTCACTCTCAGAAGCAACGATGTTGTGATTTACCCATGCTCTCTAGG |
| IC37749 | GATCTTTTGAGGGCTCACTCTCAGAAGCAACGATGTTGTGATTTACCCATGCTCTCTAGG |
| I89830 | GATCTTTTGAGGGCTCACTCTCAGAAGCAACGATGTTGTGATTTACCCATGCTCTCTAGG |
| J12731 | GATCTTTTGAGGGCTCACTCTCAGAAGCAACGATGTTGTGATTTACCCATGCTCTCTAGG |
| Keller | GATCTTTTGAGGGCTCACTCTCAGAAGCAACGATGTTGTGATTTACCCATGCTCTCTAGG |
| M35-1 | GATCTTTTGAGGGCTCACTCTCAGAAGCAACGATGTTGTGATTTACCCATGCTCTCTAGG |
| Macia | GATCTTTTGAGGGCTCACTCTCAGAAGCAACGATGTTGTGATTTACCCATGCTCTCTAGG |
| PI563516 | GATCTTTTGAGGGCTCACTCTCAGAAGCAACGATGTTGTGATTTACCCATGCTCTCTAGG |
| Rio | GATCTTTTGAGGGCTCACTCTCAGAAGCAACGATGTTGTGATTTACCCATGCTCTCTAGG |
| SC23 | GATCTTTTGAGGGCTCACTCTCAGAAGCAACGATGTTGTGATTTACCCATGCTCTCTAGG |
| SC52 | GATCTTTTGAGGGCTCACTCTCAGAAGCAACGATGTTGTGATTTACCCATGCTCTCTAGG |
| SC55 | GATCTTTTGAGGGCTCACTCTCAGAAGCAACGATGTTGTGATTTACCCATGCTCTCTAGG |
| SC56 | GATCTTTTGAGGGCTCACTCTCAGAAGCAACGATGTTGTGATTTACCCATGCTCTCTAGG |
| SC103 | GATCTTTTGAGGGCTCACTCTCAGAAGCAACGATGTTGTGATTTACCCATGCTCTCTAGG |
| SC108C | GATCTTTTGAGGGCTCACTCTCAGAAGCAACGATGTTGTGATTTACCCATGCTCTCTAGG |
| SC110 | GATCTTTTGAGGGCTCACTCTCAGAAGCAACGATGTTGTGATTTACCCATGCTCTCTAGG |
| SC155 | GATCTTTTGAGGGCTCACTCTCAGAAGCAACGATGTTGTGATTTACCCATGCTCTCTAGG |
| SC170 | GATCTTTTGAGGGCTCACTCTCAGAAGCAACGATGTTGTGATTTACCCATGCTCTCTAGG |
| SC301 | GATCTTTTGAGGGCTCACTCTCAGAAGCAACGATGTTGTGATTTACCCATGCTCTCTAGG |
| SC326 | GATCTTTTGAGGGCTCACTCTCAGAAGCAACGATGTTGTGATTTACCCATGCTCTCTAGG |
| SC650 | GATCTTTTGAGGGCTCACTCTCAGAAGCAACGATGTTGTGATTTACCCATGCTCTCTAGG |
| SC971 | GATCTTTTGAGGGCTCACTCTCAGAAGCAACGATGTTGTGATTTACCCATGCTCTCTAGG |
| SC1103 | GATCTTTTGAGGGCTCACTCTCAGAAGCAACGATGTTGTGATTTACCCATGCTCTCTAGG |
| SRN39 | GATCTTTTGAGGGCTCACTCTCAGAAGCAACGATGTTGTGATTTACCCATGCTCTCTAGG |
| TAM428 | GATCTTTTGAGGGCTCACTCTCAGAAGCAACGATGTTGTGATTTACCCATGCTCTCTAGG |
| TX7000 | GATCTTTTGAGGGCTCACTCTCAGAAGCAACGATGTTGTGATTTACCCATGCTCTCTAGG |
| | ************************ ************************ ************ |
| PI585749 | TTTGCACAACTTCAATTTGACCACATGATTGCCAGAAAATCAAGGGTGTAAACGAAAGG |
| PI586439 | TTTGCACAACTTCAATTTGACCACATGATTGCCAGAAAATCAAGGGTGTAAACGAAAGG |
| KS115 | TTTGCACAACTTCAATTTGACCACATGATTGCCAGAAAATCAAGGGTGTAAACGAAAGG |
| Greenleaf | TTTGCACAACTTCAATTTGACCACATGATTGCCAGAAAATCAAGGGTGTAAACGAAAGG |
| BTX378 | TTTGCACAACTTCAATTTGACCACATGATTGCCAGAAAATCAAGGGTGTAAACGAAAGG |
| SC35C | TTTGCACAACTTCAATTTGACCACATGATTGCCAGAAAATCAAGGGTGTAAACGAAAGG |
| SC283 | TTTGCACAACTTCAATTTGACCACATGATTGCCAGAAAATCAAGGGTGTAAACGAAAGG |
| PI525695 | TTTGCACAACTTCAATTTGACCACATGATTGCCAGAAAATCAAGGGTGTAAACGAAAGG |
| A14 | TTTGCACAACTTCAATTTGACCACATGATTGCCAGAAAATCAAGGGTGTAAACGAAAGG |
| SQR | TTTGCACAACTTCAATTTGACCACATGATTGCCAGAAAATCAAGGGTGTAAACGAAAGG |
| PQ434 | TTTGCACAACTTCAATTTGACCACATGATTGCCAGAAAATCAAGGGTGTAAACGAAAGG |
| SSS | TTTGCACAACTTCAATTTGACCACATGATTGCCAGAAAATCAAGGGTGTAAACGAAAGG |
| RP33 | TTTGCACAACTTCAATTTGACCACATGATTGCCAGAAAATCAAGGGTGTAAACGAAAGG |
| Tetron | TTTGCACAACTTCAATTTGACCACATGATTGCCAGAAAATCAAGGGTGTAAACGAAAGG |
| 1085 | TTTGCACAACTTCAATTTGACCACATGATTGCCAGAAAATCAAGGGTGTAAACGAAAGG |
| Ajabsido | TTTGCACAACTTCAATTTGACCACATGATTGCCAGAAAATCAAGGGTGTAAACGAAAGG |

FIG. 16B Cont'd

| | |
|---|---|
| BTX623 | TTTCCACAACTTCAATTTGACCACATGATTGCCAGAAAATCAAGGGTGTAAACGAAGG |
| BTX631 | TTTCCACAACTTCAATTTGACCACATGATTGCCAGAAAATCAAGGGTGTAAACGAAGG |
| BTX642 | TTTCCACAACTTCAATTTGACCACATGATTGCCAGAAAATCAAGGGTGTAAACGAAGG |
| ICSV745 | TTTCCACAACTTCAATTTGACCACATGATTGCCAGAAAATCAAGGGTGTAAACGAAGG |
| IS9830 | TTTCCACAACTTCAATTTGACCACATGATTGCCAGAAAATCAAGGGTGTAAACGAAGG |
| J12731 | TTTCCACAACTTCAATTTGACCACATGATTGCCAGAAAATCAAGGGTGTAAACGAAGG |
| Keller | TTTCCACAACTTCAATTTGACCACATGATTGCCAGAAAATCAAGGGTGTAAACGAAGG |
| M35-1 | TTTCCACAACTTCAATTTGACCACATGATTGCCAGAAAATCAAGGGTGTAAACGAAGG |
| Macia | TTTCCACAACTTCAATTTGACCACATGATTGCCAGAAAATCAAGGGTGTAAACGAAGG |
| PI563516 | TTTCCACAACTTCAATTTGACCACATGATTGCCAGAAAATCAAGGGTGTAAACGAAGG |
| Rio | TTTCCACAACTTCAATTTGACCACATGATTGCCAGAAAATCAAGGGTGTAAACGAAGG |
| SC23 | TTTCCACAACTTCAATTTGACCACATGATTGCCAGAAAATCAAGGGTGTAAACGAAGG |
| SC52 | TTTCCACAACTTCAATTTGACCACATGATTGCCAGAAAATCAAGGGTGTAAACGAAGG |
| SC55 | TTTCCACAACTTCAATTTGACCACATGATTGCCAGAAAATCAAGGGTGTAAACGAAGG |
| SC56 | TTTCCACAACTTCAATTTGACCACATGATTGCCAGAAAATCAAGGGTGTAAACGAAGG |
| SC103 | TTTCCACAACTTCAATTTGACCACATGATTGCCAGAAAATCAAGGGTGTAAACGAAGG |
| SC108C | TTTCCACAACTTCAATTTGACCACATGATTGCCAGAAAATCAAGGGTGTAAACGAAGG |
| SC110 | TTTCCACAACTTCAATTTGACCACATGATTGCCAGAAAATCAAGGGTGTAAACGAAGG |
| SC155 | TTTCCACAACTTCAATTTGACCACATGATTGCCAGAAAATCAAGGGTGTAAACGAAGG |
| SC170 | TTTCCACAACTTCAATTTGACCACATGATTGCCAGAAAATCAAGGGTGTAAACGAAGG |
| SC301 | TTTCCACAACTTCAATTTGACCACATGATTGCCAGAAAATCAAGGGTGTAAACGAAGG |
| SC326 | TTTCCACAACTTCAATTTGACCACATGATTGCCAGAAAATCAAGGGTGTAAACGAAGG |
| SC650 | TTTCCACAACTTCAATTTGACCACATGATTGCCAGAAAATCAAGGGTGTAAACGAAGG |
| SC971 | TTTCCACAACTTCAATTTGACCACATGATTGCCAGAAAATCAAGGGTGTAAACGAAGG |
| SC1103 | TTTCCACAACTTCAATTTGACCACATGATTGCCAGAAAATCAAGGGTGTAAACGAAGG |
| SRN39 | TTTCCACAACTTCAATTTGACCACATGATTGCCAGAAAATCAAGGGTGTAAACGAAGG |
| TAM428 | TTTCCACAACTTCAATTTGACCACATGATTGCCAGAAAATCAAGGGTGTAAACGAAGG |
| TX7000 | TTTCCACAACTTCAATTTGACCACATGATTGCCAGAAAATCAAGGGTGTAAACGAAGG |
| | ************************************************************ |
| | |
| PI585749 | CTTGTAGAAATCCAAAAGAACAGAGATATGTTCCTTCCTCCGGGTTGTATCCTCAGGCA |
| PI586435 | CTTGTAGAAATCCAAAAGAACAGAGATATGTTCCTTCCTCCGGGTTGTATCCTCAGGCA |
| KS115 | CTTGTAGAAATCCAAAAGAACAGAGATATGTTCCTTCCTCCGGGTTGTATCCTCAGGCT |
| Greenleaf | CTTGTAGAAATCCAAAAGAACAGAGATATGTTCCTTCCTCCGGGTTGTATCCTCAGGCT |
| BTX378 | CTTGTAGAAATCCAAAAGAACAGAGATATGTTCCTTCCTCCGGGTTGTATCCTCAGGCT |
| SC35C | CTTGTAGAAATCCAAAAGAACAGAGATATGTTCCTTCCTCCGGGTTGTATCCTCAGGCT |
| SC283 | CTTGTAGAAATCCAAAAGAACAGAGATATGTTCCTTCCTCCGGGTTGTATCCTCAGGCT |
| PI525695 | CTTGTAGAAATCCAAAAGAACAGAGATATGTTCCTTCCTCCGGGTTGTATCCTCAGGCT |
| A14 | CTTGTAGAAATCCAAAAGAACAGAGATATGTTCCTTCCTCCGGGTTGTATCCTCAGGCT |
| SQR | CTTGTAGAAATCCAAAAGAACAGAGATATGTTCCTTCCTCCGGGTTGTATCCTCAGGCT |
| PQ434 | CTTGTAGAAATCCAAAAGAACAGAGATATGTTCCTTCCTCCGGGTTGTATCCTCAGGCT |
| 555 | CTTGTAGAAATCCAAAAGAACAGAGATATGTTCCTTCCTCCGGGTTGTATCCTCAGGCT |
| X233 | CTTGTAGAAATCCAAAAGAACAGAGATATGTTCCTTCCTCCGGGTTGTATCCTCAGGCT |
| Tetron | CTTGTAGAAATCCAAAAGAACAGAGATATGTTCCTTCCTCCGGGTTGTATCCTCAGGCT |
| 1085 | CTTGTAGAAATCCAAAAGAACAGAGATATGTTCCTTCCTCCGGGTTGTATCCTCAGGCT |
| Ajabsido | CTTGTAGAAATCCAAAAGAACAGAGATATGTTCCTTCCTCCGGGTTGTATCCTCAGGCT |
| BTX623 | CTTGTAGAAATCCAAAAGAACAGAGATATGTTCCTTCCTCCGGGTTGTATCCTCAGGCT |
| BTX631 | CTTGTAGAAATCCAAAAGAACAGAGATATGTTCCTTCCTCCGGGTTGTATCCTCAGGCT |
| BTX642 | CTTGTAGAAATCCAAAAGAACAGAGATATGTTCCTTCCTCCGGGTTGTATCCTCAGGCT |
| ICSV745 | CTTGTAGAAATCCAAAAGAACAGAGATATGTTCCTTCCTCCGGGTTGTATCCTCAGGCT |
| IS9830 | CTTGTAGAAATCCAAAAGAACAGAGATATGTTCCTTCCTCCGGGTTGTATCCTCAGGCT |
| J12731 | CTTGTAGAAATCCAAAAGAACAGAGATATGTTCCTTCCTCCGGGTTGTATCCTCAGGCT |
| Keller | CTTGTAGAAATCCAAAAGAACAGAGATATGTTCCTTCCTCCGGGTTGTATCCTCAGGCT |
| M35-1 | CTTGTAGAAATCCAAAAGAACAGAGATATGTTCCTTCCTCCGGGTTGTATCCTCAGGCT |
| Macia | CTTGTAGAAATCCAAAAGAACAGAGATATGTTCCTTCCTCCGGGTTGTATCCTCAGGCT |
| PI563516 | CTTGTAGAAATCCAAAAGAACAGAGATATGTTCCTTCCTCCGGGTTGTATCCTCAGGCT |
| Rio | CTTGTAGAAATCCAAAAGAACAGAGATATGTTCCTTCCTCCGGGTTGTATCCTCAGGCT |
| SC23 | CTTGTAGAAATCCAAAAGAACAGAGATATGTTCCTTCCTCCGGGTTGTATCCTCAGGCT |
| SC52 | CTTGTAGAAATCCAAAAGAACAGAGATATGTTCCTTCCTCCGGGTTGTATCCTCAGGCT |
| SC55 | CTTGTAGAAATCCAAAAGAACAGAGATATGTTCCTTCCTCCGGGTTGTATCCTCAGGCT |
| SC56 | CTTGTAGAAATCCAAAAGAACAGAGATATGTTCCTTCCTCCGGGTTGTATCCTCAGGCT |
| SC103 | CTTGTAGAAATCCAAAAGAACAGAGATATGTTCCTTCCTCCGGGTTGTATCCTCAGGCT |
| SC108C | CTTGTAGAAATCCAAAAGAACAGAGATATGTTCCTTCCTCCGGGTTGTATCCTCAGGCT |

| | |
|---|---|
| BTX378 | CATGTTCTTGGAGCAGAAATCAAGGAAGCTACTGATAGTATGGTAGAAATGATCGTCGGT |
| SC35C | CATGTTCTTGGAGCAGAAATCAAGGAAGCTACTGATAGTATGGTAGAAATGATCGTCGGT |
| SC283 | CATGTTCTTGGAGCAGAAATCAAGGAAGCTACTGATAGTATGGTAGAAATGATCGTCGGT |
| PI525695 | CATGTTCTTGGAGCAGAAATCAAGGAAGCTACTGATAGTATGGTAGAAATGATCGTCGGT |
| A14 | CATGTTCTTGGAGCAGAAATCAAGGAAGCTACTGATAGTATGGTAGAAATGATCGTCGGT |
| SQR | CATGTTCTTGGAGCAGAAATCAAGGAAGCTACTGATAGTATGGTAGAAATGATCGTCGGT |
| PQ434 | CATGTTCTTGGAGCAGAAATCAAGGAAGCTACTGATAGTATGGTAGAAATGATCGTCGGT |
| 555 | CATGTTCTTGGAGCAGAAATCAAGGAAGCTACTGATAGTATGGTAGAAATGATCGTCGGT |
| KP33 | CATGTTCTTGGAGCAGAAATCAAGGAAGCTACTGATAGTATGGTAGAAATGATCGTCGGT |
| Tetron | CATGTTCTTGGAGCAGAAATCAAGGAAGCTACTGATAGTATGGTAGAAATGATCGTCGGT |
| 1585 | CATGTTCTTGGAGCAGAAATCAAGGAAGCTACTGATAGTATGGTAGAAATGATCGTCGGT |
| Ajabsido | CATGTTCTTGGAGCAGAAATCAAGGAAGCTACTGATAGTATGGTAGAAATGATCGTCGGT |
| BTX623 | CATGTTCTTGGAGCAGAAATCAAGGAAGCTACTGATAGTATGGTAGAAATGATCGTCGGT |
| BTX631 | CATGTTCTTGGAGCAGAAATCAAGGAAGCTACTGATAGTATGGTAGAAATGATCGTCGGT |
| BTX642 | CATGTTCTTGGAGCAGAAATCAAGGAAGCTACTGATAGTATGGTAGAAATGATCGTCGGT |
| ICSV745 | CATGTTCTTGGAGCAGAAATCAAGGAAGCTACTGATAGTATGGTAGAAATGATCGTCGGT |
| IS9830 | CATGTTCTTGGAGCAGAAATCAAGGAAGCTACTGATAGTATGGTAGAAATGATCGTCGGT |
| J12731 | CATGTTCTTGGAGCAGAAATCAAGGAAGCTACTGATAGTATGGTAGAAATGATCGTCGGT |
| Keller | CATGTTCTTGGAGCAGAAATCAAGGAAGCTACTGATAGTATGGTAGAAATGATCGTCGGT |
| M35-1 | CATGTTCTTGGAGCAGAAATCAAGGAAGCTACTGATAGTATGGTAGAAATGATCGTCGGT |
| Macia | CATGTTCTTGGAGCAGAAATCAAGGAAGCTACTGATAGTATGGTAGAAATGATCGTCGGT |
| PI563316 | CATGTTCTTGGAGCAGAAATCAAGGAAGCTACTGATAGTATGGTAGAAATGATCGTCGGT |
| RIO | CATGTTCTTGGAGCAGAAATCAAGGAAGCTACTGATAGTATGGTAGAAATGATCGTCGGT |
| SC23 | CATGTTCTTGGAGCAGAAATCAAGGAAGCTACTGATAGTATGGTAGAAATGATCGTCGGT |
| SC52 | CATGTTCTTGGAGCAGAAATCAAGGAAGCTACTGATAGTATGGTAGAAATGATCGTCGGT |
| SC55 | CATGTTCTTGGAGCAGAAATCAAGGAAGCTACTGATAGTATGGTAGAAATGATCGTCGGT |
| SC56 | CATGTTCTTGGAGCAGAAATCAAGGAAGCTACTGATAGTATGGTAGAAATGATCGTCGGT |
| SC103 | CATGTTCTTGGAGCAGAAATCAAGGAAGCTACTGATAGTATGGTAGAAATGATCGTCGGT |
| SC108C | CATGTTCTTGGAGCAGAAATCAAGGAAGCTACTGATAGTATGGTAGAAATGATCGTCGGT |
| SC110 | CATGTTCTTGGAGCAGAAATCAAGGAAGCTACTGATAGTATGGTAGAAATGATCGTCGGT |
| SC155 | CATGTTCTTGGAGCAGAAATCAAGGAAGCTACTGATAGTATGGTAGAAATGATCGTCGGT |
| SC170 | CATGTTCTTGGAGCAGAAATCAAGGAAGCTACTGATAGTATGGTAGAAATGATCGTCGGT |
| SC301 | CATGTTCTTGGAGCAGAAATCAAGGAAGCTACTGATAGTATGGTAGAAATGATCGTCGGT |
| SC326 | CATGTTCTTGGAGCAGAAATCAAGGAAGCTACTGATAGTATGGTAGAAATGATCGTCGGT |
| SC650 | CATGTTCTTGGAGCAGAAATCAAGGAAGCTACTGATAGTATGGTAGAAATGATCGTCGGT |
| SC871 | CATGTTCTTGGAGCAGAAATCAAGGAAGCTACTGATAGTATGGTAGAAATGATCGTCGGT |
| SC1103 | CATGTTCTTGGAGCAGAAATCAAGGAAGCTACTGATAGTATGGTAGAAATGATCGTCGGT |
| SM39 | CATGTTCTTGGAGCAGAAATCAAGGAAGCTACTGATAGTATGGTAGAAATGATCGTCGGT |
| TAM428 | CATGTTCTTGGAGCAGAAATCAAGGAAGCTACTGATAGTATGGTAGAAATGATCGTCGGT |
| TX7000 | CATGTTCTTGGAGCAGAAATCAAGGAAGCTACTGATAGTATGGTAGAAATGATCGTCGGT |
| | ************************************************************ |
| PI585749 | TATGCCCATCAGAGCAGGATATCAGTTTATGGATCGTTGGGATGGAGCAATTGGCAAG |
| PI586439 | TATGCCCATCAGAGCAGGATATCAGTTTATGGATCGTTGGGATGGAGCAATTGGCAAG |
| X9115 | TATGCCCATCAGAGCAGGATATCAGTTTATGGATCGTTGGGATGGAGCAATTGGTAAG |
| Greenleaf | TATGCCCATCAGAGCAGGATATCAGTTTATGGATCGTTGGGATGGAGCAATTGGCAAG |
| BTX378 | TATGCCCATCAGAGCAGGATATCAGTTTATGGATCGTTGGGATGGAGCAATTGGCAAG |
| SC35C | TATGCCCATCAGAGCAGGATATCAGTTTATGGATCGTTGGGATGGAGCAATTGGCAAG |
| SC283 | TATGCCCATCAGAGCAGGATATCAGTTTATGGATCGTTGGGATGGAGCAATTGGCAAG |
| PI525695 | TATGCCCATCAGAGCAGGATATCAGTTTATGGATCGTTGGGATGGAGCAATTGGCAAG |
| A14 | TATGCCCATCAGAGCAGGATATCAGTTTATGGATCGTTGGGATGGAGCAATTGGTAAG |
| SQR | TATGCCCATCAGAGCAGGATATCAGTTTATGGATCGTTGGGATGGAGCAATTGGTAAG |
| PQ434 | TATGCCCATCAGAGCAGGATATCAGTTTATGGATCGTTGGGATGGAGCAATTGGTAAG |
| 555 | TATGCCCATCAGAGCAGGATATCAGTTTGTGGATCGTTGGGATGGAGCAATTGGTAAG |
| KP33 | TATGCCCATCAGAGCAGGATATCAGTTTGTGGATCGTTGGGATGGAGCAATTGGTAAG |
| Tetron | TATGCCCATCAGAGCAGGATATCAGTTTGTGGATCGTTGGGATGGAGCAATTGGTAAG |
| 1585 | TATGCCCATCAGAGCAGGATATCAGTTTATGGATCGTTGGGATGGAGCAATTGGTAAG |
| Ajabsido | TATGCCCATCAGAGCAGGATATCAGTTTATGGATCGTTGGGATGGAGCAATTGGTAAG |
| BTX623 | TATGCCCATCAGAGCAGGATATCAGTTTATGGATCGTTGGGATGGAGCAATTGGTAAG |
| BTX631 | TATGCCCATCAGAGCAGGATATCAGTTTATGGATCGTTGGGATGGAGCAATTGGTAAG |
| BTX642 | TATGCCCATCAGAGCAGGATATCAGTTTATGGATCGTTGGGATGGAGCAATTGGTAAG |
| ICSV745 | TATGCCCATCAGAGCAGGATATCAGTTTATGGATCGTTGGGATGGAGCAATTGGTAAG |
| IS9830 | TATGCCCATCAGAGCAGGATATCAGTTTATGGATCGTTGGGATGGAGCAATTGGTAAG |

| | |
|---|---|
| SC658 | ACAACTTTAGCTCAGAAGATATACAATGATCGTAGGATAAGAGAGAGATTTCACCAGGTC |
| SC971 | ACAACTTTAGCTCAGAAGATATACAATGATCGTAGGATAAGAGAGAGATTTCACCAGGTC |
| SC1103 | ACAACTTTAGCTCAGAAGATATACAATGATCGTAGGATAAGAGAGAGATTTCACCAGGTC |
| SRN39 | ACAACTTTAGCTCAGAAGATATACAATGATCGTAGGATAAGAGAGAGATTTCACCAGGTC |
| TAM428 | ACAACTTTAGCTCAGAAGATATACAATGATCGTAGGATAAGAGAGAGATTTCACCAGGTC |
| TX7000 | ACAACTTTAGCTCAGAAGATATACAATGATCGTAGGATAAGAGAGAGATTTCACCAGGTC |
| | ************ ***************** *********************** * |
| | |
| PI585749 | CTCATCTGGCTGTCCATTCACAGAGCATTGCCGAGAATGATCTACTCAAGGAGGCCATC |
| PI586478 | CTCATCTGGCTGTCCATTCACAGAGCATTGCCGAGAATGATCTACTCAAGGAGGCCATC |
| KS115 | CTCATCTGGCTGTCCATTCACAGAGCATTGCCGAGAATGATCTACTCAAGGAGGCCATC |
| Greenleaf | CTCATCTGGCTGTCCATTCACAGAGCATTGCCGAGAATGATCTACTCAAGGAGGCCATC |
| BTX378 | CTCATCTGGCTGTCCATTCACAGAGCATTGCCGAGAATGATCTACTCAAGGAGGCCATC |
| SC35C | CTCATCTGGCTGTCCATTCACAGAGCATTGCCGAGAATGATCTACTCAAGGAGGCCATC |
| SC283 | CTCATCTGGCTGTCCATTCACAGAGCATTGCCGAGAATGATCTACTCAAGGAGGCCATC |
| PI525695 | CTCATCTGGCTGTCCATTCACAGAGCATTGCCGAGAATGATCTACTCAAGGAGGCCATC |
| A14 | CTCATCTGGCTGTCCATTCACAGAGCATTGCCGAGAATGATCTACTCAAGGAGGCCATC |
| SQR | CTCATCTGGCTGTCCATTCACAGAGCATTGCCGAGAATGATCTACTCAAGGAGGCCATC |
| PQ434 | CTCATCTGGCTGTCCATTCACAGAGCATTGCCGAGAATGATCTACTCAAGGAGGCCATC |
| 355 | CTCATCTGGCTGTCCATTCACAGAGCATTGCCGAGAATGATCTACTCAAGGAGGCCATC |
| KP33 | CTCATCTGGCTGTCCATTCACAGGGCATTGCCGAGAATGATCTACTCAAGGAGGCCATC |
| Tetron | CTCATCTGGCTGTCCATTCACAGGGCATTGCCGAGAATGATCTACTCAAGGAGGCCATC |
| 1085 | CTCATCTGGCTGTCCATTCACAGAGCATTGCCGAGAATGATCTACTCAAGGAGGCCATC |
| Ajabsido | CTCATCTGGCTGTCCATTCACAGAGCATTGCCGAGAATGATCTACTCAAGGAGGCCATC |
| BTX623 | CTCATCTGGCTGTCCATTCACAGAGCATTGCCGAGAATGATCTACTCAAGGAGGCCATC |
| BTX631 | CTCATCTGGCTGTCCATTCACAGAGCATTGCCGAGAATGATCTACTCAAGGAGGCCATC |
| BTX642 | CTCATCTGGCTGTCCATTCACAGAGCATTGCCGAGAATGATCTACTCAAGGAGGCCATC |
| ICSV745 | CTCATCTGGCTGTCCATTCACAGAGCATTGCCGAGAATGATCTACTCAAGGAGGCCATC |
| 169830 | CTCATCTGGCTGTCCATTCACAGAGCATTGCCGAGAATGATCTACTCAAGGAGGCCATC |
| J12731 | CTCATCTGGCTGTCCATTCACAGAGCATTGCCGAGAATGATCTACTCAAGGAGGCCATC |
| Keller | CTCATCTGGCTGTCCATTCACAGAGCATTGCCGAGAATGATCTACTCAAGGAGGCCATC |
| M35-1 | CTCATCTGGCTGTCCATTCACAGAGCATTGCCGAGAATGATCTACTCAAGGAGGCCATC |
| Macia | CTCATCTGGCTGTCCATTCACAGAGCATTGCCGAGAATGATCTACTCAAGGAGGCCATC |
| PI563516 | CTCATCTGGCTGTCCATTCACAGAGCATTGCCGAGAATGATCTACTCAAGGAGGCCATC |
| Rio | CTCATCTGGCTGTCCATTCACAGAGCATTGCCGAGAATGATCTACTCAAGGAGGCCATC |
| SC23 | CTCATCTGGCTGTCCATTCACAGAGCATTGCCGAGAATGATCTACTCAAGGAGGCCATC |
| SC52 | CTCATCTGGCTGTCCATTCACAGAGCATTGCCGAGAATGATCTACTCAAGGAGGCCATC |
| SC35 | CTCATCTGGCTGTCCATTCACAGAGCATTGCCGAGAATGATCTACTCAAGGAGGCCATC |
| SC56 | CTCATCTGGCTGTCCATTCACAGAGCATTGCCGAGAATGATCTACTCAAGGAGGCCATC |
| SC103 | CTCATCTGGCTGTCCATTCACAGAGCATTGCCGAGAATGATCTACTCAAGGAGGCCATC |
| SC108C | CTCATCTGGCTGTCCATTCACAGAGCATTGCCGAGAATGATCTACTCAAGGAGGCCATC |
| SC120 | CTCATCTGGCTGTCCATTCACAGAGCATTGCCGAGAATGATCTACTCAAGGAGGCCATC |
| SC155 | CTCATCTGGCTGTCCATTCACAGAGCATTGCCGAGAATGATCTACTCAAGGAGGCCATC |
| SC170 | CTCATCTGGCTGTCCATTCACAGAGCATTGCCGAGAATGATCTACTCAAGGAGGCCATC |
| SC301 | CTCATCTGGCTGTCCATTCACAGAGCATTGCCGAGAATGATCTACTCAAGGAGGCCATC |
| SC326 | CTCATCTGGCTGTCCATTCACAGAGCATTGCCGAGAATGATCTACTCAAGGAGGCCATC |
| SC650 | CTCATCTGGCTGTCCATTCACAGAGCATTGCCGAGAATGATCTACTCAAGGAGGCCATC |
| SC971 | CTCATCTGGCTGTCCATTCACAGAGCATTGCCGAGAATGATCTACTCAAGGAGGCCATC |
| SC1103 | CTCATCTGGCTGTCCATTCACAGAGCATTGCCGAGAATGATCTACTCAAGGAGGCCATC |
| SRN39 | CTCATCTGGCTGTCCATTCACAGAGCATTGCCGAGAATGATCTACTCAAGGAGGCCATC |
| TAM428 | CTCATCTGGCTGTCCATTCACAGAGCATTGCCGAGAATGATCTACTCAAGGAGGCCATC |
| TX7000 | CTCATCTGGCTGTCCATTCACAGAGCATTGCCGAGAATGATCTACTCAAGGAGGCCATC |
| | ***************** **** ************************************ |
| | |
| PI585749 | GAAAGCCAGGAGGGCAGTGCAATCAGCACAAGAGTAAGGATCAGCTCGTGCAAATTCTG |
| PI586478 | GAAAGCCAGGAGGGCAGTGCAATCAGCACAAGAGTAAGGATCAGCTCGTGCAAATTCTG |
| KS115 | GAAAGCCAGGAGGGCAGTGCAATCAGCACAAGAGTAAGGATCAGCTCGTGCAAATTCTG |
| Greenleaf | GAAAGCCAGGAGGGCAGTGCAATCAGCACAAGAGTAAGGATCAGCTCGTGCAAATTCTG |
| BTX378 | GAAAGCCAGGAGGGCAGTGCAATCAGCACAAGAGTAAGGATCAGCTCGTGCAAATTCTG |
| SC35C | GAAAGCCAGGAGGGCAGTGCAATCAGCACAAGAGTAAGGATCAGCTCGTGCAAATTCTG |
| SC283 | GAAAGCCAGGAGGGCAGTGCAATCAGCACAAGAGTAAGGATCAGCTCGTGCAAATTCTG |
| PI525695 | GAAAGCCAGGAGGGCAGTGCAATCAGCACAAGAGTAAGGATCAGCTCGTGCAAATTCTG |
| A14 | GAAAGCCAGGAGGGCAGTGCAATCAGCACAAGAGTAAGGATCAGCTCGTGCAAATTCTG |

| | |
|---|---|
| TX7000 | GTGCCATCGATCTTCTCCACTTCCGATGGGAGCTGTTTGGATCCAAGTACTTGTT |
| | ************************************************* |

| | |
|---|---|
| PI585749 | ACCACAAGGAGCCGTCACGTATTGTCACAGATGAATGCCGTTCATGTCAAGGAAATGCAC |
| PI586439 | ACCACAAGGAGCCGTCACGTATTGTCACAGATGAATGCCGTTCATGTCAAGGAAATGCAT |
| KS115 | ACCACAAGGAGCCGTCACGTATTGTCACAGATGAATGCCGTGCATGTCAAGGAAATGCAC |
| Greenleaf | ACCACAAGGAGCCGTCACGTATTGTCACAGATGAATGCCGTTCATGTCAAGGAAATGCAT |
| BTX378 | ACCACAAGGAGCCGTCACGTATTGTCACAGATGAATGCCGTTCATGTCAAGGAAATGCAT |
| SC35C | ACCACAAGGAGCCGTCACGTATTGTCACAGATGAATGCCGTTCATGTCAAGGAAATGCAT |
| SC283 | ACCACAAGGAGCCGTCACGTATTGTCACAGATGAATGCCGTTCATGTCAAGGAAATGCAT |
| PI525695 | ACCACAAGGAGCCGTCACGTATTGTCACAGATGAATGCCGTTCATGTCAAGGAAATGCAT |
| A14 | ACCACAAGGAGCCGTCACGTATTGTCACAGATGAATGCCGTGCATGTCAAGGAAATGCAC |
| SOR | ACCACAAGGAGCCGTCACGTATTGTCACAGATGAATGCCGTGCATGTCAAGGAAATGCAC |
| PQ434 | ACCACAAGGAGCCGTCACGTATTGTCACAGATGAATGCCGTGCATGTCAAGGAAATGCAC |
| 355 | ACCACAAGGAGCCGTCACGTATTGTCACAGATGAATGCCGTGCATGTCAAGGAAATGCAC |
| KF33 | ACCACAAGGAGCCGTCACGTATTGTCACAGATGAATGCCGTGCATGTCAAGGAAATGCAC |
| Tetron | ACCACAAGGAGCCGTCACGTATTGTCACAGATGAATGCCGTGCATGTCAAGGAAATGCAC |
| 1085 | ACCACAAGGAGCCGTCACGTATTGTCACAGATGAATGCCGTGCATGTCAAGGAAATGCAC |
| Ajabsido | ACCACAAGGAGCCGTCACGTATTGTCACAGATGAATGCCGTGCATGTCAAGGAAATGCAC |
| BTX623 | ACCACAAGGAGCCGTCACGTATTGTCACAGATGAATGCCGTGCATGTCAAGGAAATGCAC |
| BTX631 | ACCACAAGGAGCCGTCACGTATTGTCACAGATGAATGCCGTGCATGTCAAGGAAATGCAC |
| BTX642 | ACCACAAGGAGCCGTCACGTATTGTCACAGATGAATGCCGTGCATGTCAAGGAAATGCAC |
| IS39740 | ACCACAAGGAGCCGTCACGTATTGTCACAGATGAATGCCGTGCATGTCAAGGAAATGCAC |
| IS9830 | ACCACAAGGAGCCGTCACGTATTGTCACAGATGAATGCCGTGCATGTCAAGGAAATGCAC |
| J12731 | ACCACAAGGAGCCGTCACGTATTGTCACAGATGAATGCCGTGCATGTCAAGGAAATGCAC |
| Keller | ACCACAAGGAGCCGTCACGTATTGTCACAGATGAATGCCGTGCATGTCAAGGAAATGCAC |
| M35-1 | ACCACAAGGAGCCGTCACGTATTGTCACAGATGAATGCCGTGCATGTCAAGGAAATGCAC |
| Macia | ACCACAAGGAGCCGTCACGTATTGTCACAGATGAATGCCGTGCATGTCAAGGAAATGCAC |
| PI563516 | ACCACAAGGAGCCGTCACGTATTGTCACAGATGAATGCCGTGCATGTCAAGGAAATGCAC |
| Rio | ACCACAAGGAGCCGTCACGTATTGTCACAGATGAATGCCGTGCATGTCAAGGAAATGCAC |
| SC33 | ACCACAAGGAGCCGTCACGTATTGTCACAGATGAATGCCGTGCATGTCAAGGAAATGCAC |
| SC62 | ACCACAAGGAGCCGTCACGTATTGTCACAGATGAATGCCGTGCATGTCAAGGAAATGCAC |
| SC56 | ACCACAAGGAGCCGTCACGTATTGTCACAGATGAATGCCGTGCATGTCAAGGAAATGCAC |
| SC56 | ACCACAAGGAGCCGTCACGTATTGTCACAGATGAATGCCGTGCATGTCAAGGAAATGCAC |
| SC103 | ACCACAAGGAGCCGTCACGTATTGTCACAGATGAATGCCGTGCATGTCAAGGAAATGCAC |
| SC108C | ACCACAAGGAGCCGTCACGTATTGTCACAGATGAATGCCGTGCATGTCAAGGAAATGCAC |
| SC120 | ACCACAAGGAGCCGTCACGTATTGTCACAGATGAATGCCGTGCATGTCAAGGAAATGCAC |
| SC155 | ACCACAAGGAGCCGTCACGTATTGTCACAGATGAATGCCGTGCATGTCAAGGAAATGCAC |
| SC170 | ACCACAAGGAGCCGTCACGTATTGTCACAGATGAATGCCGTGCATGTCAAGGAAATGCAC |
| SC301 | ACCACAAGGAGCCGTCACGTATTGTCACAGATGAATGCCGTGCATGTCAAGGAAATGCAC |
| SC324 | ACCACAAGGAGCCGTCACGTATTGTCACAGATGAATGCCGTGCATGTCAAGGAAATGCAC |
| SC650 | ACCACAAGGAGCCGTCACGTATTGTCACAGATGAATGCCGTGCATGTCAAGGAAATGCAC |
| SC971 | ACCACAAGGAGCCGTCACGTATTGTCACAGATGAATGCCGTGCATGTCAAGGAAATGCAC |
| SC1103 | ACCACAAGGAGCCGTCACGTATTGTCACAGATGAATGCCGTGCATGTCAAGGAAATGCAC |
| SC039 | ACCACAAGGAGCCGTCACGTATTGTCACAGATGAATGCCGTGCATGTCAAGGAAATGCAC |
| TAM428 | ACCACAAGGAGCCGTCACGTATTGTCACAGATGAATGCCGTGCATGTCAAGGAAATGCAC |
| TX7000 | ACCACAAGGAGCCGTCACGTATTGTCACAGATGAATGCCGTGCATGTCAAGGAAATGCAC |
| | *********** ** * ***************** ******************** |

| | |
|---|---|
| PI585749 | AGACTAAGGATGCTGATGCCTAGAACTGCTTATGAAGAGATCTTTCAGAACTGAAGAT |
| PI586439 | AGACTAAGGATGCTGATGCCTAGAACTGCTTATGAAGAGATCTTTCAGAACTGAAGAT |
| KS115 | AGACTAAGGATGCTGATGCCTAGAACTGCTTATGAAGAGATCTTTCAGAACCAAAGAT |
| Greenleaf | AGACTAAGGATGCTGATGCCTAGAACTGCTTATGAAGAGATCTTTCAGAACTGAAGAT |
| BTX378 | AGACTAAGGATGCTGATGCCTAGAACTGCTTATGAAGAGATCTTTCAGAACTGAAGAT |
| SC35C | AGACTAAGGATGCTGATGCCTAGAACTGCTTATGAAGAGATCTTTCAGAACTGAAGAT |
| SC283 | AGACTAAGGATGCTGATGCCTAGAACTGCTTATGAAGAGATCTTTCAGAACTGAAGAT |
| PI525695 | AGACTAAGGATGCTGATGCCTAGAACTGCTTATGAAGAGATCTTTCAGAACTGAAGAT |
| A14 | AGACTAAGGATGCTGATGCCTAGAACTGCTTATGAAGAGATCTTTCAGAACCAAAGAT |
| SOR | AGACTAAGGATGCTGATGCCTAGAACTGCTTATGAAGAGATCTTTCAGAACCAAAGAC |
| PQ434 | AGACTAAGGATGCTGATGCCTAGAACTGCTTATGAAGAGATCTTTCAGAACCAAAGAC |
| 355 | AGACTAAGGATGCTGATGCCTAGAACTGCTTATGAAGAGATCTTTCAGAACCAAAGAC |
| KF33 | AGACTAAGGATGCTGATGCCTAGAACTGCTTATGAAGAGATCTTTCAGAACCAAAGAC |

| | |
|---|---|
| BTX378 | GATATTTATCCTCTTGAATCAGTATTTCATTAA |
| SC35C | GATATTTATCCTCTTGAATCAGTATTTCATTAA |
| SC283 | GATATTTATCCTCTTGAATCAGTATTTCATTAA |
| PI525695 | GATATTTATCCTCTTGAATCAGTATTTCATTAA |
| A14 | GATATTTATCCTCTTGAATCAGTATTTCATTAA |
| SQR | GATATTTATCCTCTTGAATCAGTATTTCATTAA |
| PQ434 | GATATTTATCCTCTTGAATCAGTATTTCATTAA |
| 555 | GATATTTATCCTCTTGAATCAGTATTTCATTAA |
| KF33 | GATATTTATCCTCTTGAATCAGTATTTCATTAA |
| Tetron | GATATTTATCCTCTTGAATCAGTATTTCATTAA |
| 1085 | GATATTTATCCTCTTGAATCAGTATTTCATTAA |
| Ajabsido | GATATTTATCCTCTTGAATCAGTATTTCATTAA |
| BTX623 | GATATTTATCCTCTTGAATCAGTATTTCATTAA |
| BTX631 | GATATTTATCCTCTTGAATCAGTATTTCATTAA |
| BTX642 | GATATTTATCCTCTTGAATCAGTATTTCATTAA |
| ICSV745 | GATATTTATCCTCTTGAATCAGTATTTCATTAA |
| IS9830 | GATATTTATCCTCTTGAATCAGTATTTCATTAA |
| J12731 | GATATTTATCCTCTTGAATCAGTATTTCATTAA |
| Keller | GATATTTATCCTCTTGAATCAGTATTTCATTAA |
| M35-1 | GATATTTATCCTCTTGAATCAGTATTTCATTAA |
| Macia | GATATTTATCCTCTTGAATCAGTATTTCATTAA |
| PI563516 | GATATTTATCCTCTTGAATCAGTATTTCATTAA |
| Rio | GATATTTATCCTCTTGAATCAGTATTTCATTAA |
| SC23 | GATATTTATCCTCTTGAATCAGTATTTCATTAA |
| SC52 | GATATTTATCCTCTTGAATCAGTATTTCATTAA |
| SC55 | GATATTTATCCTCTTGAATCAGTATTTCATTAA |
| SC56 | GATATTTATCCTCTTGAATCAGTATTTCATTAA |
| SC103 | GATATTTATCCTCTTGAATCAGTATTTCATTAA |
| SC108C | GATATTTATCCTCTTGAATCAGTATTTCATTAA |
| SC110 | GATATTTATCCTCTTGAATCAGTATTTCATTAA |
| SC155 | GATATTTATCCTCTTGAATCAGTATTTCATTAA |
| SC170 | GATATTTATCCTCTTGAATCAGTATTTCATTAA |
| SC301 | GATATTTATCCTCTTGAATCAGTATTTCATTAA |
| SC326 | GATATTTATCCTCTTGAATCAGTATTTCATTAA |
| SC650 | GATATTTATCCTCTTGAATCAGTATTTCATTAA |
| SC971 | GATATTTATCCTCTTGAATCAGTATTTCATTAA |
| SC1103 | GATATTTATCCTCTTGAATCAGTATTTCATTAA |
| SRN39 | GATATTTATCCTCTTGAATCAGTATTTCATTAA |
| TAM428 | GATATTTATCCTCTTGAATCAGTATTTCATTAA |
| TX7000 | GATATTTATCCTCTTGAATCAGTATTTCATTAA |
| | ************************* ******* |

The two MITEs are distantly related

```
5primeMITE    GGGATGAAAACAGTACGGATATTTTCCGACCGTATTCGAGACCGAATTCGTTTAGAGGGG
3primeMITE    ---------------AGGCCTTGTTTAGTTCACCTTGAAAACCAAA-AAGTTTTCAAGAT
                              **   * **   *   *    **   *  *** **   ****   *  *

5primeMITE    TTTAAATCTGTCCGTATCCGA--GTCCGAATATTCAACATCCGATACCGTATCCGTATCC
3primeMITE    TCCCTGTCACATCGAATTTTGTGGCACATGCATGAAATATTAAATATAGACGAAAACAAA
                *     **     ** **       *   *       **   **  **     ***    *

5primeMITE    GAATACTTAAATCGTATATTTGTGATGTCGACCTCCAATCATATCTTATCCGACATAGTT
3primeMITE    AACTAATTACACAGTT-----TAGCTGTAAATCACGAGACGAATCTTTTGATCCTAGTTA
               *  **  ***  *   **              *  ***  *  *  *   *  *****  *     *      *

5primeMITE    GACATTATCCGTATTCGAATCCGAATTCGACCAAAAATATGAAAACAAATATGATATCAG
3primeMITE    G------TCCATGATTGGATAATATTTGTCACAAACAAACGAA-AGTGCTACAGTATCGA
              *       *** *    *    * **    *  **        ****   *  * ***   *      **    ****

5primeMITE    --------TGATATTCGTCCGTATCCGATCCGTTTTCATCCC
3primeMITE    AAACTTTTCACTTTTCGGAACTAAACAAGCCTT---------
                       *  ****    **   *  *  **   *
```

| Genotype | Rust score | Phenotype |
|---|---|---|
| SC283 | $F^b$ | Resistant |
| SSD1 | 1 | Resistant |
| SSD3 | 1 | Resistant |
| SSD4 | $F^b$ | Resistant |
| SC35 | 1 | Resistant |
| BTX378 | 1 | Resistant |
| Green leaf | 1 | Resistant |
| TAM428 | 3 | Susceptible |
| BTX623 | 2 | Susceptible |
| SQR | 2 | Susceptible |
| MACIA | 2 | Susceptible |
| SSD50 | 2 | Susceptible |
| SSD61 | 2 | Susceptible |
| SSD65 | ?? $F^b$ | Resistant |

FIGURE 23

```
ARG1_SC283    MGSVLFSLSSKCLDKLAVLLEEEVMMTLSVRKDIRKLHDYLKYFNSIREDADARAMEHRE
ARG1_TAM428   MGSVLFSLSSKCLDKLAVLLEEEIMMTLSVRKEIRKLHDYLKYFDSIHEDADARAMEHRE
              ***********************:*******:************:**.************

ARG1_SC283    TTGIWWGDVKDVMYDVDDIIDLLRAHSQKQRCCDLRMLSRFAQLQFDHMIARKIKGVNER
ARG1_TAM428   MTGIWWGDVKDVMYDVDDIIDLLRAHSQKQRCCDLRMLSRFAQLQFDHMIARKIKGVNER
              .***********************************************************

ARG1_SC283    LVEIQKNRDMFLPPGLYPQAQAPQTNRVDSRHLAASVDEIHVVGAEIKEATDSMVEMIVG
ARG1_TAM428   LVEIQKNRDMFLPPGLYPQAQAPQTNGVDSRHLAASVDEIHVVGAEIKEATDSMVEMIVG
              ************************** *********************************

ARG1_SC283    YGHQSRISVYGIVGMGGIGKTTLAQKIYNDRRIRERFHQVLIWLSISQSIAENDLLKEAI
ARG1_TAM428   YGHQSRISVYGIVGMGGIGKTTLAQKIYNDRRIRERFHQVLIWLSISQSIAENDLLKEAI
              ************************************************************

ARG1_SC283    EKAGGQCNQHKSKDQLVQILLHSISGKSVFLVLDNVTNPDVWIDLLRSPMERCLDAHVLV
ARG1_TAM428   EKAGGQCNQHKSKDQLVQILLHSISGKSVFLVLDNVTNPDVWIDLLRSPMERCLDAHVLV
              ************************************************************

ARG1_SC283    TTRSGHVLSQMNAVHVKEMHRLKDADGLELLMKRSFRTEDEVNVFSDIGAKIVKKCDGLP
ARG1_TAM428   TTRSGHVLSQMNAVHVKEMHRLKDADGLELLMKRSFRTKDEVNVFSDIGAKIVKKCDGLP
              **************************************:*********************

ARG1_SC283    LAIKVIGGVLSSRSSKEEWERILERRWSIDGLPEELEGALYLSYSDLHPQLKQCFLWCAL
ARG1_TAM428   LAIKVIGGVLSSRSSKEEWERILERRWSIDGLPEELEGALYLSYSDLHPQLKQCFLCCAL
              ********************************************************  ***

ARG1_SC283    LPQNFDIHRDVTYWWIAEGLVKEETSGPIHNVAEDYYHELIKRNLLQARPEYVDKGISIM
ARG1_TAM428   LPQNFDIHRDVTYWWIAEGFVKEEGSGPIHNIAEDYYHELIKRNLLQARPEYVDKGVSTM
              *******************.****.******:***********************.* *

ARG1_SC283    HDLLRQLGQFLTRNEAVFMNEKRDRCPSSIRRLGVGSAVDEIPSIEEKKRLRCLIVLDHD
ARG1_TAM428   HDLLRQLGQFLKRNEAIFMNEKRERCL--SIRRLGVGSAVDEIPSIEEKKRLRCLIVLHHD
              ***********.****:******:**    ***************************  **

ARG1_SC283    TCRSVKRDIFRKLVHLRILVLRGAGLESIPASVGYLALLRLLDLSYNEIKELPGSIGNLT
ARG1_TAM428   TCRSVKRDIFRKLVHLRILVLRGAGLESIPASVGYLALLRLLDLSYNEIKELPGSIGNLT
              ************************************************************

ARG1_SC283    SLGCLSVFGCTKLAALPQSLMRLTTISFLQIGNTGLAQVPKGIENFRQIDNLRSVFQNGT
ARG1_TAM428   SLGCLSVFGCTKLAALPTSLMRLTTISFLKIGNTGLAQVPKGIENFKQMDNLRSVFQNGT
              *****************.***********:***************.*:************

ARG1_SC283    DGFRLDELRALSMIRRLWVIRLETATPPTEPVLCDKGYLKELGLRCTMGKEANCRTHYPD
ARG1_TAM428   DGFRLDELRALSMIRRLWVIRLETAIPPTEPILCDKGYLKELGLRCTMGKEANCRTHYPD
              *************************.*****:****************************

ARG1_SC283    SKVKRIEEIYESFCPPPSLSYVFIDGFPGRMFPTWLSLEPQNKLPNLAHMHFYDCISCPK
ARG1_TAM428   SKVKRIEEIYESFCPPPSLSYVFIDGFPGCMFPTWLSSEPQNKLPNLAHMHFNDCISCPK
              *****************************.******* **************:*******

ARG1_SC283    LPPAGQLPFLQVLHVKGADAVVNIGAELLGNGIPSGTHTTAFPKLELLEILDMYNWQNWS
ARG1_TAM428   LPPAGQLPFLQVLHVKGADAVVNIGAELLGNSIPSGTHTTAFPKLELLEILDMYNWQNWS
              *******************************.****************************

ARG1_SC283    LSMDTLFENTQQQFLMPCLTRLRLINCFKLRALPDHLHRVVNLQRIQIEGADSLQEVVNH
ARG1_TAM428   LSMDTLFEKTQQQSLMPCLTRLRLINCPKLRALPDHLHRVVNLQRIQIEGADSLQEIVNH
              ********.****. ***********.*****************************:***
```

FIGURE 23 Cont'd

```
ARG1_SC283      PGVVWLKVKNNKSLRNISNLPKLRLLLAQDCQELQQAENLSSLKALYVVDCPMEQILWKC
ARG1_TAM428     PGVVWLKVKNNKSLRNISNLPKLRLLLAQDCQELQQAENLSSLKALYVVDCPMEQILWKC
                ************************************************************

ARG1_SC283      FPIEQQSTIVRVVTTGAHGQDIYPLESVFH
ARG1_TAM428     FPIEQQSTIVRVVTTGAHGQDIYPLESVFH
                ******************************
```

IMMUNE RECEPTOR CONFERRING BROAD SPECTRUM FUNGAL RESISTANCE IN SORGHUM

PRIORITY

The present application is related to, claims the priority benefit of, and is a 35 U.S.C. 371 national stage application of International Patent Application Serial No. PCT/US2018/062172, filed Nov. 21, 2018, which is related to and claims the priority benefits of U.S. Provisional Application Serial No. 62/589,295, filed on Nov. 21, 2017. The entire content of each of the aforementioned priority applications is expressly incorporated herein by reference in their entireties.

GOVERNMENT RIGHTS

This invention was made in part with government support under AID-OAA-A-13-00047 awarded by USAID. The government has certain rights in the invention.

FIELD OF INVENTION

This disclosure provides a unique molecular marker in sorghum genome chromosome 7 for a gene that confers a broad range of fungal resistance trait, and the use of the molecular marker to manipulate resistance in sorghum. Particularly, a disease resistance gene called ANTHRACNOSE RESISTANCE GENE 1 (ARG1) and a negative regulator, i.e. antisense transcripts of ARG1, called CARRIER OF ARG (CARG) for the fungi resistance gene are knocked out within this quantitative trait locus (QTL).

BACKGROUND

Fungal disease are major challenges to crop production. Anthracnose is the leading global disease of sorghum. It is caused by the fungal pathogen *Colletotrichum sublineolum*.

To fend off pathogen infection, plants have evolved immune systems that are effective in either restricting infection or inhibiting the progress of disease symptoms. The two primary branches of the plant immune system are PAMP Triggered Immunity (PTI) and Effector Triggered Immunity (ETI). PTI is a form of disease resistance initiated upon recognition of pathogen associated molecular patterns (PAMPs) by plasma membrane-anchored pattern recognition receptors (PRRs) located on the surface of plant cell membranes. Perception of PAMPs by PRRs activates a battery of immune responses, including the production of antimicrobial defense compounds, pathogenesis related proteins and accumulation of reactive oxygen species. This form of resistance is quantitative and often independent of the strain of the pathogen. Plant pathogens suppress PTI by deploying specific virulence effectors that interfere with PTI. In response, plants have evolved ETI, which is based on recognition of effectors by structurally related but polymorphic intracellular immune receptors known as nucleotide-binding site leucine-rich repeat receptors (NLRs). The core of NLRs is the nucleotide-binding (NB) and leucine-rich repeat (LRR) domains with N-terminal coiled-coil (CC) or Toll/interleukin-1 receptor (TIR) domains. ETI activates stronger plant immune responses that confer resistance to strains of the pathogen that express particular effectors. The strong selective pressure on pathogens imposed by ETI results in frequent defeat of resistance by pathogens that acquire new virulence effectors and thus escape recognition by NLRs. Recent observations suggest that PTI and ETI represent a continuum of overlapping responses rather than being categorical[1].

Natural antisense transcripts (NATs) are non-coding RNAs widely known to regulate gene expression in animal and plant cells through several mechanisms[2]. Transcription interference between the expression of protein-coding sense transcripts and the corresponding NAT[3,4], chromatin modification[5], RNA interference, and DNA methylation have all been implicated in regulating expression of the sense transcripts[6-8]. In plants, NATs regulate phosphate homeostasis in rice[9], cell wall biosynthesis in barley[10] cytokinin regulation in petunia[11], salt tolerance and fertilization in Arabidopsis[12], fiber development in cotton[13] and drought tolerance in maize[14].

Sorghum is an important food crop but also serves as a source of animal feed, biofuel, and other industrial products. Sorghum anthracnose, caused by the fungal pathogen *Colletotrichum sublineolum* (Cs), is the most devastating foliar disease of this crop[15]. Although anthracnose resistant germplasm is available, the specific resistance regulators and their mechanisms of function have not been determined. There is a need to identify these fungal resistance mechanisms sorghum plants use and exploit such mechanisms to generate broad spectrum resistance in the plant.

SUMMARY OF THE INVENTION

This disclosure provides an isolated polynucleotide comprising of SEQ ID NO:1 (ARG1) that confers sorghum broad spectrum resistance to fungi, wherein the polynucleotide is reversely embedded in SEQ ID NO: 2 (CARG).

This disclosure also provides primers to genotype molecular markers within sorghum genome to diagnose whether the sorghum has broad-spectrum fungal resistance trait. The primers for such diagnosis comprising sequences selected from the group of SEQ ID Nos:3-4, SEQ ID Nos: 5-6 and SEQ ID NO:9-10.

In some preferred embodiment, the aforementioned molecular marker is CARG with or without deletions of GGCGACCT.

In some preferred embodiment, the aforementioned the molecular marker is ARG1 with or without a premature stop codon.

This disclosure further provides a pair of primers to generate an expression cassette of antifungal ARG1 within sorghum genome, such primers comprising SEQ ID Nos: 7-8.

This disclosure further provides a method of generating a transgenic sorghum plant with broad resistance to fungi infection. The method comprising genetically transforming a susceptible sorghum genotype with the isolated polynucleotide of SEQ ID NO:1.

This disclosure provides a plant cell comprising the polynucleotide of SEQ ID NO:1.

In some preferred embodiment, the aforementioned plant is a monocot.

In some preferred embodiment, the aforementioned plant is wheat, barley, rice, maize, sorghum, oats, rye or millet.

This disclosure further provides a method of genotyping a plant. The method comprising using the pair of primers selected from the group consisting of SEQ ID NOs:3-4, SEQ ID Nos: 5-6 and SEQ ID NO:9-10.

In some preferred embodiment the aforementioned genotyping method uses primers generating a polymorphism fragment in PCR product that differentiates fungal infection susceptible versus resistant sorghum.

These and other features, aspects and advantages of the present invention will become better understood with reference to the following figures, associated descriptions and claims.

Plants were scored as resistant or susceptible based on their disease symptom or resistance response phenotypes. The DNAs from resistant or susceptible plants were bulked to make separate resistant (R) and susceptible (S) DNA bulks. S-bulk, DNA from the susceptible plants, R-bulk, DNA from the resistant plants. SNP index and Δ (SNP-index) was determined as described.

Figures 2A, 2B, 2C, 2D:
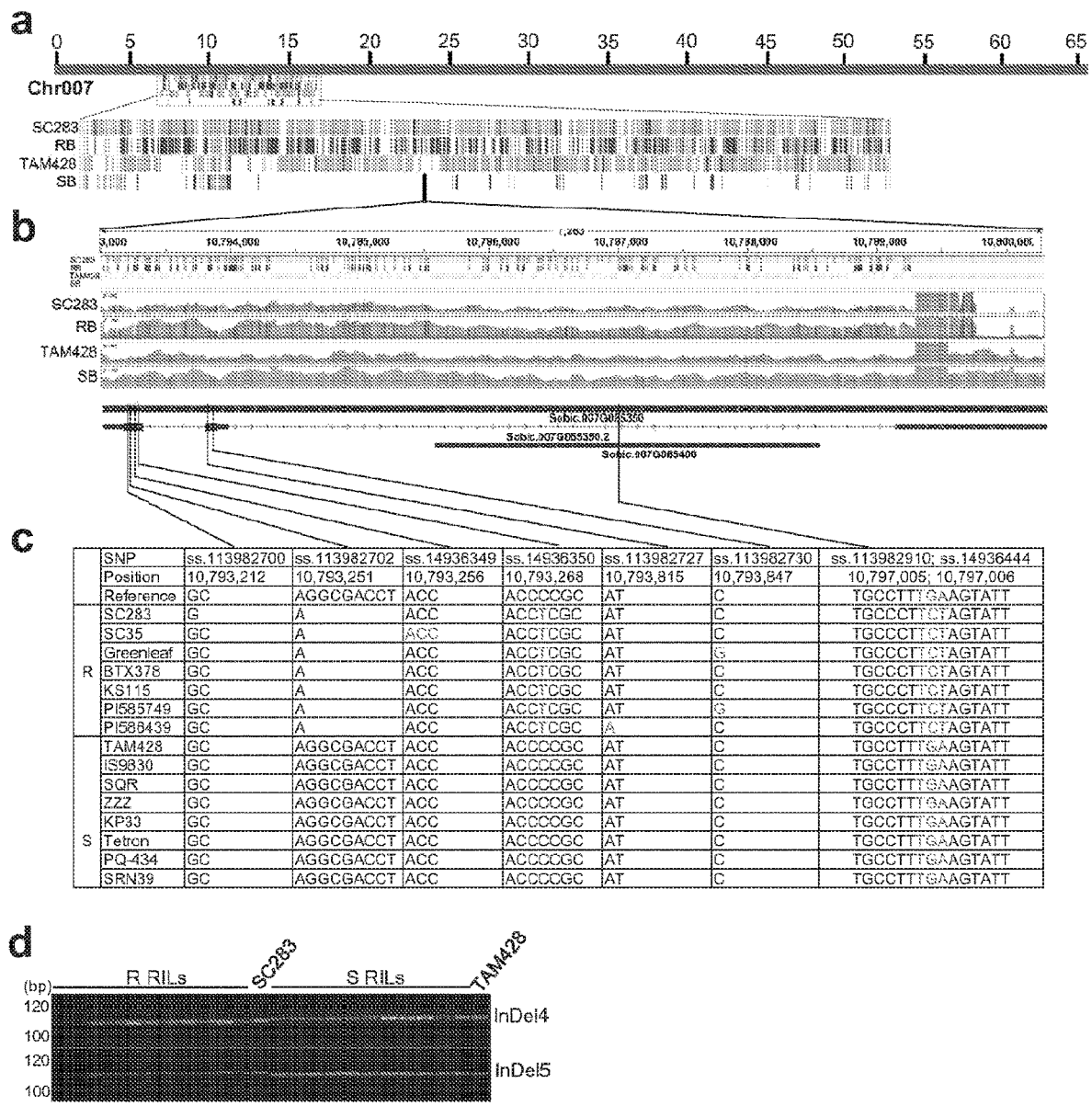

FIG. 2. Sequence comparisons in resistance QTL region identifies the ARG1 locus. (FIG. 2A) *C. sublineolum* resistance QTL was mapped to Chromosome 7 (7.15 MB to 15.80 Mb) based on QTL-seq.

(FIG. 2B) Comparisons of DNA sequence reads from resistant, susceptible and the parental lines SC283 and TAM428. The DNA-sequences were compared with the reference genome BTX623 and SNPs were marked as blue bars. The sequences from susceptible bulk (SB) and TAM428 show no sequence polymorphism relative to the reference genome in the QTL region. Sequences of Sobic.007G085350 from the resistant DNA pools (R-bulks) and SC283 are different from the susceptible DNA pools (S-bulks) and TAM428. The sequence of the resistant pool is identical to the SC283 in the QTL region.

(FIG. 2C) Genomic structure of the resistance locus showing Sobic.007G085350 and the nested genes Sobic.007G085400 based on the annotation of the reference genome and Phytozome V10; Sbicolor 313 V3.1. The whole genome sequences available in various databases were searched for sequence polymorphisms in the QTL region to identify additional alleles in genes of interest. The table in the lower panel shows sequence comparisons between different allelic variants of Sobic.007G085350 (portions of SEQ ID NO: 1 (SC283), SEQ ID NO: 28 (P1585749 and P1586439), SEQ ID NO: 29 (KS115), SEQ ID NO: 30 (Greenleaf), SEQ ID NO: 31 (BTX378 and SC35), SEQ ID NO: 35 (SQR), SEQ ID NO: 36 (PQ-434), SEQ ID NO: 37 (KP33 and Tetron), SEQ ID NO: 38 (IS9830, SRN39, and TAM428), SEQ ID NO: 41 (ZZZ)). The coding and genomic region with introns are based on predictions in the database (Phytozome V10; Sbicolor 313 V3.1).

(FIG. 2D) Genotyping of the resistant and susceptible recombinant inbred lines using Indel markers in Sobic.007G085350 gene. InDel4 and InDel5, represent two deletion polymorphisms which were used to design PCR markers in the Sobic.007G085350 gene and are polymorphic between SC283 and TAM428.

R RILs, resistant recombinant inbred lines; S RILs, susceptible recombinant inbred lines.

FIG. 3. Sequence polymorphism in the CARG-ARG1 locus co-segregate with the fungal resistance phenotypes.

(FIG. 3A and FIG. 3B) Genotyping of the resistant and susceptible recombinant inbred lines (FIG. 3A) and distinct sorghum lines (FIG. 3B) using Indel markers in Sobic.007G085350 gene. InDel4 and InDel5, represent two deletion polymorphisms which were used to design PCR markers in the Sobic.007G085350 gene and are polymorphic between resistant lines and susceptible lines.

(FIG. 3C and FIG. 3D) Disease symptoms in sorghum lines carrying CARG and ARG1 alleles after inoculation with Cs strain Cgsl2. SSD1, SSD3 and SSD4 are resistant RILs while SSD50, SSD61 and SSD65 are susceptible RILs. SC283, BTX378, KS115, SC35, PI585749, PI586439, and Greenleaf are resistant genotypes that carry the deletion in the CARG. TAM428, BTX623, Tetron, SQR, PQ434, KP33, ZZZ, IS9830, 555 and SRN39 are susceptible genotypes that have intact CARG gene.

Figures 3A, 3B, 3C, 3D, 3E:
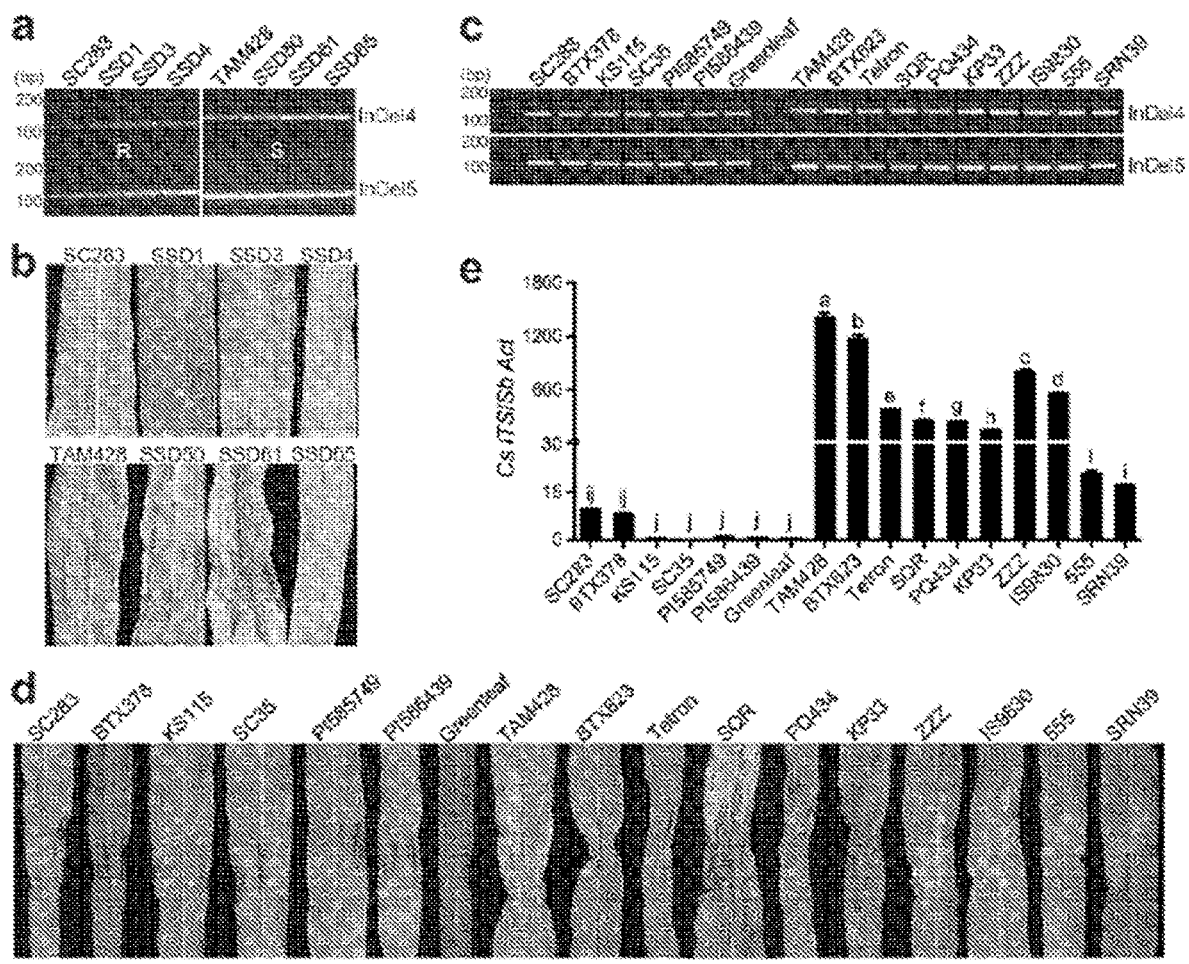

FIG. 3E shows data relating to the quantification of fungal growth in Cs inoculated sorghum lines carrying CARG and ARG1 alleles. The fungal growth in infected leaves was determined by qPCR amplification of the Cs ITS DNA (Cs ITS). Relative DNA levels were calculated using SbActin (Sb Act) as reference gene. Data represent mean±SD from three technical replicates. Letters indicate statistically significant differences. (P<0.05, Student's t test).

FIG. 4. RNA-seq analysis reveals basal and induced expression of ARG1 and CARG genes and the structure of the resistance locus.

Figures 4A, 4B, 4C, 4D, 4E:
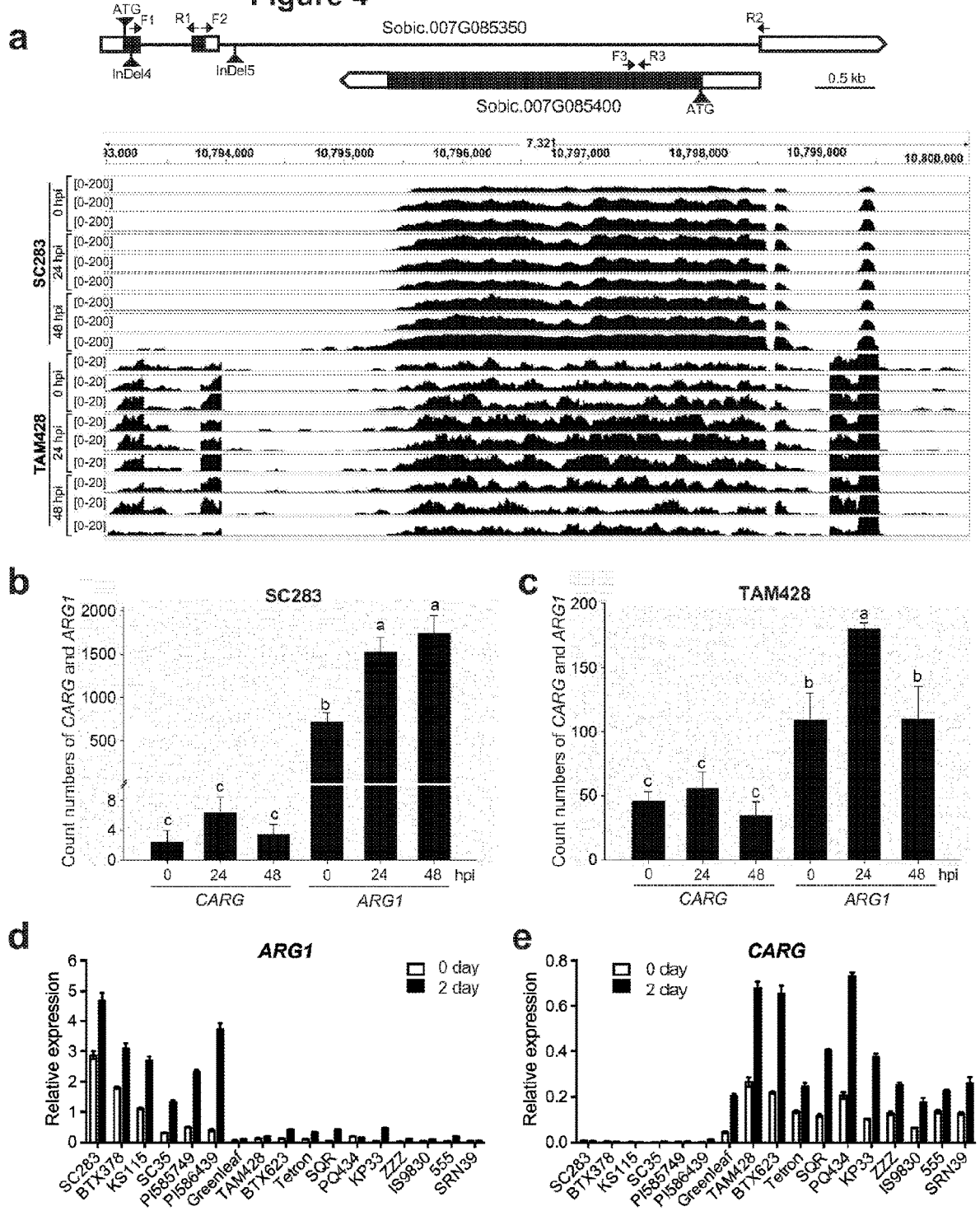

(FIG. 4A) Genomic structure of the ARG1-CARG locus deduced from the qRT-PCR, RNA-seq and genomic sequence data, (FIG. 4B) RNA-seq analysis of the ARG1-CARG locus. RNA-seq was conducted at 0, 24 and 48 h after inoculation with *C. sublineolum*. Sequence reads are viewed by integrative genomic viewer (IGV) and mapped to the reference genome. The transcript count data are shown at 0-200 scale for SC283 and 0-20 scale for TAM428 due to the elevated levels of the transcripts for ARG1 in SC283. The mapped transcripts were used to determine the exon, introns, and UTR regions of the CARG and ARG1 genes shown in the upper panel in (FIG. 4A).

(FIG. 4B and FIG. 4C) Expression of ARG1 and CARG genes in (FIG. 4B) SC283 and (FIG. 4C) TAM428 based on RNA-seq transcript count data. Error bars indicate the standard deviation of three libraries. Error bars±SD (n=3). Letters indicate significant difference based on the Least Significant Difference (LSD, P<0.05).

(FIG. 4D) ARG1 and (FIG. 4E) CARG expressions in different sorghum lines. In (FIG. 4D) and (FIG. 4E), expression levels were analyzed by qRT-PCR in independent sorghum genotypes at 0 and 2 days after Cs inoculation. Data are normalized by the comparative cycle threshold method with Actin as the internal control and presented as relative expression. The data represent mean±SD from three technical replicates of two independent biological replicates (n=6). Similar results were obtained in two independent experiments.

Figures 5, 5A, 5B, 5C:
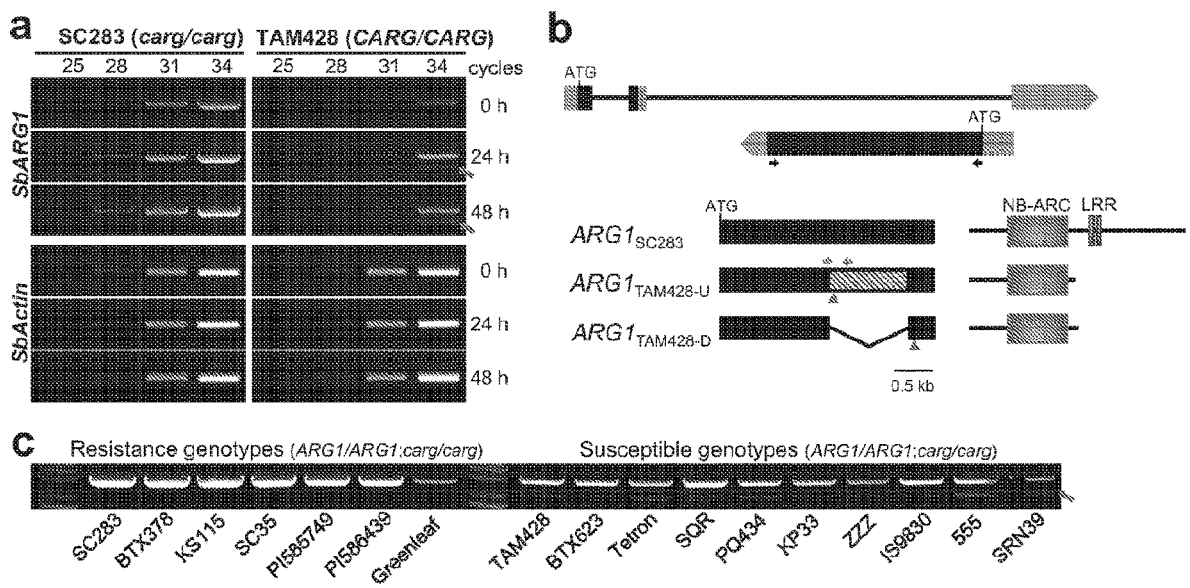

FIG. 5. ARG1 allele in susceptible genotypes produces two transcripts.

(FIG. 5A) Semi-quantitative RT-PCR showing the expression of ARG1 on SC283 and TAM428. The spliced ARG1 variant is indicated by red arrow. Actin shows equal amount of cDNA input. Similar results were obtained in two independent experiments.

(FIG. 5B) A schematic drawing of CARG and ARG1 genes (top panel). Exon and UTR regions are shown as black and gray bars, respectively. ATG indicates translational start site and black arrows indicate the position of primers used to amplify ARG1 transcripts.
The full-length and alternative spliced ARG1 transcripts are shown schematically together with red triangles indicated positions of stop codon in the full-length and spliced ARG1 transcripts and TAM428. The skipped exon in the spliced second variant transcript is represented by diagonal pattern in the exon. The major domains in ARG1 proteins present in the bottom right side. NB-ARC, nucleotide binding site; LRR, leucine-rich repeat domain.

(FIG. 5C) RT-PCR showing the ARG1 transcripts observed in independent sorghum lines. The spliced ARG1 variant is indicated by red arrow. Similar results were obtained in two independent experiments.

FIG. 6. The promoters of CARG and ARG1 genes regulate the gene expression via MITEs.

(FIG. 6A) Small RNA profiling of SC283 and TAM328 identifies small RNAs derived from the overlapping ARG1 5'-UTR and CARG 3'-UTR. The alignment shows the newly identified small RNA sequence (SEQ ID NO: 26) and a previously described Sbi-miR6225 small RNA (SEQ ID NO: 25).

(FIG. 6B) Small RNA count numbers based on small RNA-seq data.

Error bars indicate the standard deviation of three libraries. Error bars±SD (n=3). Letters indicate significant difference based on the Least Significant Difference (LSD, $P<0.05$).

(FIG. 6C) MITE insertions in the CARG-ARG1 locus (middle panel). The promoter and UTR regions are in white; the CARG exons are in grey; the introns are in white with diagonals; the ARG1 exon in the second intron of CARG1 is in black; the yellow, purple, green, and red boxes indicate 275-, 151-, 248-, and 420 bp MITEs, respectively. The CARG (left panel) and ARG1 (right panel) transcript levels quantified by qRT-PCR. Data are normalized by the comparative cycle threshold method with Actin as the internal control and presented as relative expression. The data in the both panels represent the means±SD, n=9.

FIG. 7. ARG1 and CARG genes show contrasting gene expression and inheritance.

(FIG. 7A) ARG1 and (FIG. 7B) CARG expressions in SC283, TAM428 and F2 plants. In (FIG. 7A) and (FIG. 7B), expression levels were analyzed by qRT-PCR in SC283, TAM428 and F2 plants. Data are normalized by the comparative cycle threshold method with Actin as the internal control and presented as relative expression. The data represent at least four biological repeats with three technical replicates. Error bars show ±SD (n≥24). Different letters indicate significant differences among genotypes ($P<0.05$, Student's t test). Similar results were obtained in three independent experiments.

(FIG. 7C) Disease response phenotypes of CARG and ARG1 genotypes.

(FIG. 7D) Area of disease lesions and, (FIG. 7E) quantification of fungal growth. In (FIG. 7D), the ratio of lesion area (%) are presented as mean±SD obtained from five inoculated leaves. Letters indicate statistically significant differences ($P<0.05$, Student's t test). In (FIG. 7E), fungal growth in infected leaves was determined by qPCR amplification of the Cs ITS DNA (Cs ITS). Relative DNA levels were calculated using SbActin (Sb Act) as reference gene. Data represent mean±SD from three technical replicates. Letters indicate statistically significant differences. ($P<0.05$, Student's t test).

Figures 8, 8A, 8B, 8C, 8D:
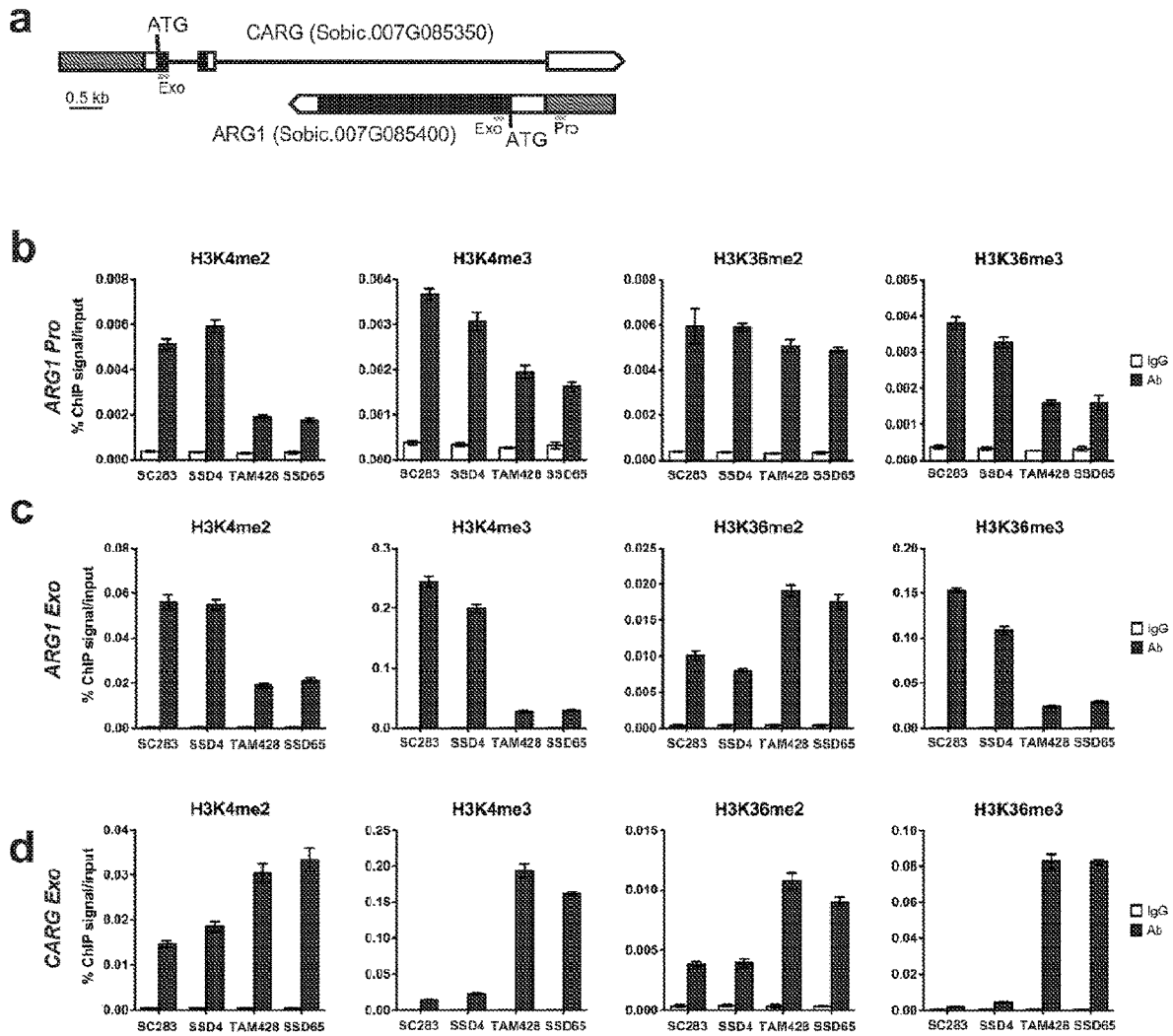

FIG. 8. H3K4 and H3K36 di- and trimethylation at ARG1 and CARG loci.

(FIG. 8A) Schematics showing the CARG and ARG1 genomic region. The location of the primers at the promoter (Pro) and coding regions (Exo) used to analyze the level of H3K4 and H3K36 methylation by chromatin immunoprecipitation (ChIP) assays are indicated by bars. The gray, white and black boxes indicate promoters, UTRs and exons respectively.

(FIG. 8B and FIG. 8C) Relative enrichment levels of H3K4me2/3 and H3K36me2/3 at chromatin of ARG1 exon (FIG. 8B) and promoter (FIG. 8C) regions. (FIG. 8D) Relative enrichment levels of H3K4me2/3 and H3K36me2/3 at chromatin of CARG exon region. ChIP was conducted on chromatin extracts with antibodies that recognize different histone methylations and IgG was used as a background control. Data from each experiment were normalized to sorghum Actin (Sobic.001G112600) gene and are presented as percentage of IP/input. Error bars indicate the standard deviation of three technical replicates. Two independent experiments were performed with similar results. Ab, Antibody. SSD4 and SSD65 are resistant and susceptible recombinant inbred lines, respectively.

FIG. 9. H3K9 di- and trimethylation at ARG1 and CARG loci.

(FIG. 9A) Schematics showing the genomic region of CARG and ARG1. The location of primers at the promoter (Pro) and coding regions (Exo) that were used to analyze the level of H3K36 methylations by ChIP assays are shown. The gray, white and black boxes indicate promoters, UTRs and exons respectively.

(FIG. 9B and FIG. 9C) Relative enrichment levels of H3K9me2 and H3K9me3 on ARG1 promoter (FIG. 9B) and exon (FIG. 9C) regions. (FIG. 9D) Relative enrichment levels of H3K9me2 and H3K9me3 at the CARG exon region. ChIP was performed on chromatin extracts using antibodies that recognize different histone methylations as indicated, and IgG serves as a background level. Data from each experiment were normalized to sorghum Actin (Sobic.001G112600) gene and values are presented as the percentage of IP/input. Error bars indicate the standard deviation of three technical replicates. Two independent experiments were performed with similar results. Ab, Antibody. SSD4 and SSD65 are resistant and susceptible recombinant inbred lines, respectively.

Figure 10:
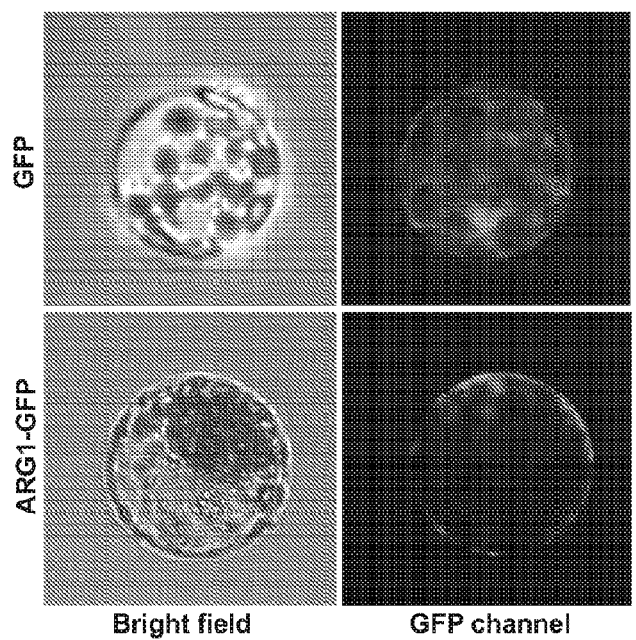

FIG. 10. AGR1-GFP is localized to the plasma membrane. Subcellular localization of ARG1-GFP analysis. A plasmid expressing ARG1-GFP fusion under the control of the CaMV 35S promoter was transfected into Arabidopsis protoplasts. The fluorescence signals were observed by epifluorescence microscopy.

FIG. 11. SNP-index and Δ (SNP-index) plots for 10 chromosomes of sorghum bulked DNA. (FIG. 11A) The SNP density for bulked DNA of the RILs. (FIG. 11B) The SNP depth for bulked DNA of the RILs. (FIG. 11C) The SNP-index of resistant bulk. (FIG. 11D) The SNP-index of susceptible bulk. (FIG. 11E) The Δ (SNP-index) plot obtained by subtraction of S-bulk SNP-index from R-bulk SNP-index for RILs. Statistical confidence intervals under the null hypothesis of no QTL are shown (orange: P<0.1; green<P<0.05). Single nucleotide polymorphism (SNP)-index plots of R-bulk and S-bulk, and Δ (SNP-index) plot of all sorghum chromosomes. The Δ (SNP-index) plot was obtained by subtraction of S-bulk SNP-index from R-bulk SNP-index for RILs. The DNAs from resistant or susceptible plants were bulked to make separate resistant (R) and susceptible (S) DNA bulks. S-bulk, DNA from the susceptible plants, R-bulk, DNA from the resistant plants. SNP index and Δ (SNP-index) was determined as described.

Figure 12:
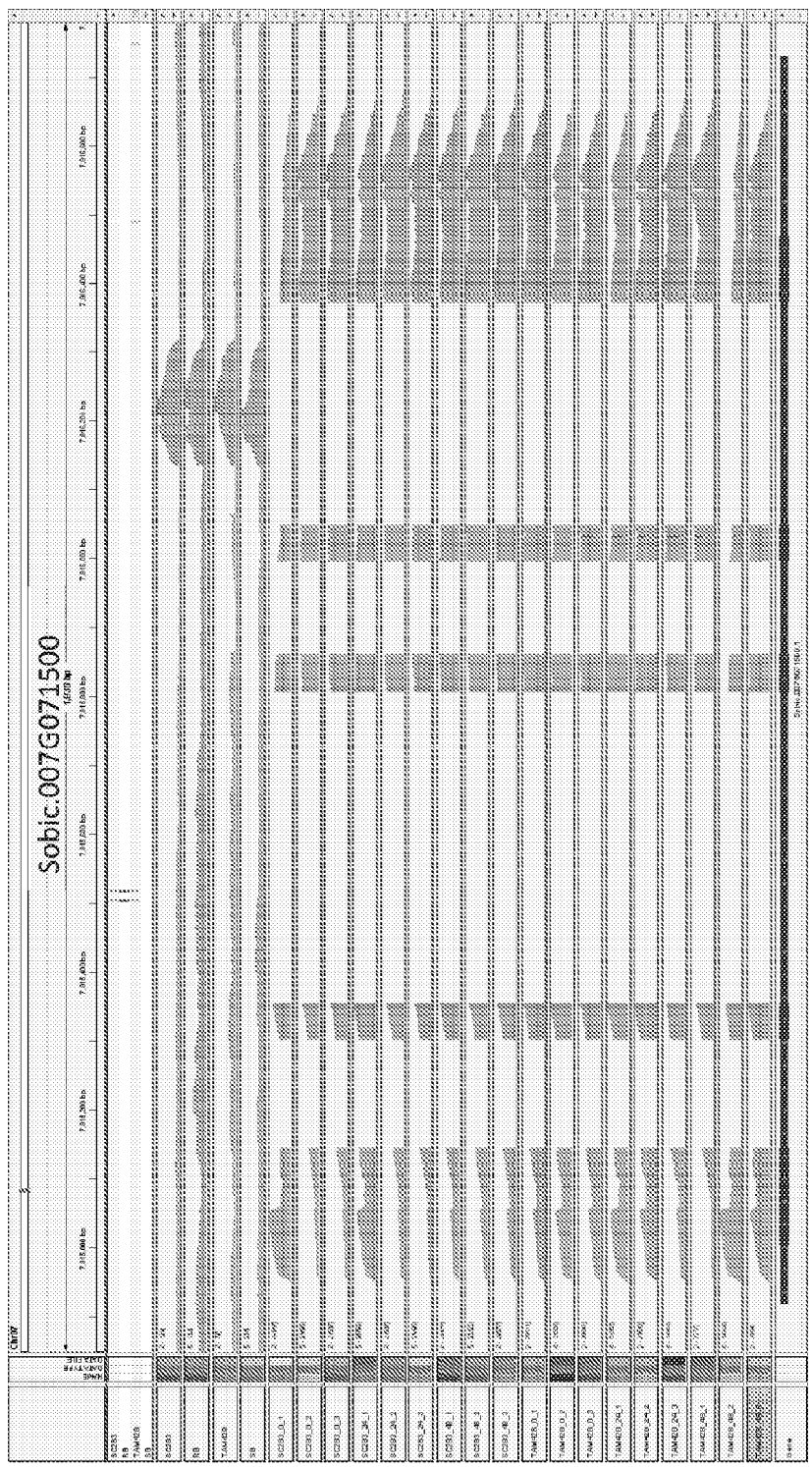
Figure 12:
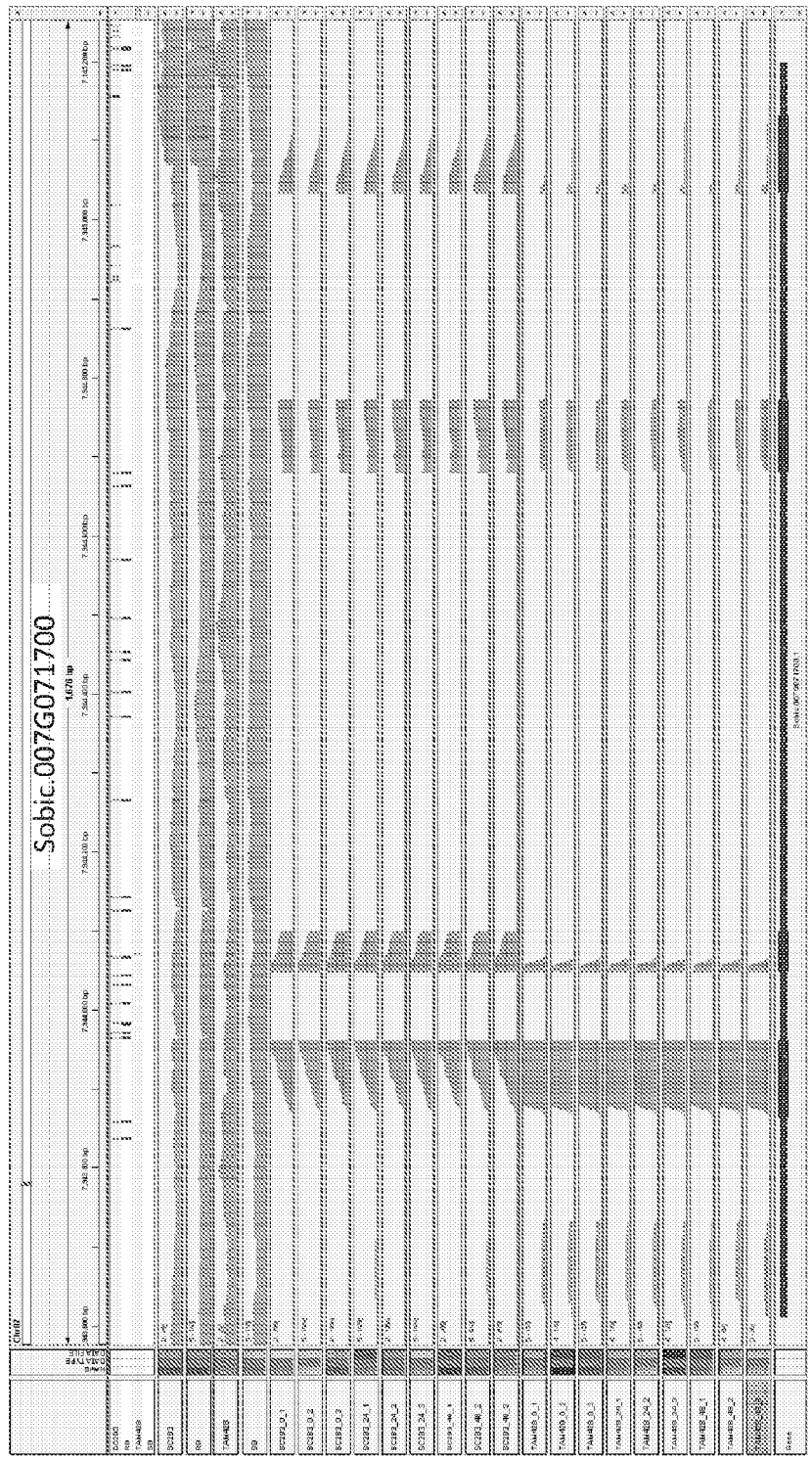
Figure 12:
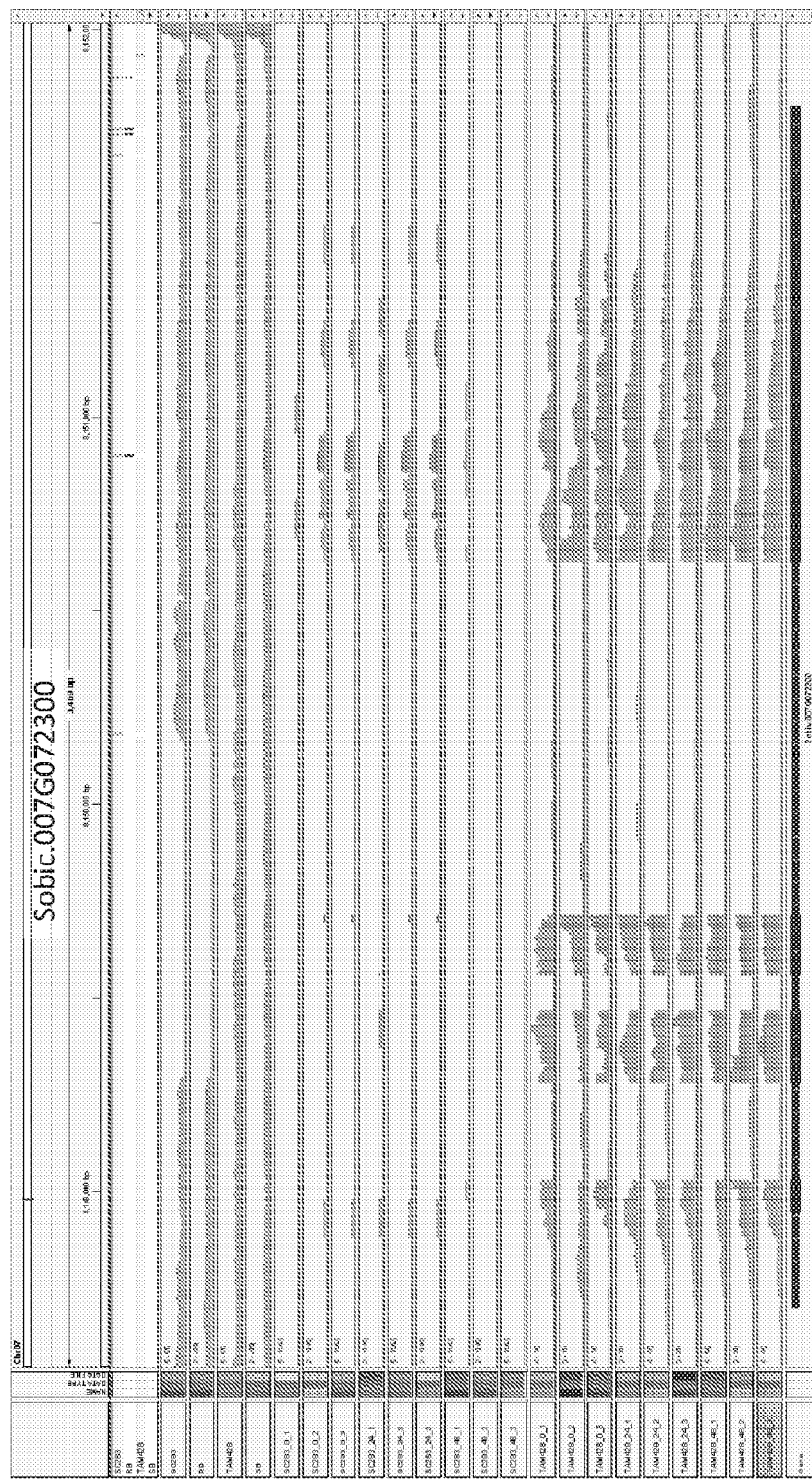
Figure 12:
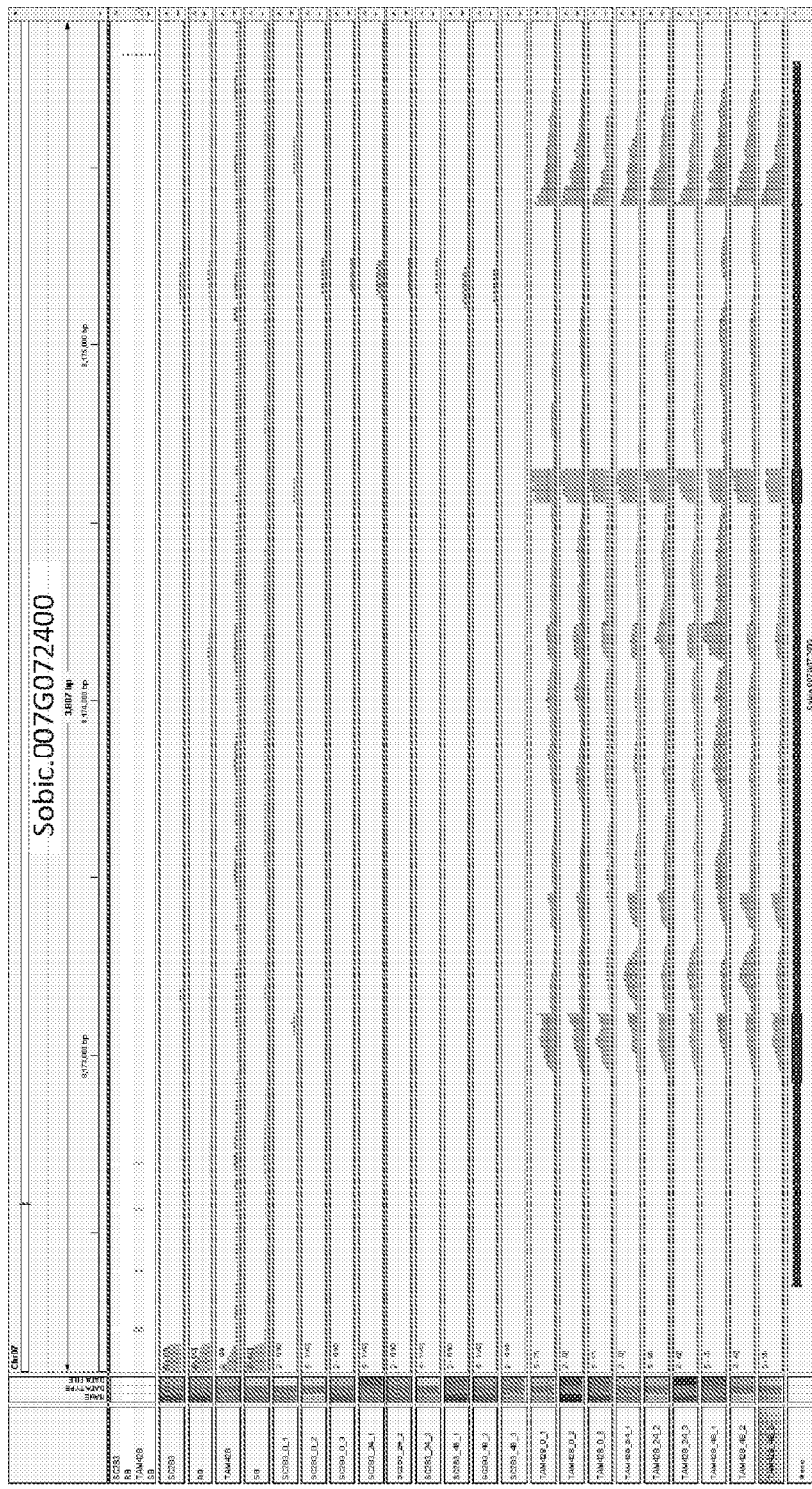
Figure 12:
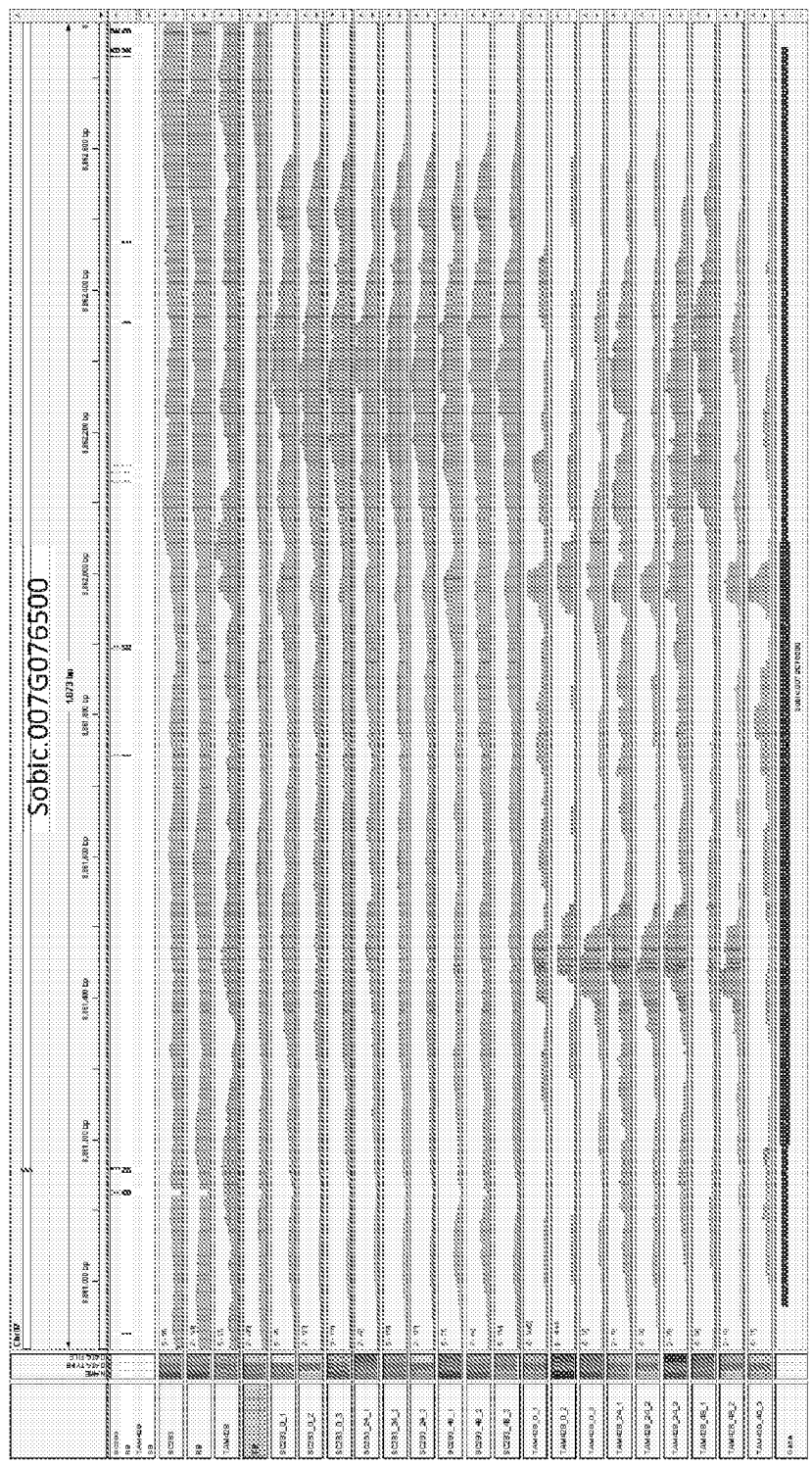
Figure 12:
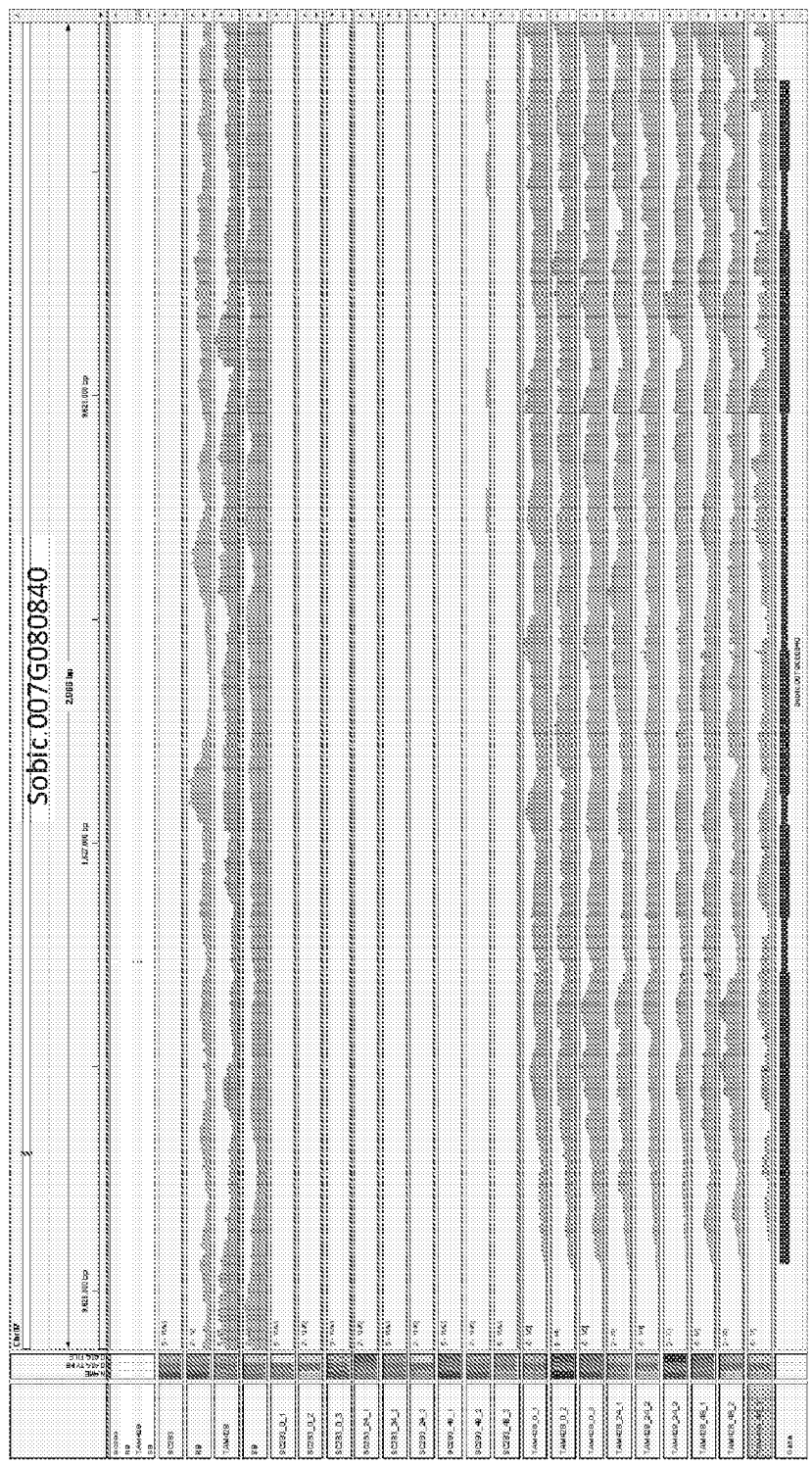
Figure 12:
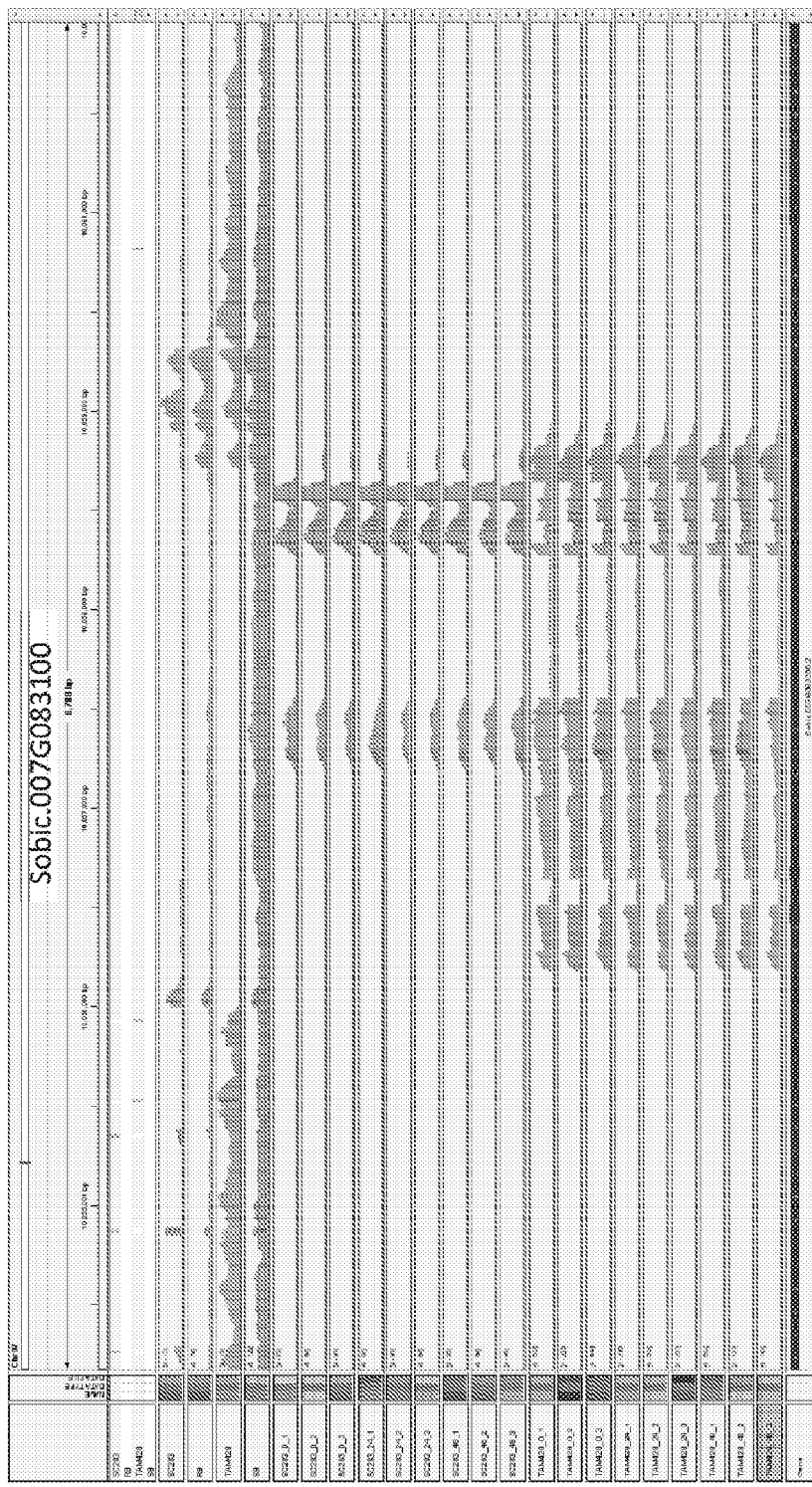
Figure 12:
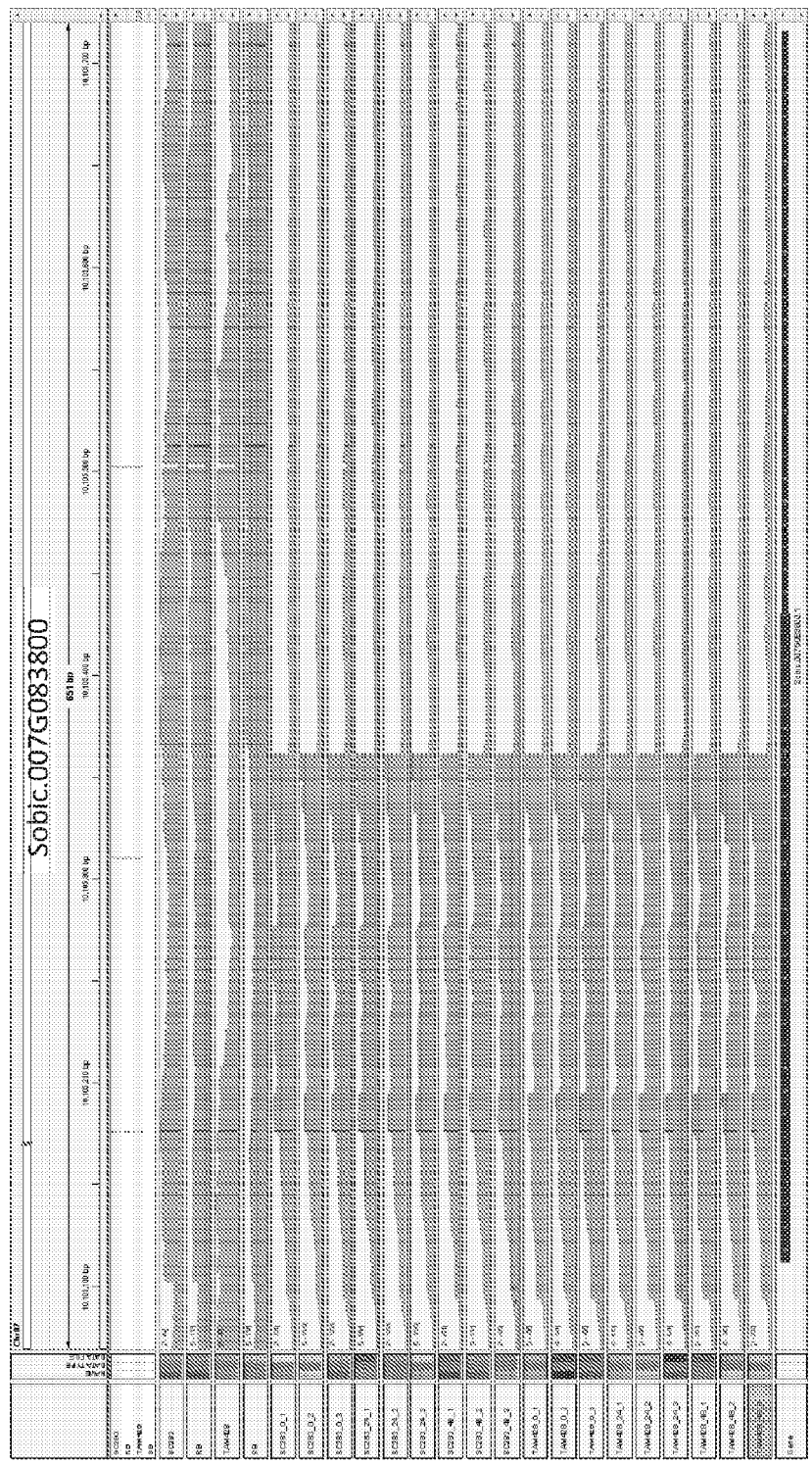
Figure 12:
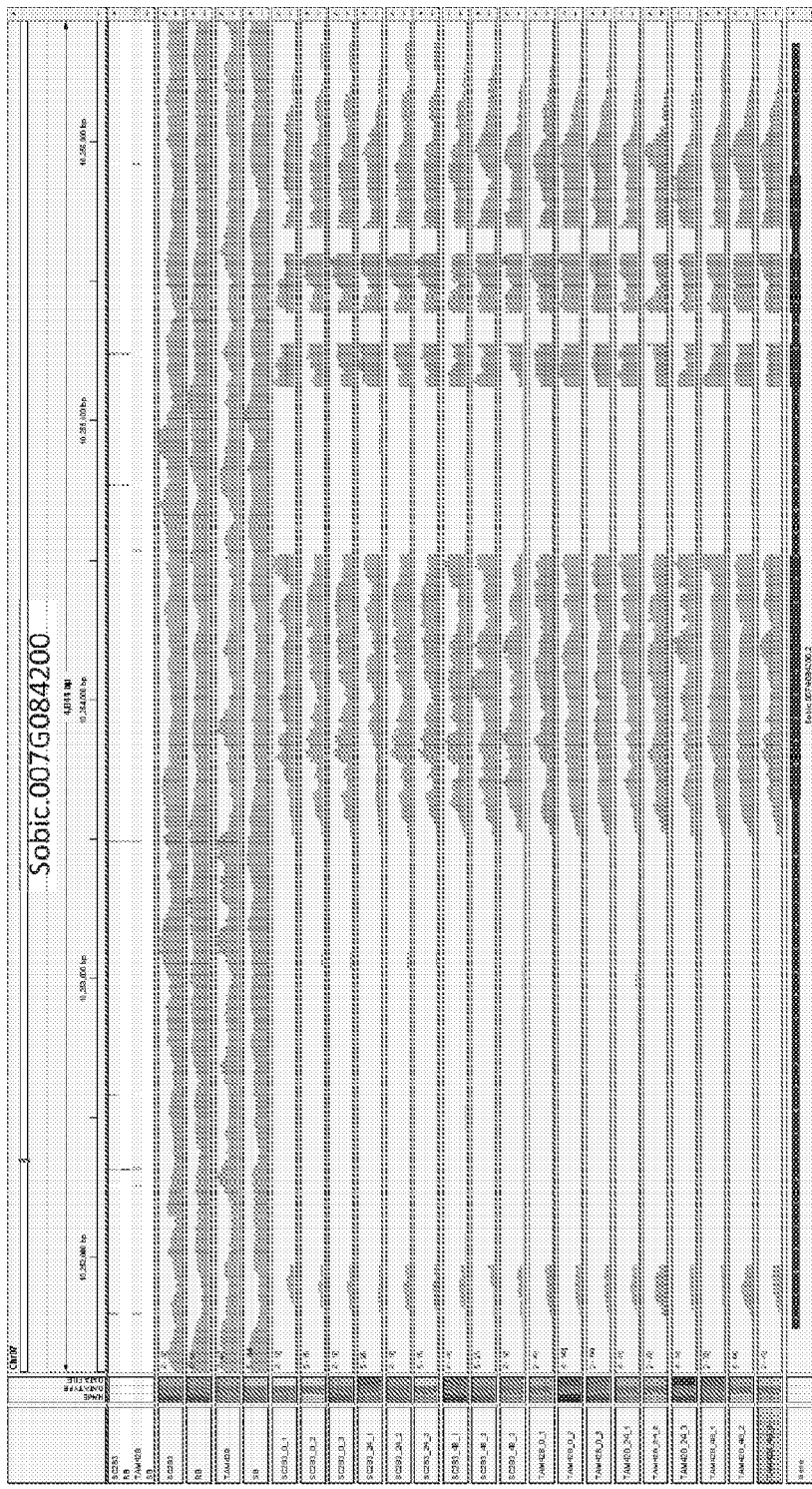
Figure 12:
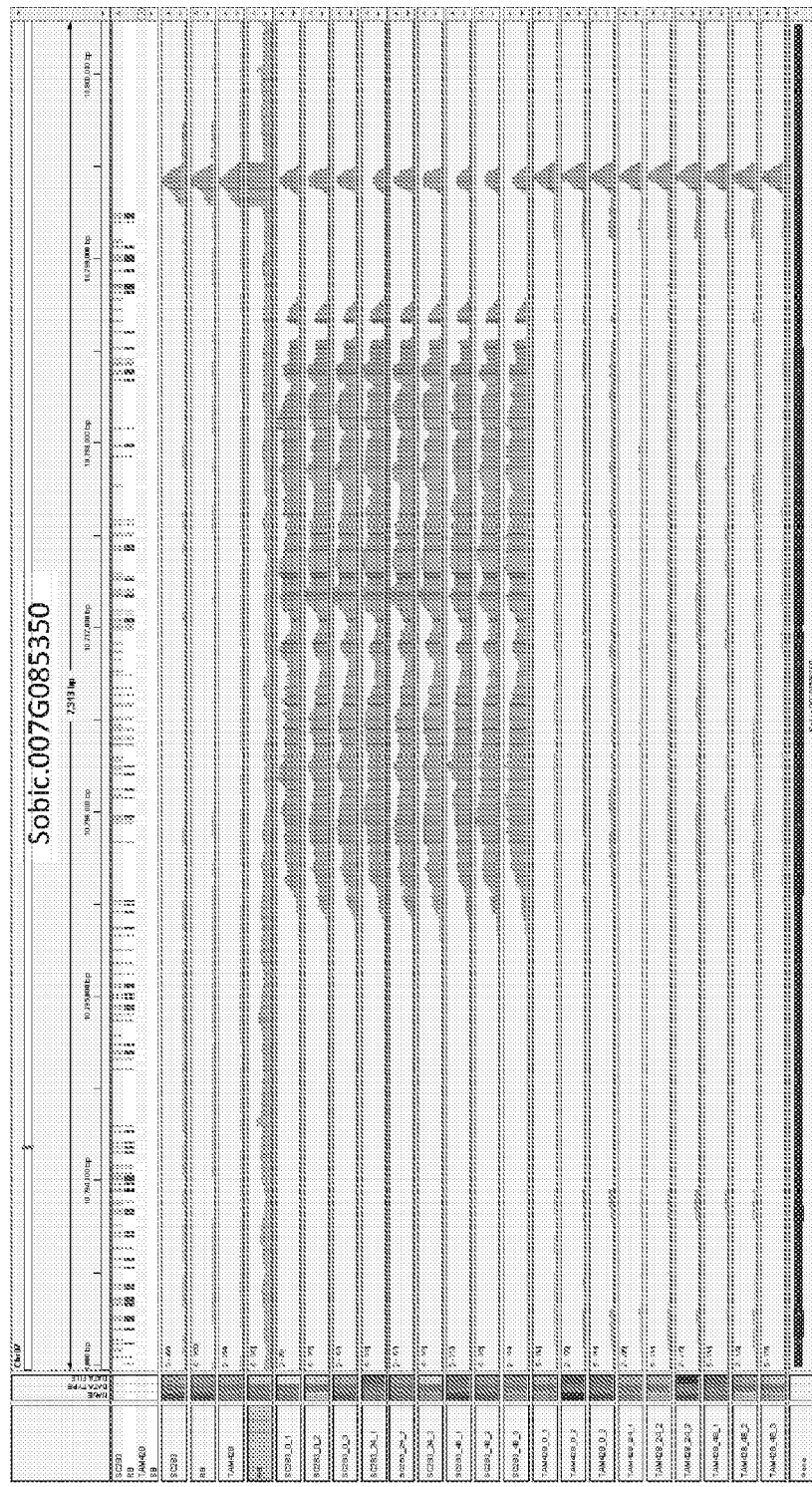
Figure 12:
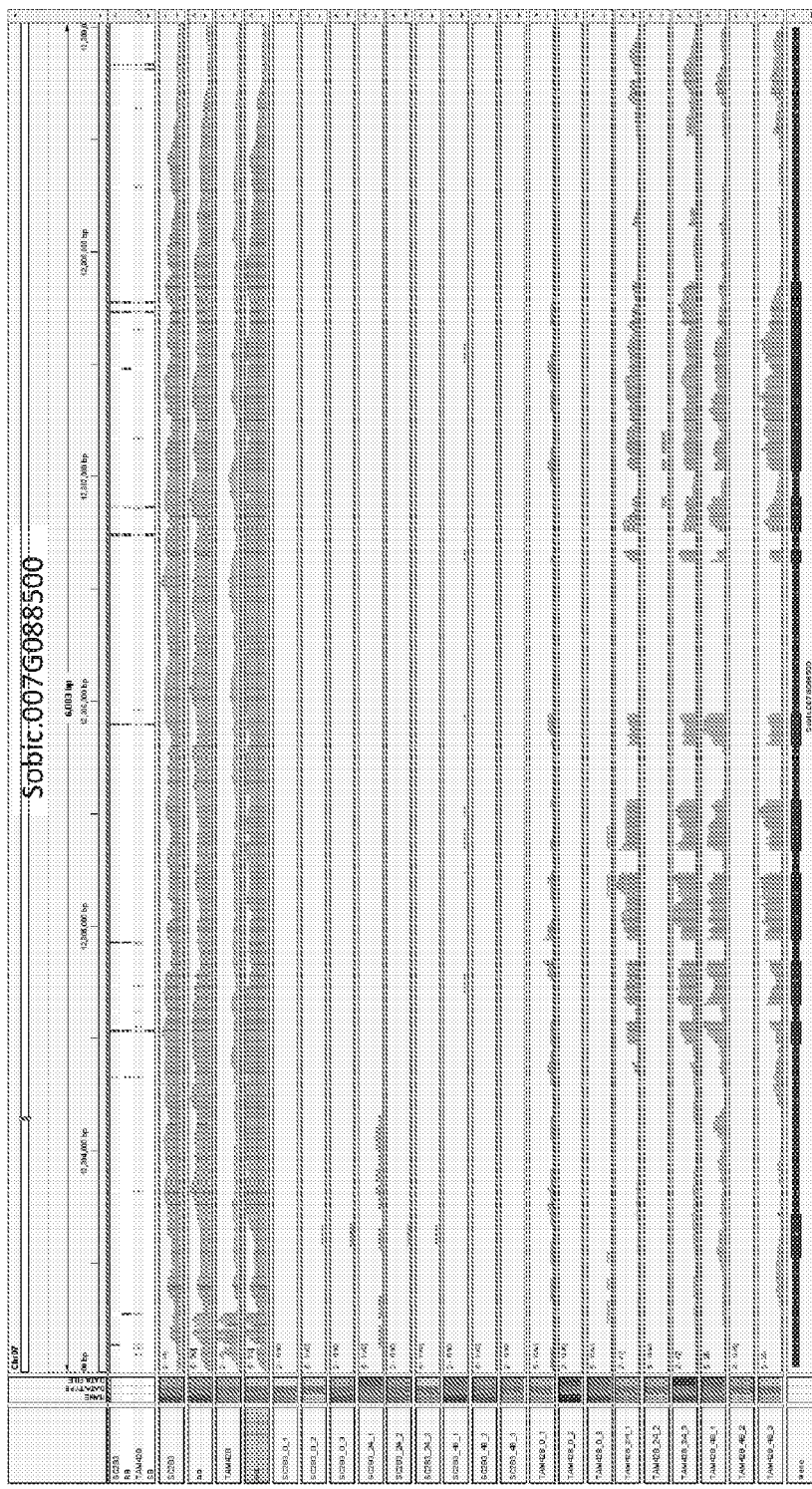
Figure 12:
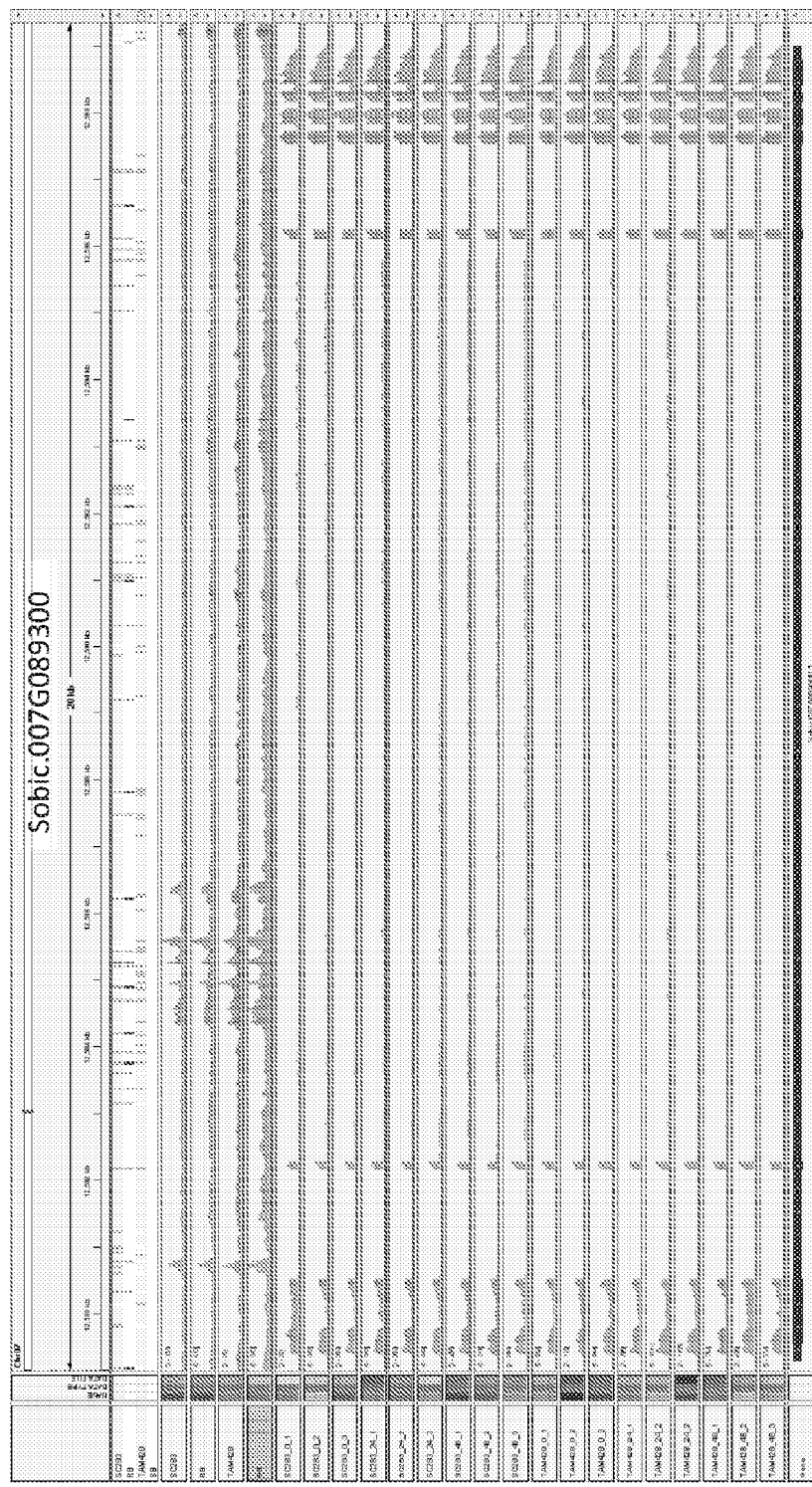
Figure 12:
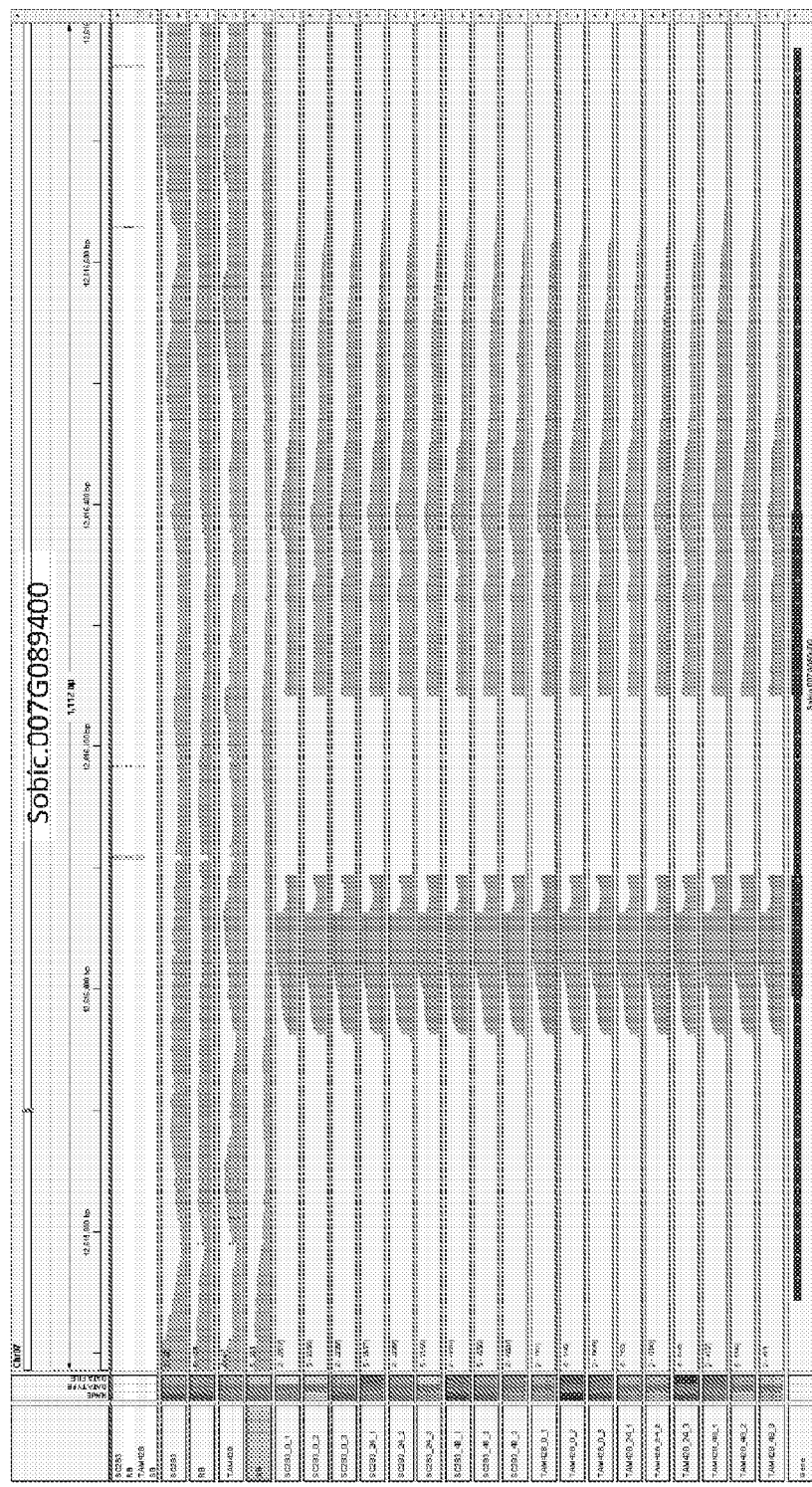
Figure 12:
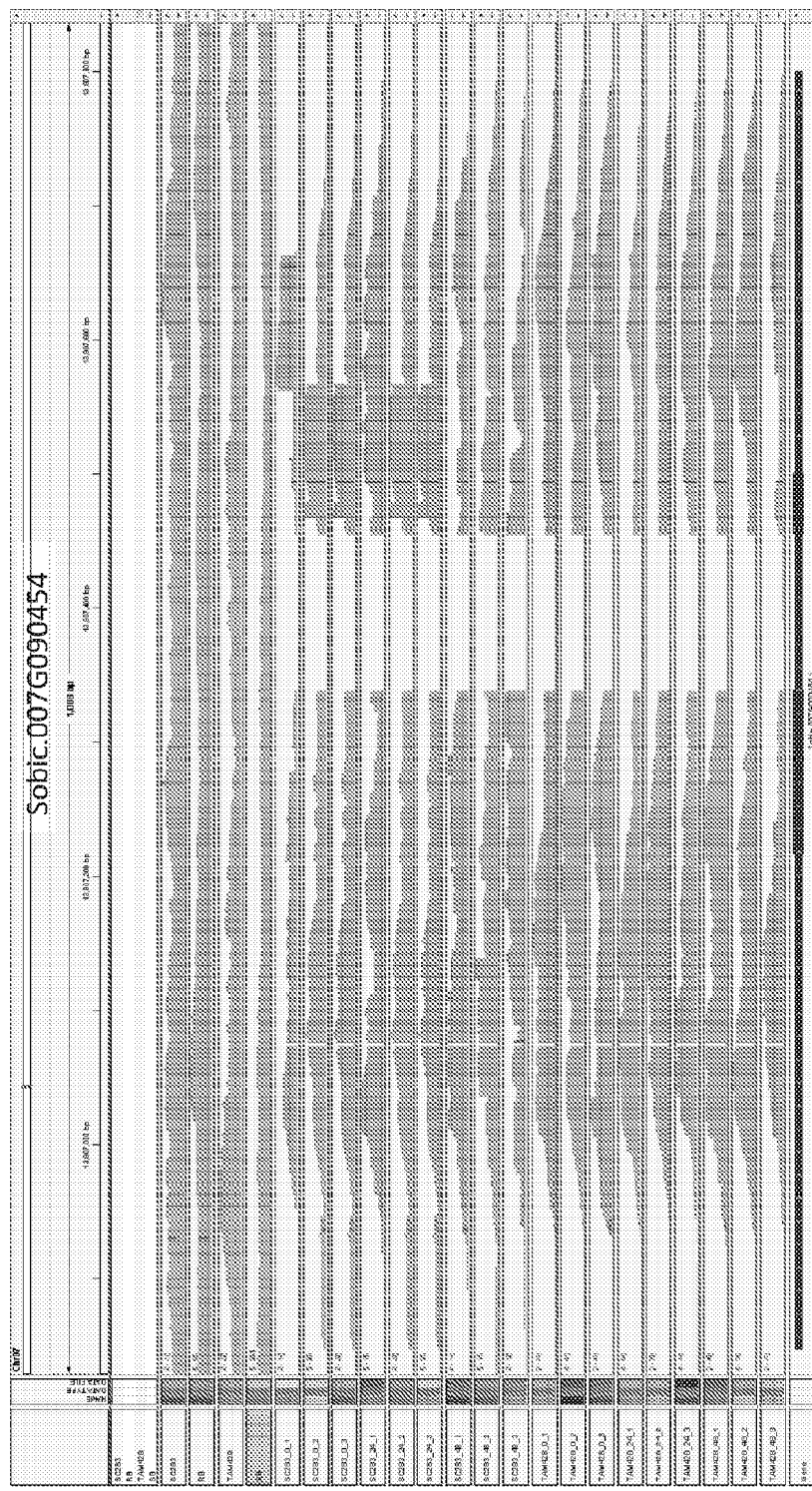
Figure 12:
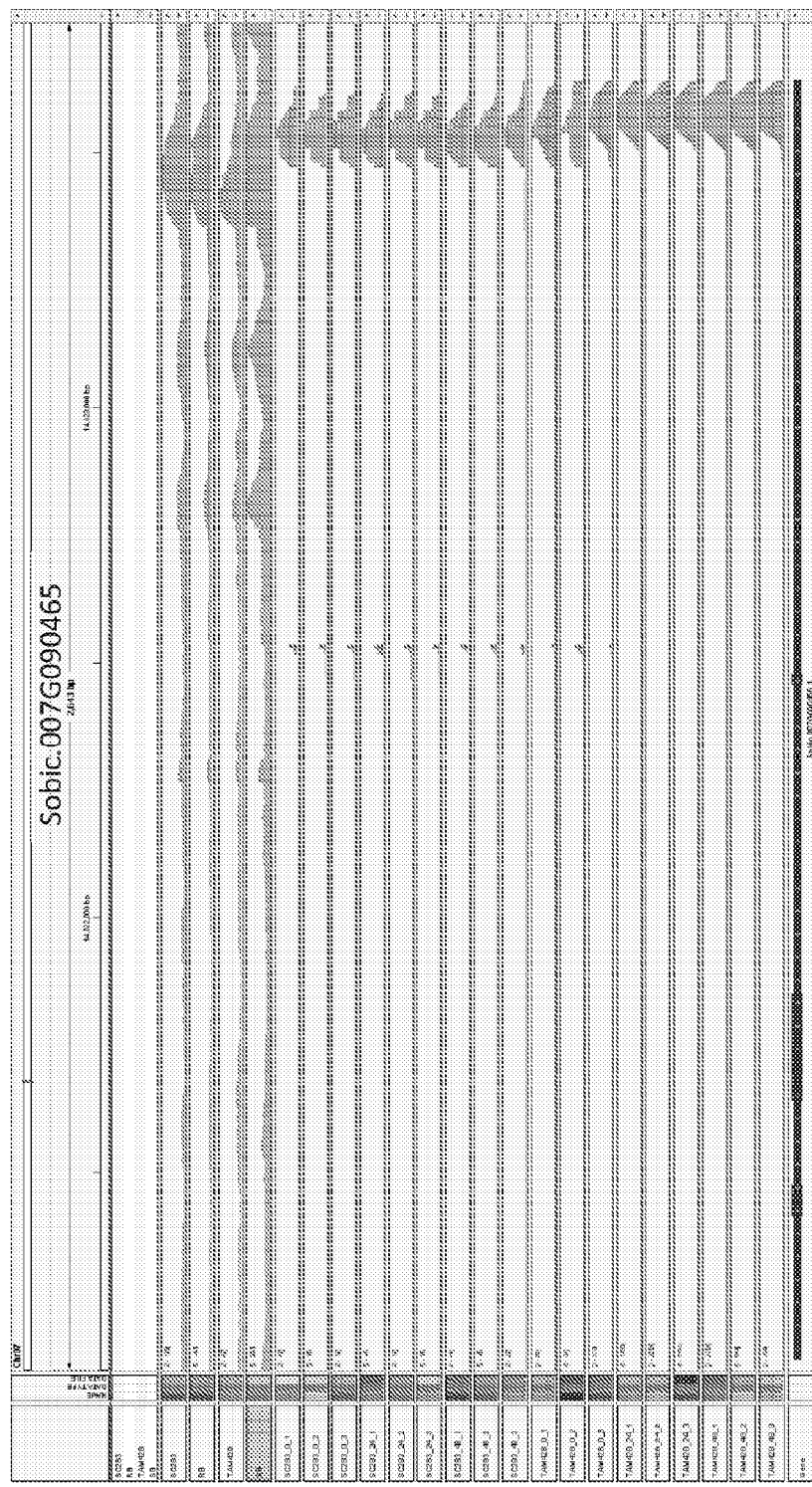
Figure 12:
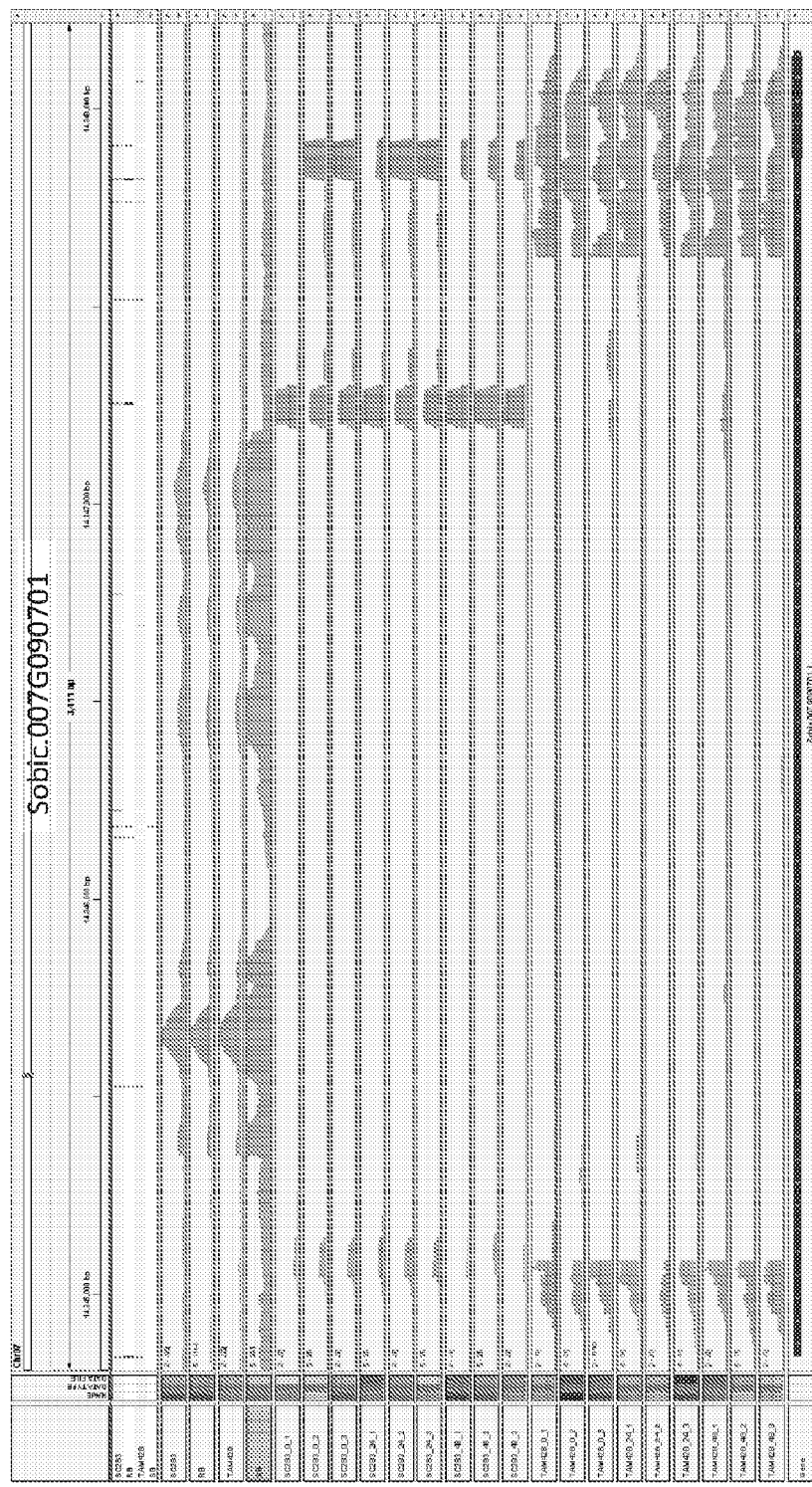

FIG. 12. Variations of genes in QTL region.

Figure 13:
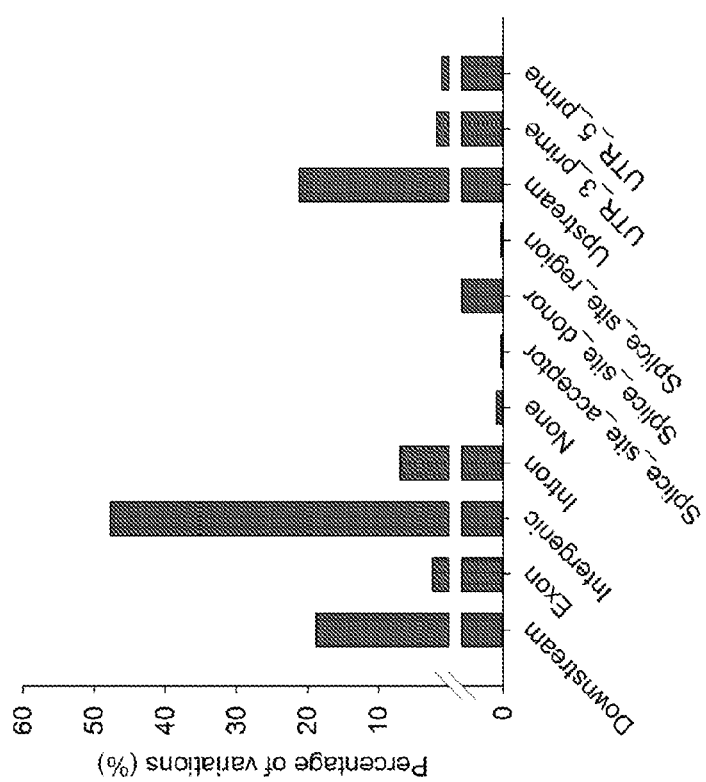

FIG. 13. Distribution SNPs in exon, intron, and UTR regions of genes.

FIG. 14. ARG1 and CARG gene expressions in resistant and susceptible genotypes. (FIG. 14A-C) Expression of ARG1 (FIG. 14A) and CARG (FIG. 14B, FIG. 14C) genes in sorghum genotypes with different CARG alleles. qRT-PCR data was normalized to the constitutively expressed sorghum Actin gene (Sobic.001G112600) as a constitutive control. qRT-PCR was performed using CARG and ARG1 gene specific primers. The qRT-PCR results are obtained with primers flanking the large intron (F2-R2, FIG. 14B) and the first exon of CARG (F1-R1, FIG. 14C). The F2-R2 primers were designed to flank the intron of the CARG to verify the identity of the transcript.

Error bars indicate the standard deviation from three technical replicates of three independent biological repeats (n=9). Error bars show ±SD (n=9). Letters indicate significant difference based on the Least Significant Difference (LSD) (P<0.05). Similar results were obtained in two independent experiments.

FIG. 15. Sequence alignments of ARG1 sequences from the resistant SC283 (SEQ ID NO: 1) and susceptible TAM428 genotypes (SEQ ID NOS: 21 and 27). The sequences of full-length and spliced ARG1 from SC283 and TAM428 are aligned by using MAFFT (Multiple Alignment using Fast Fourier Transform). The stop codon in the middle of ARG1 from TAM428 is in red.

Figure 16A:
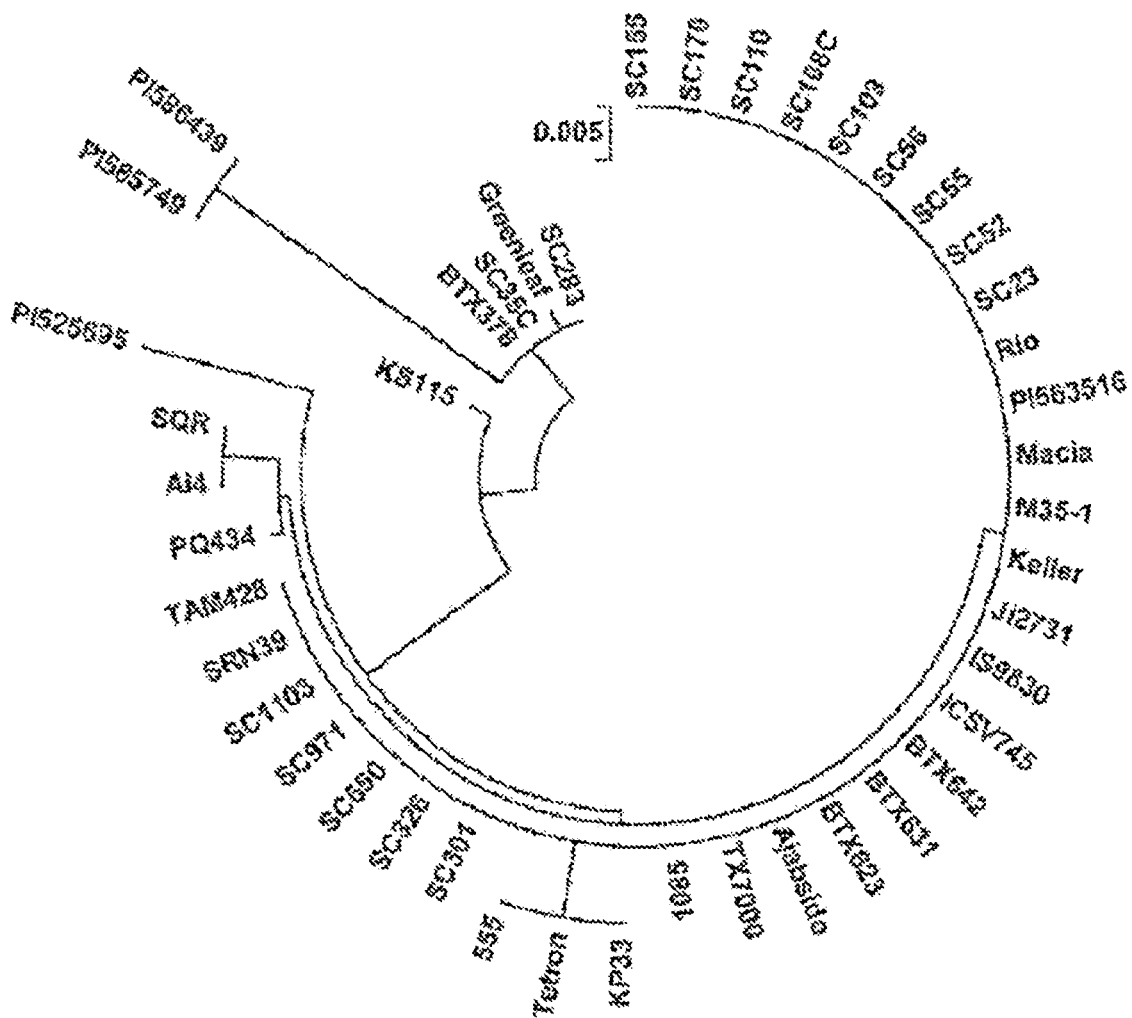

FIG. 16. FIG. 16A and FIG. 16B Dendrogram based on variations in ARG1 sequences showing the relationship between various sorghum genotypes, and ARG1 sequence comparisons from different sorghum sources obtained from the public databases (P1585749 and P1586439 (SEQ ID NO: 28); KS115 (SEQ ID NO: 29); Greenleaf (SEQ ID NO: 30); BTX378 and SC35C (SEQ ID NO: 31); SC283 (SEQ ID NO: 32); P1525695 (SEQ ID NO: 33); Ai4 (SEQ ID NO: 34); SQR (SEQ ID NO: 35); PQ434 (SEQ ID NO: 36); 555, KP33, and Tetron (SEQ ID NO: 37); 1085, Ajabsido, BTX623, BTX631, BTX642, ICSV745, IS9830, Ji2731, Keller, M35-1, Macia, P1563516, Rio, SC23, SC52, SC55, SC56, SC103, SC108C, SC110, SC155, SC170, SC301, SC326, SC650, SC971, SC1103, SRN39, TAM428, and TX7000 (SEQ ID NO: 38). Alignment generated by MAFFT Multiple Alignment using Fast Fourier Transform). The mutation that introduces the stop codon in the middle of the ARG1 protein is in red.

Figure 17:
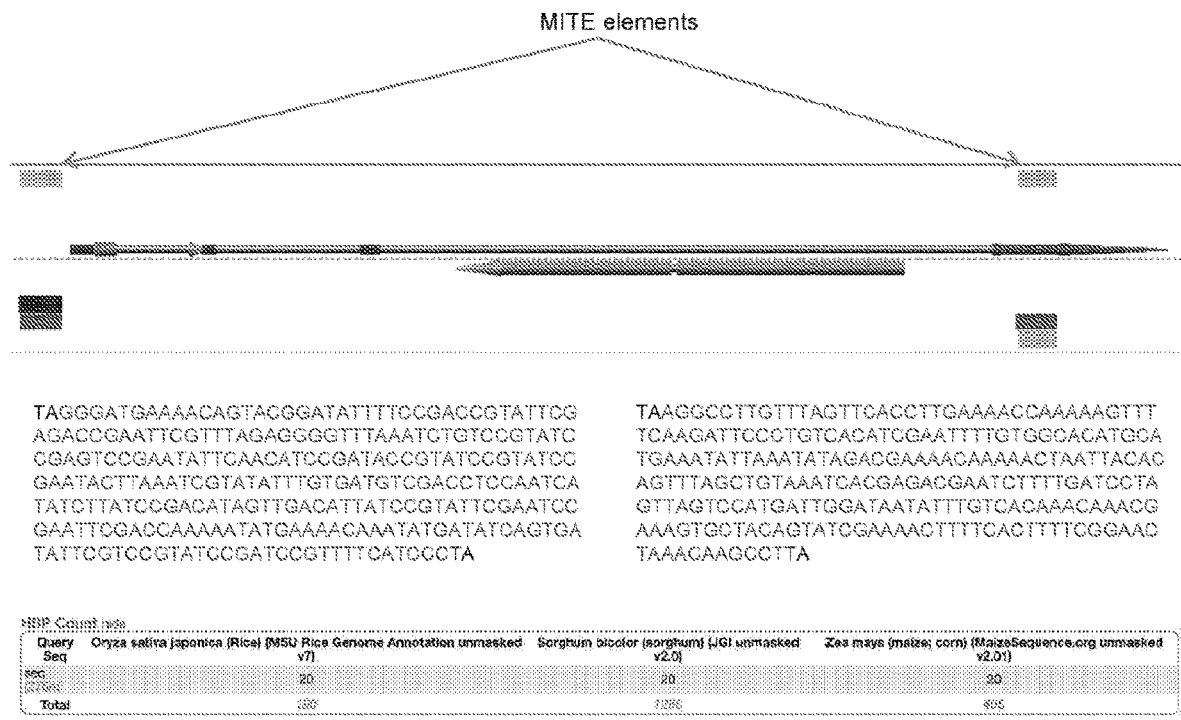

FIG. 17. Location and sequences (SEQ ID NO: 23 on the left, and SEQ ID NO: 24 on the right) of the MITE elements flanking the CARG and ARG1 locus.

FIG. 18. Sequence alignments between the two MITE sequences showing distinct nucleotide sequences (5primeMITE (SEQ ID NO: 23) and 3primeMITE (SEQ ID NO: 24), both in part).

Figure 19:
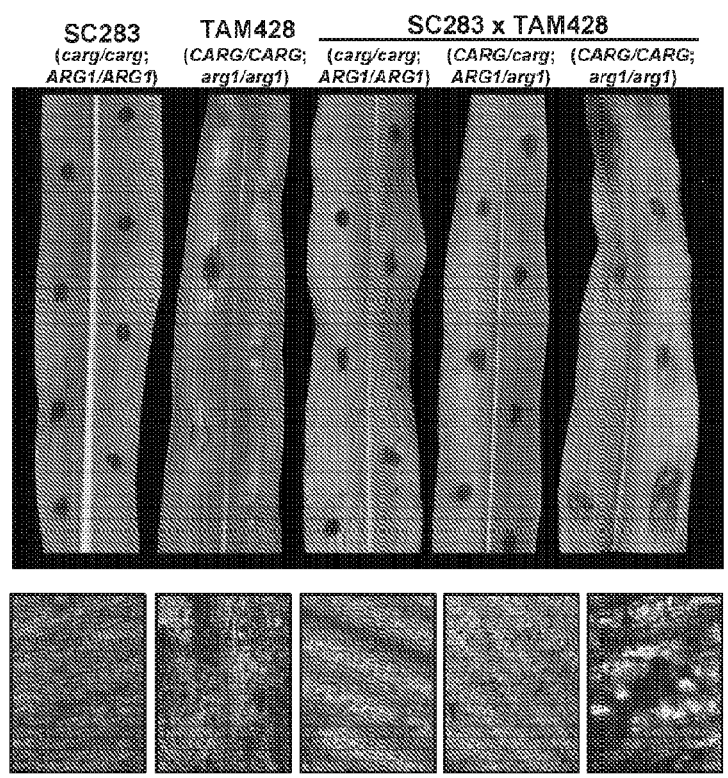

FIG. 19. Disease responses of F2 plants after drop inoculation with *Colletotrichum sublineolum* spores.

Disease response on detached leaves of SC283, TAM428 and F2 plants after drop inoculation (Top row). Leaves from 4-week-old plants were inoculated with *C. sublineolum* strain Cgsl2. Leaves were photographed 12 d post inoculation (dpi). Bottom row shows trypan blue staining of infected tissues to reveal fungal growth.

Figures 20, 20A, 20B, 20C:
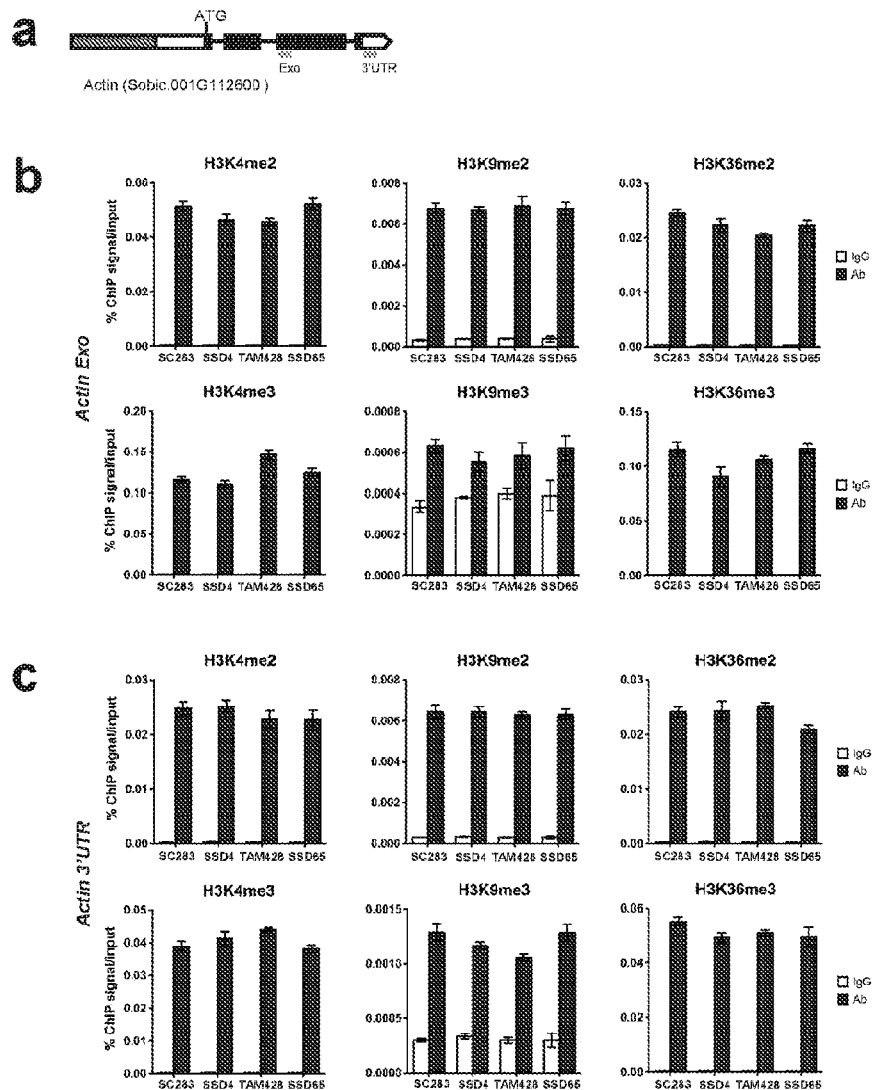

FIG. 20. H3K4, H3K9 and H3K36 di- and tri-methylations at sorghum Actin gene in CSA resistant and susceptible lines.

(FIG. 20A) Schematic showing the genomic region of sorghum Actin gene (Sobic.001G112600). The location of primers at the coding regions (Exo) and 3'-UTR (3'UTR) that were used to analyze the level of H3 methylations by ChIP assays are shown. The gray, white and black boxes indicate promoter, UTRs and exons respectively. (FIG. 20B) Relative enrichment of H3K4me2/3, H3K9me2/3 and H3K36me2/3 at the exon of Actin gene. (FIG. 20C) Relative enrichment of H3K4me2/3, H3K9me2/3 and H3K36me2/3 at the 3'-UTR of Actin gene. ChIP was performed on chromatin extracts using antibodies that recognize different histone methylations as indicated, and IgG serves as a background level. Data from each experiment were normalized to sorghum Actin (Sobic.001G112600) gene and are presented as percentage of IP/input. Data are representative of one biological experiment with three technical replicates. Error bars show ±SD (n=3). Similar results were obtained in two independent biological experiments. Ab, Antibody. SSD4 and SSD65 are resistant and susceptible recombinant inbred lines, respectively.

Figures 21, 21A, 21B:
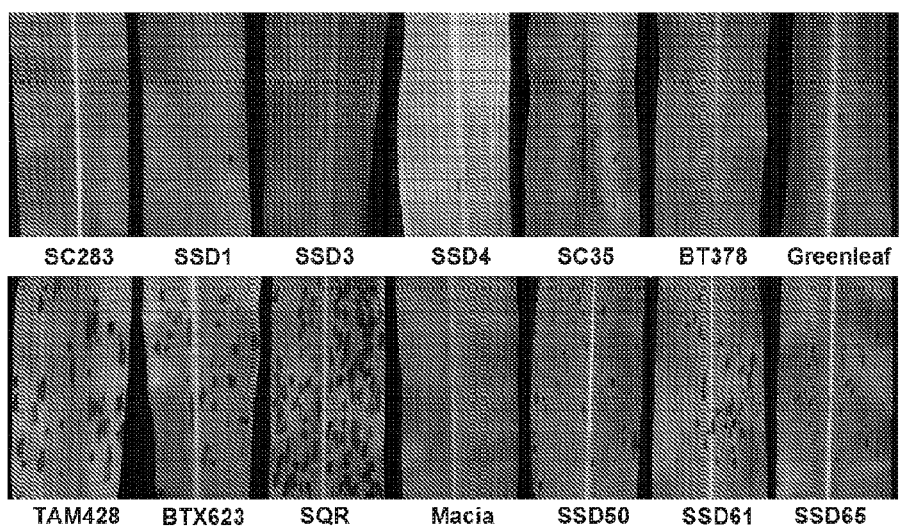

FIG. 21. ARG1 (Sobic.007G085400) confers resistance to the fungal diseases target spot and rust. (FIG. 21A) Target spot disease symptom on different CARG genotypes. (FIG. 21B) Rust disease score on different CARG genotypes.

Figure 22:
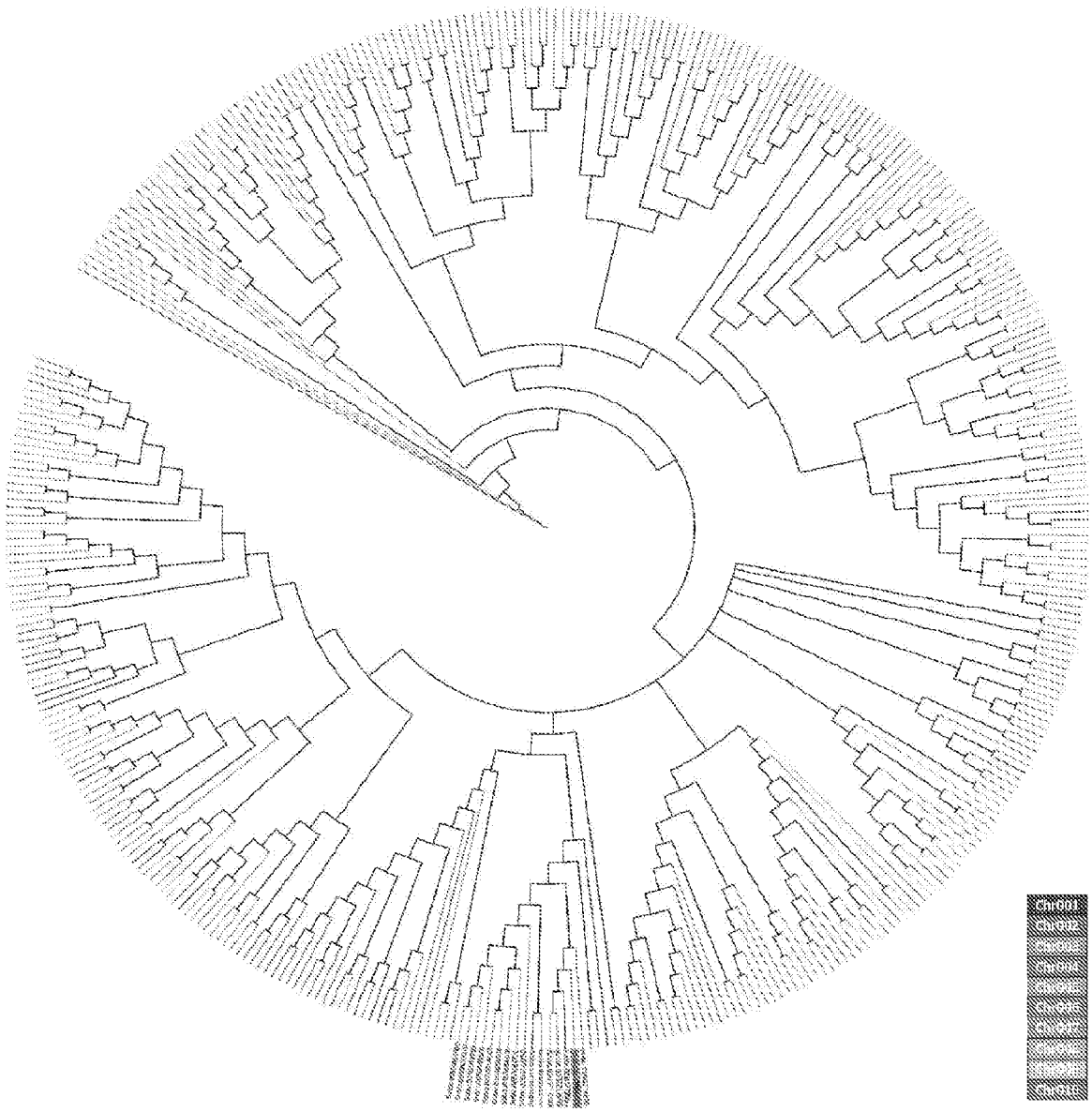

FIG. 22. Phylogenetic trees of NBS-encoding genes from Sorghum. Color coded by chromosomes as indicated. The tree was constructed by the Neighbor-Joining method using bootstrap value based on 1,000 cycles of resampling with PhyIL program.

FIG. 23. Alignment of amino acid sequences of ARG1 from SC283 (SEQ ID NO: 39) and TAM428 (SEQ ID NO: 40), generated by Clustal Omega on EMBL-EBI. The stop codon in the middle of ARG1 from TAM428 is boxed by red color. Asterisk (*) indicates conserved residue, colon (:) indicates strongly similar properties between residues, and period (.) indicates weakly similar properties between residues. NB-ARC, nucleotide binding site; LRR, leucine-rich repeat domain.

BRIEF DESCRIPTION OF THE SEQUENCE LISTINGS

SEQ ID NO: 1 is an isolated polynucleotide sequence [ARG1] that confers sorghum broad spectrum resistance to fungi;

SEQ ID NO: 2 is a nucleic acid sequence that reversely embeds SEQ ID NO: 1 [CARG];

SEQ ID NO: 3 is an artificial nucleic acid sequence of a forward primer of InDel14 for a PCR marker for use with the sorghum genome: CTTTGTGGATCTACCGGACTTC;

SEQ ID NO: 4 is an artificial nucleic acid sequence of a reverse primer of InDel14 for a PCR marker for use with the sorghum genome: TCTCTAATACTCCCAACTCTCTACTC;

SEQ ID NO: 5 is an artificial nucleic acid sequence of a forward primer of InDel15 for a PCR marker for use with the sorghum genome as follows: CCACAGTCCCACACACAT;

SEQ ID NO: 6 is an artificial nucleic acid sequence of a reverse primer of InDel15 for a PCR marker for use with the sorghum genome: CCTATGGCTCGTTGAGAGTTT;

SEQ ID NO: 7 is an artificial nucleic acid sequence of a forward primer for use to generate the transgenic expression of SEQ ID NO. 1 [antifungal ARG1] in sorghum: TCCCCGCGGTATGGGCTCAGTGTTGTTTA;

SEQ ID NO: 8 is an artificial nucleic acid sequence of a reverse primer for use to generate the transgenic expression of SEQ ID NO. 1 [antifungal ARG1] in sorghum: GGACTAGTATGAAATACTGATTCAAGAGGATA;

SEQ ID NO: 9 is an artificial nucleic acid sequence of a forward primer of InDel16 for a PCR marker for use with the sorghum genome as follows: CCACACAGACGAAAGTCCCT;

SEQ ID NO: 10 is an artificial nucleic acid sequence of a reverse primer of InDel16 for a PCR marker for use with the sorghum genome: TAAAGCGACCTGCTACTTTC;

SEQ ID NO: 11 is an artificial nucleic acid sequence of a qRT-PCR forward primer for CARGa: ACACATGGCAGCCTCAAAG;

SEQ ID NO: 12 is an artificial nucleic acid sequence of a qRT-PCR reverse primer for CARGa: TGCTGTTCAAGAGTCACTATCC;

SEQ ID NO: 13 is an artificial nucleic acid sequence of a qRT-PCR forward primer for CARGb: CCCTGACAGCAAACTTTGTG;

SEQ ID NO: 14 is an artificial nucleic acid sequence of a qRT-PCR reverse primer for CARGb: CAATAGCAGACCCAGGATTCG;

SEQ ID NO: 15 is an artificial nucleic acid sequence of a qRT-PCR forward primer for ARG1: TGTTCTTAACCTTGAGCCACAC;

SEQ ID NO: 16 is an artificial nucleic acid sequence of a qRT-PCR reverse primer for ARG1: ATCCAAATAGAAGGAGCTGACAG;

SEQ ID NO: 17 is an artificial nucleic acid sequence of a qRT-PCR forward primer for Actin: CCTCCAGAAAGGAAGTACAGTG;

SEQ ID NO: 18 is an artificial nucleic acid sequence of a qRT-PCR reverse primer for Actin: GGGCGCAAAGAATTAGAAGC;

SEQ ID NO: 19 is an artificial nucleic acid sequence of a forward primer for Actin in semi-quantitative RT-PCR: CCTCCAGAAAGGAAGTACAGTG;

SEQ ID NO: 20 is an artificial nucleic acid sequence of a reverse primer for Actin in semi-quantitative RT-PCR: GGGCGCAAAGAATTAGAAGC;

SEQ ID NO: 21 is a nucleic acid sequence of sorghum bicolor;

SEQ ID NO: 22 is an artificial nucleic acid sequence labelled herein as CARL TAM428;

SEQ ID NO: 23 is a nucleic acid sequence of a first transposable element (MITE) in sorghum as follows: TAGGGATGAAAACAGTACGGGATATTTTCCGACCGTATTCGAGACCGAATTCGTTTA GAGGGGTTTAAATCTGTCCGTATCCGAGTCCGAATATTCAACATCCGATACCGTATC CGTATCCGAATACTTAAATCGTATATTTGTGATGTCGACCTCCAATCATATCTTATCC GACATAGTTGACATTATCCGTATTCGAATCCGAATTCGACCAAAAATATGAAAACAA ATATGATATCAGTGATATTCGTCCGTATCCGATGCGTTTTCATCCCTA;

SEQ ID NO: 24 is a nucleic acid sequence of a second MITE in sorghum as follows: TAAGGCCTTGTTTAGTTCACCTTGAAAAC-CAAAAAGTTTTCAAGATTCCCTGTCACA TCGAATTTTGTGGCACATGCATGAAATATTAAATATAGACGAAAACAAAAACTAATT ACACAGTTTAGCTGTAAATCACGAGACGAATCTTTTGATCCTAGTTAGTCCATGATT GGATAATATTTGTCACAAACAAACGAAAGTGCTACAGTATCGAAAACTTTTCACTTT TCGGAADTAAACAAGCCTTA;

SEQ ID NO: 25 is a small RNA sequence of a hairpin variant of a MITE that expresses a pre-miRNA processed into sbi-miR6225: GAGACGAAUCUUUUGAUCCUAGUU;

SEQ ID NO: 26 is a novel small RNA sequence of a MITE of the present disclosure: GAGAUGAAUCUUUUGAGUCUAGUU;

SEQ ID NO: 27 is a spliced nucleic acid sequence of sorghum bicolor (SEQ ID NO: 21);

SEQ ID NOS: 28-38 are nucleic acid sequences of various sorghum ARG1 variants as follows, SEQ ID NO: 28 is P1585749 and P1586439 variants, SEQ ID NO: 29 is a KS115 variant, SEQ ID NO: 30 is a Greenleaf variant, SEQ ID NO: 31 is BTX378 and SC35C variants, SEQ ID NO: 32 is a SC283 variant, SEQ ID NO: 33 is a P1525695 variant, SEQ ID NO: 34 is an Ai4 variant, SEQ ID NO: 35 is a SQR variant, SEQ ID NO: 36 is a PQ434 variant, SEQ ID NO: 37 is 555, KP33, and Tetron variants, SEQ ID NO: 38 is a number of variants including 1085, Ajabsido, BTX623, BTX631, BTX642, ICSV745, IS9830, Ji2731, Keller, M35-1, Macia, P1563516, Rio, SC23, SC52, SC55, SC56, SC103, SC108C, SC110, SC155, SC170, SC301, SC326, SC650, SC971, SC1103, SRN39, TAM428, and TX7000;

SEQ ID NO: 39 is an amino acid sequence of ARG1 from SC283;

SEQ ID NO: 40 is an amino acid sequence of ARG1 from TAM428; and

SEQ ID NO: 41 is a partial nucleic acid sequence of variant ZZZ.

In addition to the foregoing, the above-described sequences are provided in computer readable form encoded in a file filed in connection herewith and herein incorporated by reference. The information recorded in computer readable form is identical to the written Sequence Listings provided above and referenced herein, in accordance with 37 C.F.R. § 1.821(f).

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Anthracnose is a major foliar disease of sorghum that completely kills plants in the absence of resistance genes. Both the molecular mechanisms and the genes that regulate plant immunity to this pathogen are poorly understood.

Among a collection of sorghum natural variants, the sorghum genotype SC283 displays a high level of resistance to different Cs strains, whereas the TAM428 genotype is susceptible to many different strains of the fungus. Recombinant inbred lines (RILs) generated by crossing SC283 with TAM428 displayed clear-cut disease responses similar to the parental lines. Whole-genome resequencing of DNA from resistant and susceptible RILs defined a major anthracnose resistance locus in SC283 that also confers resistance to other fungal pathogens. The resistance locus is composed of the ANTHRACNOSE RESISTANCE GENE 1 (ARG1) gene, encoding a canonical NLR that is nested in an intron of a unique NAT, designated CARRIER OF ARG1 (CARG). DNA- and RNA-seq analysis revealed that in resistant RILs, a deletion that abrogates CARG expression is associated with significantly enhanced expression of the nested ARG1 gene. Loss of CARG transcription in distinct sorghum lines carrying distinct CARG mutant alleles are also associated with an increase in ARG1 expression, both confirming the identity of the resistance gene and demonstrating a relationship between the loss of CARG and enhancement of ARG1 expression. In addition, histone H3K4 and H3K36 trimethylation at the region of overlap between CARG and ARG1 and in the ARG1 exon are enriched in resistant but decreased in susceptible alleles. In contrast, susceptibility is attributed to loss of a functional ARG1 allele and an increase in NAT expression. The low expression of the ARG1 gene when the NAT CARG gene is expressed suggests that high levels of CARG expression causes a loss of ARG1 expression.

Here we describe a major fungal resistance locus composed of a nucleotide-binding site leucine-rich repeat receptor (NLR), ANTHRACNOSE RESISTANCE GENE 1 (ARG1), completely nested in an intron of a unique cis-natural antisense transcript (NAT), designated CARRIER OF ARG1 (CARG). The CARG and ARG1 genes are transcribed in opposite orientations and are complementary within portions of the ARG1 and CARG transcripts. This cis-NAT regulated ARG1 gene encoding a plant immune receptor that confers broad spectrum and complete resistance to several distinct fungal pathogens.

CARG shares very limited sequence complementarity with the sense ARG1 transcript apart from a short segment of 101 nucleotides. CARG and ARG1 are transcribed in opposite orientations and exhibit inverse expression levels. Abrogation of CARG expression is associated with derepression of ARG1, which correlates with increased histone H3K4 and H3K36 methylation levels within the single ARG1 coding exon. In addition, the repressive chromatin within the CARG exon is enriched in resistant genotypes that lose CARG expression and is reduced in susceptible genotypes that maintain CARG expression.

In this disclosure we have found that susceptible genotypes of sorghum express CARG and two alternatively spliced ARG1 transcripts, both of which encode putative truncated proteins that lack the LRR domains. In resistant genotypes, loss of CARG transcription is associated with elevated expression of an intact allele of ARG1, resulting in strong and broad-spectrum resistance to fungal species with distinct virulence strategies. The ARG1 gene causes resistance to sorghum rust, target spot, anthracnose and stalk rot. Our findings demonstrate a uniquely organized sorghum NLR locus, regulated by non-coding RNA, DNA and histone methylation that confers broad-spectrum and powerful fungal resistance against most damaging pathogens of sorghum.

It should be acknowledged that the primary lesion most likely to be responsible for susceptibility is the premature stop codon present in all of the susceptible genotypes. The loss of the conserved LRR domain likely results in a non-functional protein, and is may also lead to nonsense-mediated decay of the ARG1 transcript, which would explain its reduced steady state levels[25]. The increased level of CARG in susceptible lines may then be a consequence of the loss of transcriptional interference due to reduced levels of ARG1 in these genotypes. According to this scenario, the changes in expression levels and chromatin modifications would be a consequence rather than a cause of a mutation in ARG1 that results in a loss of ARG1 transcript.

However, there are a number of lines of evidence that suggest an alternative hypothesis, in which the NAT is a key player in the differentiation between resistant and susceptible genotypes. First, we note that all resistant genotypes have a genetic lesion within the CARG gene that is associated with a loss of CARG expression. Because there are at least two independent mutations associated with this loss of expression, it would appear that the loss of CARG expression occurred at least twice independently, and, in each case, is associated with increased ARG1 expression as well as the presence of a wild type version of the ARG1 gene. The tight association between two genetic lesions in the NAT and the absence of one in the ARG1 gene suggests that both lesions are required for resistance, one of which permits expression of the resistance gene due to the loss of the NAT, and one of which permits expression of a functional NB-LRR gene. However, because the polymorphisms in the two genes have not been separated, it is not possible at this time to determine whether or not both of them are required for the production of large quantities of functional ARG1 protein. The most straightforward way to determine this would be to genetically modify a resistant genotype such that CARG expresses at high levels in situ. If this modification results in a sensitive phenotype despite the presence of an intact ARG1 gene, it would be possible to conclude that loss of the NAT is required for full resistance.

There are also other scenarios that are worth entertaining. NBs-LRR genes are often found at new locations in different accessions or related species, and many of these "transposed" genes are not functional, likely often because of local sequence context. Indeed, we find that ARG1 is not present at a syntenic position in the maize, rice or *Setaria* genomes, suggesting movement of this gene at some point in its evolutionary history (data not shown). It is quite possible that movement of ARG1 placed it in antisense orientation relative to a long non-coding RNA, which effectively prevented it from expressing. Consequent relaxed purifying selection could have then resulted in the acquisition of a stop codon, as well as additional polymorphisms that may contribute to ARG1's unique broad-spectrum resistance. Subsequent strong selective pressure caused by disease could then have led to selection for a back mutation of the stop codon, allowing expression of some quantity of functional ARG1 protein and some degree of resistance. Subsequent mutations that abrogated CARG1 expression might then have been rapidly fixed in these lines if they significantly enhanced resistance, which would be why polymorphisms in both CARG and ARG1 are found in all current resistant genotypes. According to this scenario, one would expect that correction of only the ARG1 lesion would cause reduced resistance and correction of both the ARG1 and CARG lesions would result in full resistance.

The nature of the ARG1 exons skipping is also unusual in that the skipping or the production of two transcripts from the same genomic template occurs in the absence of obvious well-defined intronic sequences in the ARG1 gene. Many resistance genes are regulated by differential splicing where premature stop codons introduced by frame shifts result in variant transcripts which encode proteins lacking LRR repeats. However, the functions of these transcripts or truncated proteins in the susceptible backgrounds is unknown.

Proteins with canonical NLR protein structure mediate recognition of virulence effectors, which then activate a very strong and specific form of resistance that varies depending on the pathogen strain. ARG1 encodes a typical NLR, which in SC283 and other genotypes containing an intact ARG1 gene and exhibiting a loss of CARG transcript conferred resistance to distinct pathogen groups. These mutations confer resistance to the obligate biotrophic fungus *Puccinia purpurea* (which causes sorghum rust), the hemibiotrophic fungus *Colletotrichum sublineolum* as well as the necrotrophic fungus *Bipolaris sorghicola* (which causes target spot in sorghum). Even more striking, NLR mediated responses in these genotypes promote susceptibility to a variety of other necrotrophic fungi[26,27]. SC283 and other resistant cultivars display qualitative resistance accompanied by the HR and complete absence of fungal growth. Broad-spectrum resistance to distinct pathogenic species with disparate virulence strategies and life styles is extremely uncommon. HR has been a hallmark of NLR mediated resistance but is also correlated with susceptibility to some necrotrophic pathogens[28]. It is possible that ARG1 recognizes a conserved effector that is common to different plant pathogen lineages, although given the strong selective pressure for pathogens to differentiate from each other, this would seem unlikely. Alternatively, depression of ARG1 may activate an immune response that is broadly effective against many pathogens[1].

In eukaryotic cells, non-coding RNAs affect gene expression through transcription interference, RNA masking, dsRNA dependent mechanism, RNA interference, or antisense mediated methylation[7,20]. In Arabidopsis, the role of antisense transcripts (COOLAIR) in the cold-induced, epigenetic silencing of Arabidopsis FLOWERING LOCUS C (FLC), a regulator of the transition to reproduction is linked to switching of chromatin states at FLC during vernalization[5]. Inference of transcription and consequent changes in chromatin has also been observed in other systems[29]. Due to the complementarity of parts of the CARG 3'-UTR and ARG1 5'-UTR regions, and the identification of small RNAs that map to the overlapping region, we suggest that the low levels of expression in susceptible genotypes may be due, at least in part, to sense-antisense interference, and that this process may result in changes in chromatin modification of both genes.

DNA and histone methylations are epigenetic marks associated with regulation of gene expression in plant and animal cells. Histone and DNA methylations are known to interact with each other[30]. Histone methylation can help direct DNA methylation patterns, and DNA methylation can serve as a template for some histone modifications[31]. Often, de novo methylation can be triggered by small RNAs (see, e.g., Cuerda-Gil et al., Non-canonical RNA-directed DNA methylation, *Nat Plants* 3, 2(11): 16163 (November 2016)). Methylation of transgene and transposon promoters correlates with transcriptional gene silencing, whereas methylation of coding sequences is sometimes associated with post-transcriptional gene silencing[32]. Interestingly, there does appear to be a connection between DNA methylation and plant resistance. Chemically induced demethylation of the rice R gene Xa21G abolishes silencing of this gene and provides heritable resistance to *Xanthomonas oryzae*[33]. Increased DNA methylation after bacterial infection has also been reported[34,35]. Arabidopsis mutants met1 and ddc mutants that impact DNA methylation have also been shown to be resistant to the bacterial pathogen *Pseudomonas syringae*[34]. Although not directly related to DNA methylation, chromatin marks associated with active transcription such as H3K4me2 are reduced when genes are subject to epigenetic silencing We find that H3K4 methylation of ARG1 is significantly enriched in genotypes that show high levels of expression of ARG1, as is H3K4 and H3K36 in the exon of CARG in genotypes that express high levels of that gene. Similarly, we observe enrichment of the repressive H3K9 methylation in the exon of CARG1 in resistant genotypes in which expression of this gene is low. However, we note that analysis of chromatin changes of the CARG1 promoter is complicated by the fact that the actual promoter region of this gene is poorly defined and is composed largely of transposable elements. Indeed, of the 1500 bp upstream of the start of CARG transcription, only 258 bp are non-transposon sequences. The region assayed as the promoter of CARG in this analysis is in a non-autonomous member of the hAT family of transposable elements (177 blast hits in sorghum at e-value set at $10^{-5}$). This might suggest that any chromatin modifications in this region may have more to do with transposon silencing than regulation of CARG gene expression. However, this is not the case. In this CARG upstream transposon, we find that H3K9me2 is enriched in genotypes in which CARG expresses at a high level, concomitant with depletion of H3K4 and H3K36 methylation in this region, as well as an increase in CHG methylation, which is often associated with H3K9me2.

Without being bound by any theory, one possible explanation for these observations is that chromatin level repression of this upstream transposon contributes to enhanced expression of the gene in sensitive genotypes, and depression of this transposon in resistant genotypes results in enhanced repression and reduced expression of the adjacent CARG gene. This would explain why the CARG exon shows a reverse pattern of histone modification relative to the upstream transposon, with reduced expression associated with H3K9 methylation increased and H3K4 and HK36 methylation decreased when the CARG gene is expressed at lower levels in resistant genotypes.

Clearly, additional studies are required to determine the exact mechanism by which changes in expression of CARG mediates ARG1 regulation, particularly the means by which changes in DNA and histone methylation caused, or are caused by, changes in gene expression. However, we do find clear evidence that changes in both histone and DNA methylation are associated with changes in expression of these two genes.

ARG1 represents the first example of an NLR regulated by NAT affecting its disease resistance. Further, the broad-spectrum resistance conferred by an NLR to biotrophic, hemibiotrophic and necrotrophic pathogens, all with different modes of pathogenesis strategies is unique. In susceptible cultivars, basal transcription of ARG1 and CARG is likely maintained through mechanisms involving interference with transcription, dsRNA, NAT mediated promoter DNA methylation and repressive chromatin states.

Genetic studies defined multiple loci that control resistance to Cs[36,37,38]. However, the identification of specific resistance genes and their mechanisms of action has been slow in coming. The significance of our finding is in both its direct application for controlling widespread and economically significant sorghum diseases and in an interesting regulatory mechanism of a known class of immune receptors. Resistance associated with a loss of the NAT of an immune receptor gene is unique. Regardless of the molecular and cellular mechanisms involved, the CARG -ARG1 locus provides a unique resistance locus that can be easily introgressed into a variety of sorghum cultivars. The resistance by ARG1 allele confers strong resistance to at least 10 distinct Cs strains tested and two other fungal species.

Genome editing of the NAT gene directly in improved and adapted cultivars to generate broad-spectrum resistance will considerably shorten the breeding cycle and will make it possible to more precisely determine the means by which this unusual locus is regulated.

In sum, we describe the first example of an immune receptor gene that is intricately regulated by non-coding RNA that confers complete and broad-spectrum fungal resistance.

The significance of our finding is in both its direct application for controlling widespread and economically significant sorghum diseases and in an interesting regulatory mechanism of a known class of immune receptors. Resistance associated with a loss of the NAT of an immune receptor gene is unique. Regardless of the molecular and cellular mechanisms involved, the CARG-ARG1 locus provides a unique resistance locus that can be easily introgressed into a variety of sorghum cultivars. The resistance by ARG1 allele confers strong resistance to at least 10 distinct Cs strains tested and two other fungal species. Genome editing of the NAT gene directly in improved and adapted cultivars to generate broad-spectrum resistance will considerably shorten the breeding cycle and will make it possible to more precisely determine the means by which this unusual locus is regulated. In addition, transgenic expression of ARG1 will be useful for generating disease resistant plants.

EXAMPLES

Material and Methods

Plant Growth

The sorghum recombinant inbred lines (RILs) were generated by crossing SC283 and TAM428 and advanced through single seed descent to the F6 generation and then maintained by self fertilization. A total of 209 RIL lines were evaluated six times consecutively since June 2014 in the Purdue University green house. Plant growth conditions, methods of inoculation, and disease response assessments were as previously described[39].

Preparation of Fungal Culture and Plant Disease Assays

The *Colletotrichum sublineolum* (Cs) strains Cgsl1 and Cgsl2 were obtained from Dr. Lisa Vaillancourt (University of Kentucky, Lexington). The other Cs strains are from different regions in Ethiopia and Nigeria (Table 1). All strains were cultured on potato dextrose agar plates at 25° C. Fungal spores were harvested from 15-20 day old cultures, suspended in ddH$_2$O and the concentration of spores was adjusted to $10^6$ spores/mL. The spore suspension was uniformly sprayed on 3- to 4-week-old sorghum plants. Plants were kept in humidity chambers for 2 days and then transferred to the green house with a temperature setting of 28° C. with 16 h light duration and with occasional misting to maintain high humidity. Disease responses were scored by visual assessment of disease symptoms or resistance responses, chlorosis and fungal growth in planta. The detached leaf disease assay for Cs was conducted by drop inoculation of spores on leaves placed on wetted absorbent or filter paper and incubated in sealed transparent trays. A drop of (20 µl of $10^6$ spores/mL) suspension was deposited on each leaf and disease evaluated by measuring lesion area, fungal growth. Fungal growth accessed using qPCR amplification of the fungal rDNA.

Rust (*Puccinia purpurea*) infected sorghum leaves were collected from the Agronomy Center for Research and Education, West Lafayette. The rust inoculum was maintained on rust susceptible genotypes in the green house. Inoculations and disease assays were conducted as described[40].

The target leaf spot fungus *Bipolaris sorghicola* isolates were obtained from Dr. Burt H. Bluhm (University of Arkansas). The strain was cultured, harvested, and plants inoculated using the same method described for Cs strains. The concentration of spores was adjusted to $4 \times 10^4$ spores/mL and plants inoculated as previously described[41].

Trypan Blue Staining

The leaf tissue samples from inoculated plants were collected for staining with trypan blue to reveal fungal growth in leaf tissue. First, the leaves were cleared in acetic acid: ethanol (1:3, v/v) solution overnight followed by clearing using acetic acid: ethanol: glycerol (1:5:1, v/v/v) solution B for 3 hours. The tissue was then stained with trypan blue (0.01% trypan blue in lactophenol) overnight. The stained tissue samples were rinsed multiple times and preserved in 60% glycerol for microscopic observation.

RNA-Seq Analysis

TAM428 and SC283 plants were grown on soil for 3 weeks, and inoculated with Cgsl2 ($10^6$ spore/mL). At 0, 24, and 48 h after inoculation, the fifth leaves were collected from three biological replicates (~6 plants each). Total RNA isolation was performed as described in the protocol of Spectrum™ Plant Total RNA Kit with on-column DNase digestion (Sigma-Aldrich, USA), and treated with DNase and purified using the RNA Clean & Concentration TM-25 (ZYMO RESEARCH). The quality of the total RNA was determined by NanoDrop and Agilent 2100 Bioanalyzer. For each sample, 3 µg total RNA was used to prepare the mRNA-seq library according to the TrueSeq RNA Sample Prep Kit protocol (Illumina). Library quality control and quantification were performed with an Experion DNA 1K Chip (Bio-Rad) and a Qubit fluorometer (Invitrogen), respectively. A total of 734,963,453 high quality reads (average length=99 bp) were generated using an Illumina HiSeq 2500 sequencer (Table S2). For each library, 75 million 100-bp paired-end sequences were generated using an Illumina Hi Seq 2500 sequencer. After removing low-quality sequences containing uncalled bases (Ns), we used the software Tophat 2[42] to align the RNA-seq reads against the reference genome of BTx623 (PhytozomeV10: Sbicolor_313_v3.1). Tophat2 alignment parameters were set to allow a maximum of two mismatches and to exclude reads mapping to more than one position on the reference. Moreover, only reads for which both pairs successfully aligned were considered. The gene counts were extracted using the HTSeq python tool[43]. Differential expression analyses were performed using the EdgeR package[44] using empirical Bayesian methods. To filter out weakly expressed genes, only those genes with a minimum expression level of 1 RPKM (reads per kilobase per million mapped reads) in three replicates were included in the analysis. Genes with a LogFC above 1 (2-fold change) and false discovery rate (FDR) of below 0.05 and P-value below 0.05 were considered differentially expressed between conditions. To assess the variability among samples, we performed hierarchical clustering and dispersion analysis based on biological coefficient of variation. Hierarchical clustering was performed based on Euclidean distances. Dispersion was conducted using top 2000 values in the EdgeR software package.

Functional Classification Analysis

To annotate entire gene sets of the sorghum and *C. sublineolum* genome accurately, all protein sequences were analyzed using InterProScan 5.8-49.0[45]. We then used agriGO and ReviGO[46,47] to identify the putative biological functions and biochemical pathways for DEGs and find statistically overrepresented GO terms. For expanding our functional analysis of DEGs, we used MapMan software to visualize and biochemical pathway overlays as previously described[48]. For Mapman analysis, all genes' identification labels were converted into Sbicolor_79 label based on Sbicolor 3.1 annotation files (PhytozomeV10: Sbicolor_313_v3.1. synonym). Surveillance DNA Isolation and Whole Genome Sequencing Among the RILs, 50 resistant and 50 susceptible plants were selected for constructing two DNA bulks (resistance bulk, RB; susceptible bulk, SB). For building the reference sequence, 10 sorghum cultivars (Table 2) were sequenced. For DNA extraction, 100 mg fresh leaf was harvested from each selected seedling and DNA was isolated using a DNeasy Plant Mini Kit (Qiagen, USA). About 100 ng DNA of each sample was combined for constructing two independent bulk DNA. The two DNA bulks were purified with the DNA clean-up & Concentration Kit (ZYMO Research, USA). A genomic DNA library was prepared for each DNA bulk using the Illumina TruSeq DNA Sample Preparation Kit (Illumina Inc, San Diego, Calif., USA) according to the manufacturer's protocol. Each DNA library was sequenced using an Illumina Hiseq 2500 sequencing platform. All raw sequencing data have been deposited in the SRA database with accession number.

Bulk DNA Sequencing and QTL Analysis

The raw DNA-seq reads were trimmed and filtered to remove low-quality sequences using Fastx-tools[49]. Reads with a quality threshold lower than 30 and those shorter than 40 bp were discarded. The short reads from the two DNA bulks that passed the quality control were aligned to the reference genome of BTX23 (Phytozome V10: Sbicolor_313_v3.1) using BWA software[50]. Reads that aligned to more than one position in the reference genome were filtered out. Files were converted to BAM files using SAM tools[51], sorted and then compared to locate duplicate records using Picard software (http://picard.sourceforge.net). Re-alignment (BAQ) was done to avoid false SNP calls near indels. The resulting files were applied to GATK SNP-calling[52,53]. SNP annotation was used SnpEff (Version 4.1)[17] with the sorghum annotation file (PhytozomeV10: Sbicolor_255_v2.1.gene.gff3). A total of 11,170 variants, including 9,567 SNPs, 755 insertions, and 848 deletions, were annotated in the QTL region. QTL analysis was followed as previously described[16]. The sorghum reference sequence was reconstructed by replacing nucleotides in BTX623 with the 1,826,960 SNP positions identified between eight cultivars by alignment of the short reads to the reference genome of BTX623 (PhytozomeV10: Sbicolor_313_v3.1). SNP-index was calculated at all SNP positions with Coval. All the steps were manipulated using QTL-seq_framework1.4.4 pipeline[16]. Slide window analysis was applied to SNP-index plots with 2 Mb window size and 50 kb increment.

ChIP-qPCR

Chromatin immunoprecipitation (ChIP) experiments were performed as described previously with minor modifications[54]. Leaf tissues (1.5 g) from 3-week-old plants were fixed with 1% (v/v) formaldehyde for 40 minutes at room temperature, and the chromatin samples were sonicated to yield fragments of 200-1,000-bp. After pre-clearing of the chromatin samples with salmon sperm DNA/protein A agarose beads (EMD Millipore), immunoprecipitations were carried out with the appropriate antibodies to histone lysine methylation and reverse cross-linking overnight at 65° C. Immunoprecipitated DNA samples were purified using the silica membrane column (MACHEREY-NAGEL Inc.) and eluted in 60 µL elution buffer. In qPCR, 2 µL of DNA was amplified using SYBR Green Supermix (Bio-Rad) with specific primers as listed in Supplemental Table S6. The data is presented as percentage of input values. The antibodies used for the ChIP experiments were: H3K4me2 (07-030, EMD Millipore), H3K4me3 (07-473, EMD Millipore), H3K9me2 (ab1220, Abcam), H3K9me3 (07-442, EMD Millipore), H3K36me2 (07-369-I, EMD Millipore), H3K36me3 (ab9050, Abcam), and IgG (sc-2027, Santa Cruz) as a negative control.

Semi-Quantitative RT-PCR Analysis

Total RNA was extracted from leaves of 4-week-old sorghum plants inoculated with *C. sublineolum* with TRI reagent (Molecular Research Center Inc.), according to the manufacturer's instructions. After DNase I (Promega) treatment, reverse transcription was performed with 2 µg of total RNA using the M-MLV Reverse Transcriptase (Promega). The PCR reaction for ARG1 and Actin genes consisted of 25, 28, 31, and 34 cycles in 3 steps: 94° C. for 30 sec, 57° C. for 30 sec, and 72° C. for 2 min (ARG1 gene) or 30 sec (Actin gene). Amplified PCR products were loaded on 1.5-2.0% agarose gels and bands were visualized by ethidium bromide staining. The primers are shown in Table 5.

DNA Methylation Analysis

Leaves of three plants per line were selected for DNA isolation. DNA was extracted from four-week-old leaves using a DNeasy Plant Mini Kit (Qiagen), and DNA (200 ng) was used for bisulfite conversion using EpiTect Bisulfite kit (Qiagen). The converted DNAs were used for methylation-specific PCR (MSP) reactions to evaluate the methylation status of ARG1, CARG and Actin genes using two primer sets: one reaction specific for methylated DNA and another specific for unmethylated DNA. The primers were designed using MethPrimer. The amplification conditions were 95° C. for 5 min, 40 cycles of (95° C. for 30 sec, 63° C. for 30 sec and 72° C. for 30 sec), and 72° C. for 3 min. Amplified PCR products were analyzed on 2.0% agarose gels and bands were visualized by ethidium bromide staining. The primers are shown in Tables 5. All the PCR reactions were replicated at least two times.

The amplified products were gel purified (Gel Extraction kit; MACHEREY-NAGEL Inc.), ligated into the pGEM®-T Easy Vector (Promega), and transformed into *Escherichia* coli. The plasmid DNAs were isolated and sequenced using the T7 or M13 forward primers.

Small RNA-Seq Analysis

We applied an informatics pipeline for filtering plant miRNAs from the complete set of small RNAs. A total of 228,228,937 distinct small RNAs reads were analyzed using the pipeline from twelve sorghum libraries with Cs or mock inoculated plants. As a first step, the adaptors and low quality reads were removed out using FASTX-Toolkit[55]. The next step was removing out structural RNAs such as tRNAs and rRNAs. The third step was selecting the RNA read sizes between 18 nt and 28 nt. The fourth step was to remove low abundance small RNAs (retaining only those with less than ten transcripts per million in at least one of twelve libraries), C. sublineolum genome reads, as well as highly repetitive small RNAs (those with more than 20 hits to genome) were discarded. A total of 121,338 distinct small RNAs were retained. Finally, miRDeep-P[56] was employed to detect predicted miRNAs. In order to identify consistent miRNAs, all small RNA libraries were separately processed based on the above method. miRNAs were considered as candidate miRNAs if they could be detected in three libraries with the same treatment in SC283 or TAM428. In order to furtherer verify our predicted miRNA, high similarity homologs in miRBase V21 were identified using Segemel[57]. miRNAs that can pass all filter processing were identified as novel miRNA. All small RNA-seq reads were aligned against the reference genome of BTX623 (PhytozomeV10: Sbicolor_313_v3.1) using the software Tophat 2[42].

Example 1. The Sorghum Line SC283 Displays Broad-Spectrum Resistance to Sorghum Anthracnose caused by *Collectotrichum sublineolum*

Figures 1, 1A, 1B, 1C, 1D, 1E, 1F:
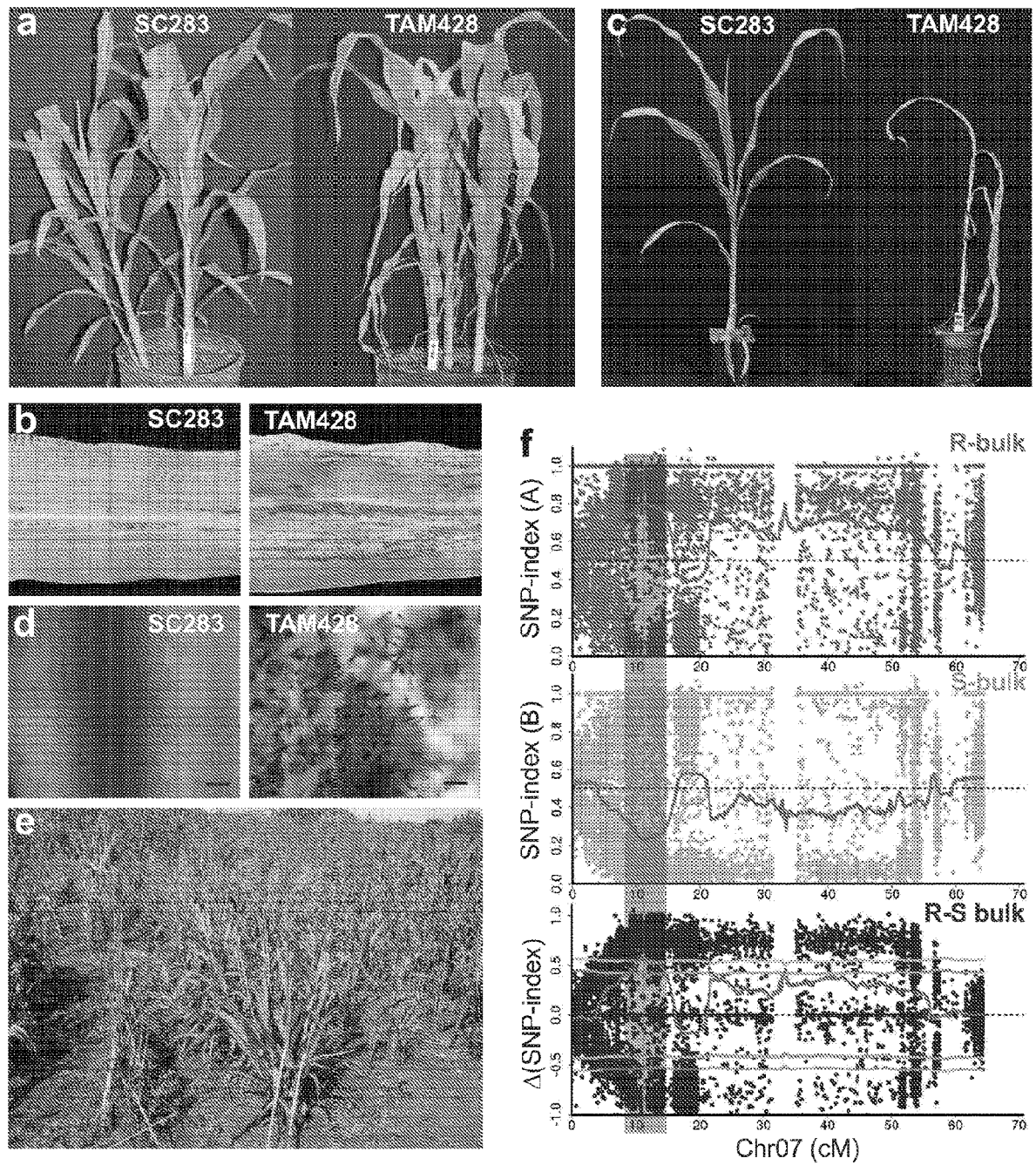
FIG. 1. Disease responses of sorghum SC283 and TAM428 lines to *Colletotrichum sublineolum* and identification of the resistance locus.
(FIG. 1A and FIG. 1C) Disease response phenotypes at 7 dpi (days post inoculation) (FIG. 1A), and 14 dpi (FIG. 1C).
(FIG. 1B) Disease symptom on infected leaves at 10 dpi, (FIG. 1D) Trypan blue staining of *C. sublineolum* inoculated leaves showing fungal structures on TAM428 but a lack of fungal growth in SC283. Inoculated leaf tissues were stained with trypan blue and samples were examined under microscope to visualize fungal material.
(FIG. 1E) Resistance of SC283 to foliar pathogens in the field under natural infestation. The experiments were repeated at least three times with similar results. The disease response data shown in A-D are from Cs strain Cgsl2 inoculated plants.
(FIG. 1F) Identification of anthracnose resistance QTL in SC283 though QTL-seq analysis of recombinant inbred lines. Single nucleotide polymorphism (SNP)-index plots of R-bulk (top) and S-bulk (middle), and Δ (SNP-index) plot (bottom) of chromosome 7 with statistical confidence intervals under the null hypothesis of no QTLs (green, P<0.05; yellow, P<0.01). The Δ (SNP-index) plot obtained by subtraction of S-bulk SNP-index from R-bulk SNP-index for RILs.

Diverse sorghum natural variants collected from different regions of the world were screened for resistance to the hemibiotrophic fungal pathogen *Collectotrichum sublineolum* (Cs) by inoculation with a high concentration of spore suspension and incubation under conditions that favor disease in the greenhouse. The sorghum genotype SC283 was resistant to eleven different Cs isolates from the US and Africa, suggesting broad-spectrum resistance (FIG. 1, Table 1). The inoculated SC283 leaves remained healthy and displayed resistance responses with the hypersensitive response (HR) after inoculation with the Cs strain Cgsl2 (FIG. 1a,b). In contrast, a widely known susceptible line, TAM428 lacked any apparent resistance response and showed extensive disease lesions, massively chlorotic leaf areas and complete tissue collapse (FIG. 1a,b). At 2 weeks after inoculation, SC283 remained healthy with no symptoms of infection, whereas TAM428 plants were killed by the fungus (FIG. 1c). Microscopic analysis of inoculated tissue after trypan blue staining revealed restricted fungal growth in SC283 but extensive growth in TAM428 (FIG. 1d). Interestingly, SC283 also manifested enhanced disease resistance to anthracnose and other fungal diseases under natural infestation in Ethiopia (FIG. 1e). The experimental site in Ethiopia has high incidence and severity of foliar diseases including rust and anthracnose.

Example 2. Identification of Fungal Resistance Locus Through Whole Genome Resequencing Recombinant inbred populations (RILs) generated by crossing SC283 and TAM428 were used to identify the resistance locus in SC283 through whole genome sequencing approaches that combined bulked segregate analysis (BSA) and whole genome sequencing[16]. Disease responses of 217 RILs were tested in the greenhouse and both resistant and susceptible RILs similar to the parental SC283 and TAM428 were recovered (data not shown). Among these, fifty resistant and 50 susceptible individual plants were selected, based on six rounds of independent disease assays. A pair of DNA bulks was constructed by pooling DNA from 50 resistant and 50 susceptible RILs that were then sequenced using Illumina Hiseq 2500. More than one billion paired-end reads were obtained, including 494 million resistant bulk (RB) reads and 513 million susceptible bulk (SB) reads (Table 2). These paired-end short reads covered the sorghum genome at an average depth of 66× and 68× in the RB and SB bulks, respectively. In parallel, a reference sequence was built by sequencing eight sorghum cultivars, including the two parental lines of the RILs used in this study (Table 2).

Figure 11A:
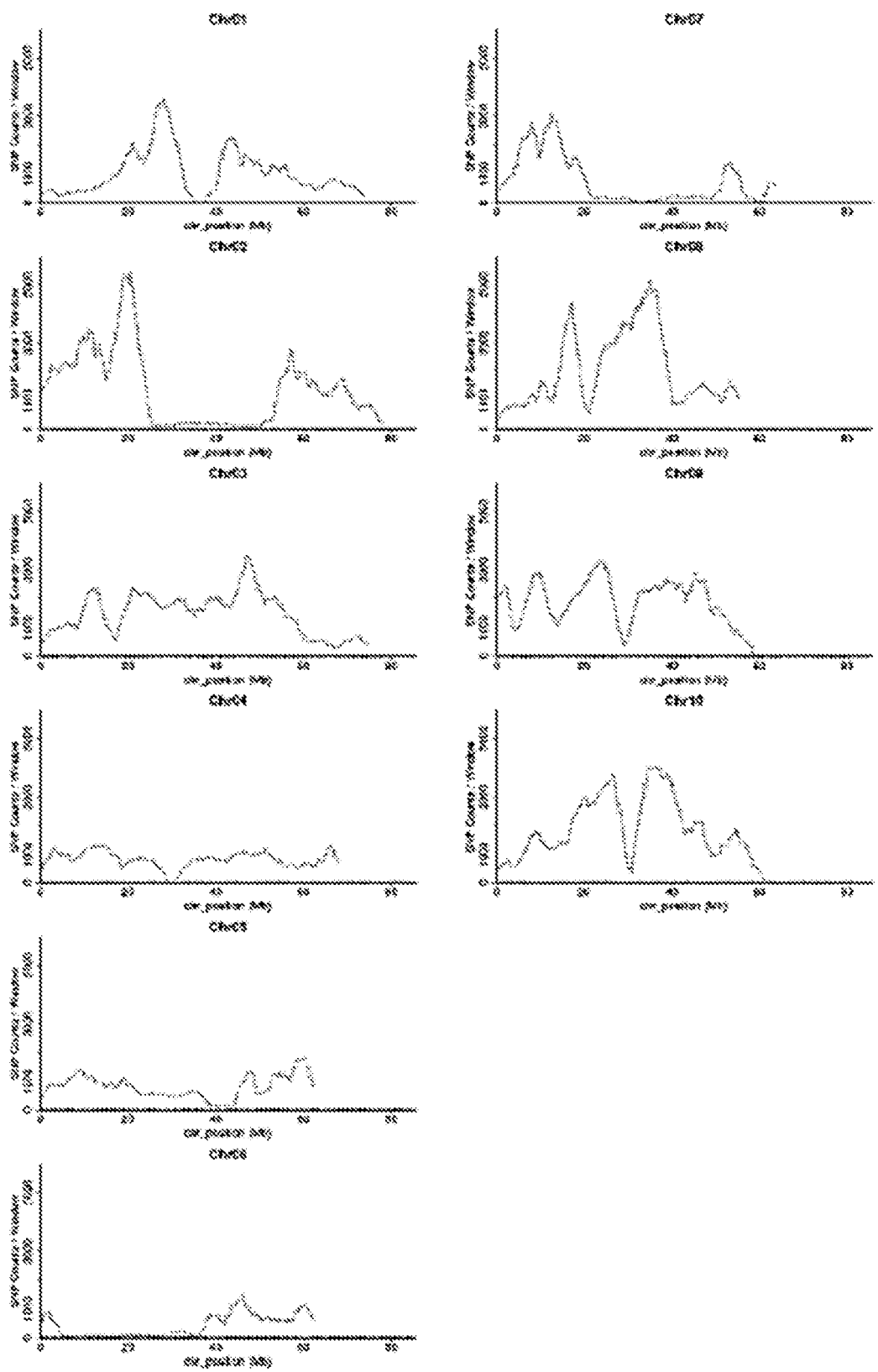
Figure 11B:
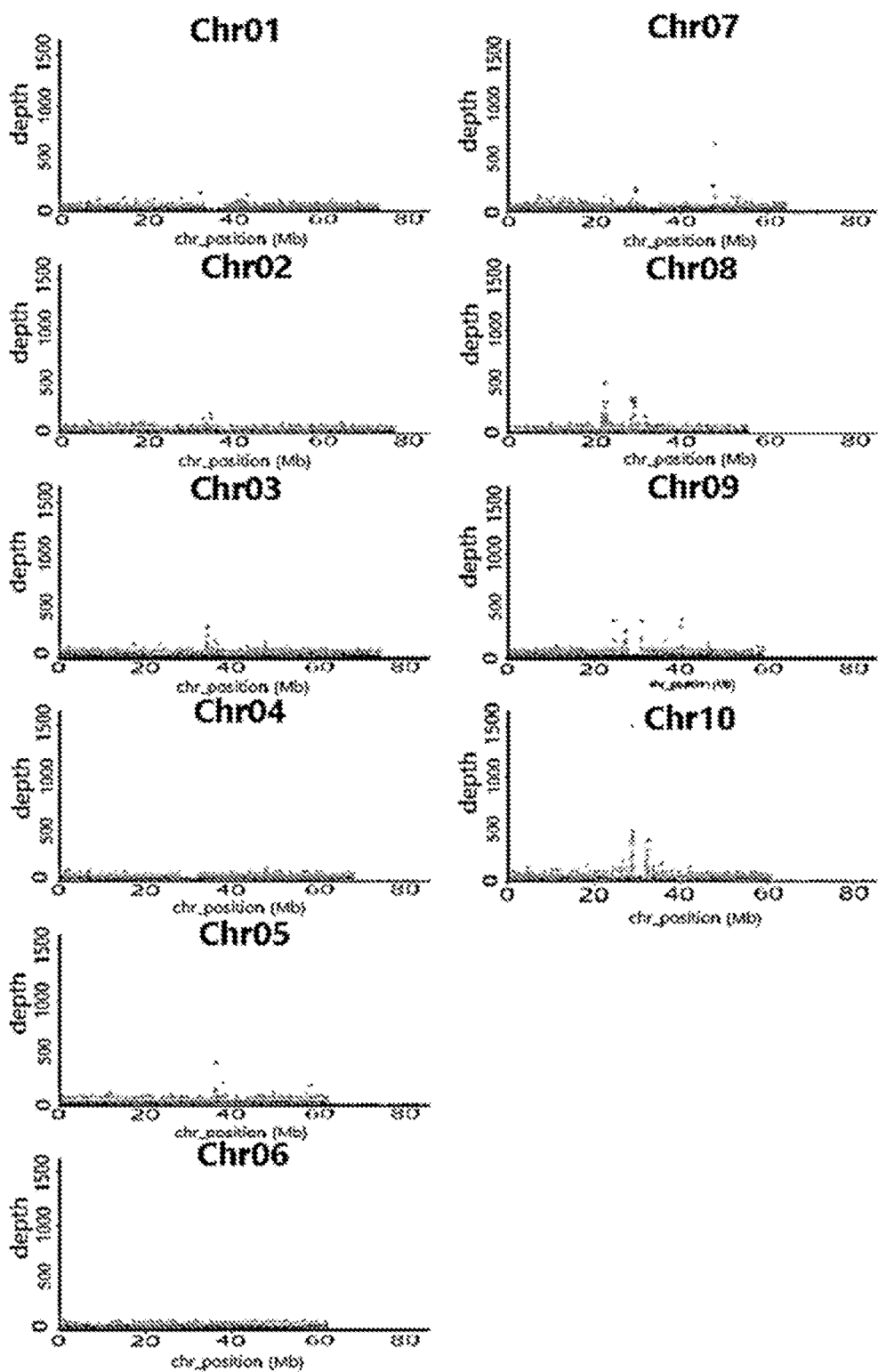
Figure 11C:
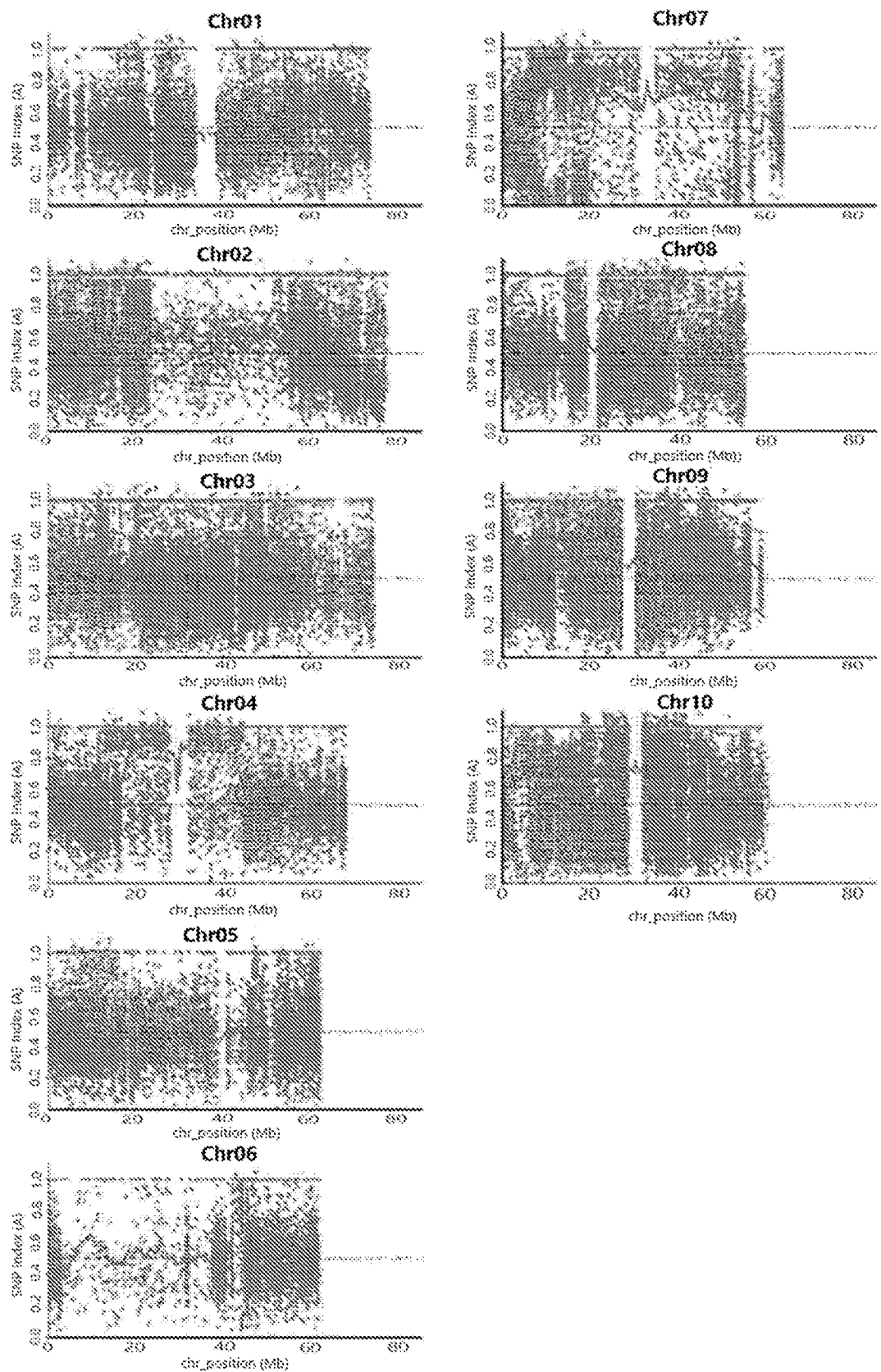
Figure 11D:
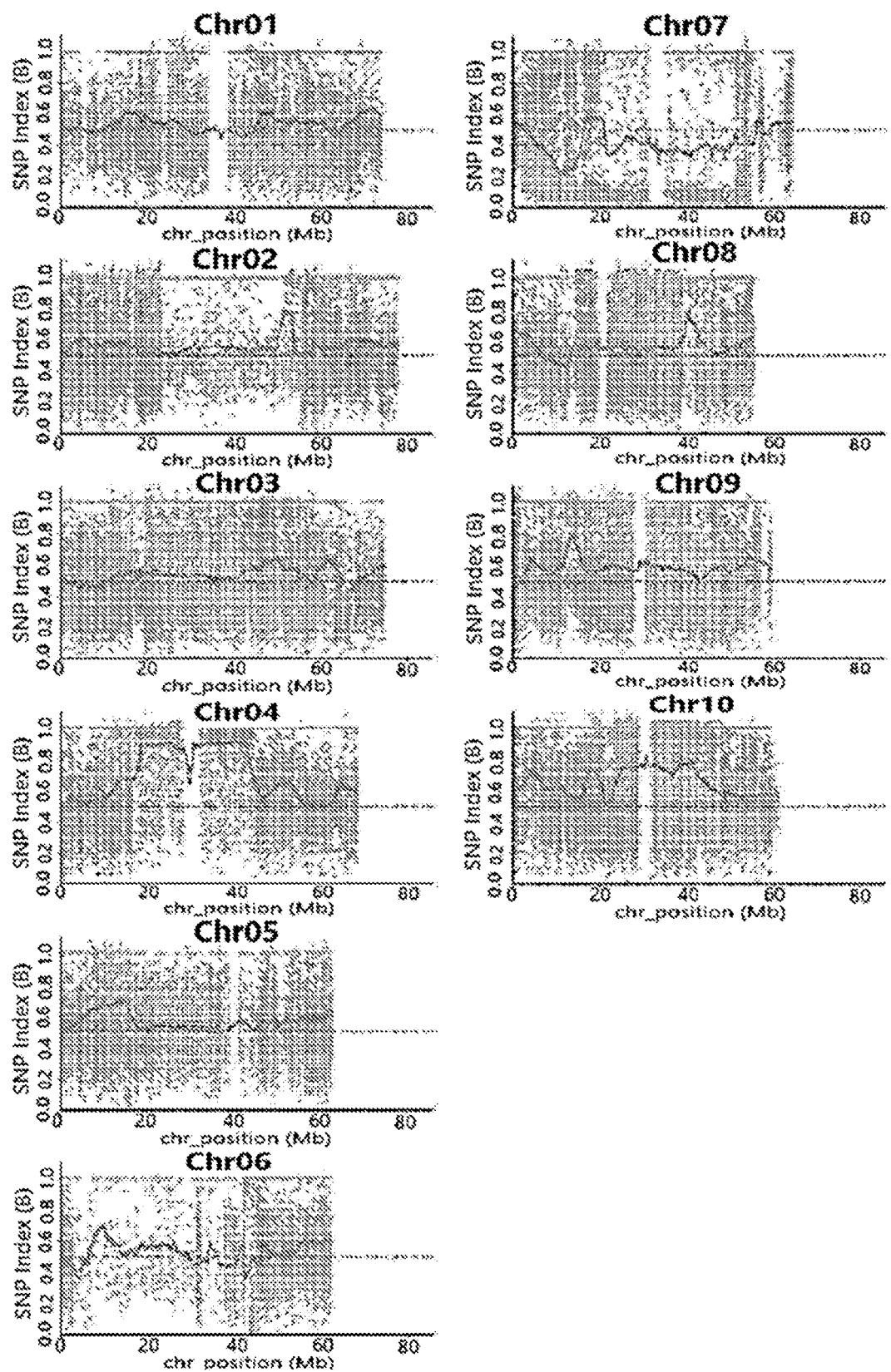
Figure 11E:
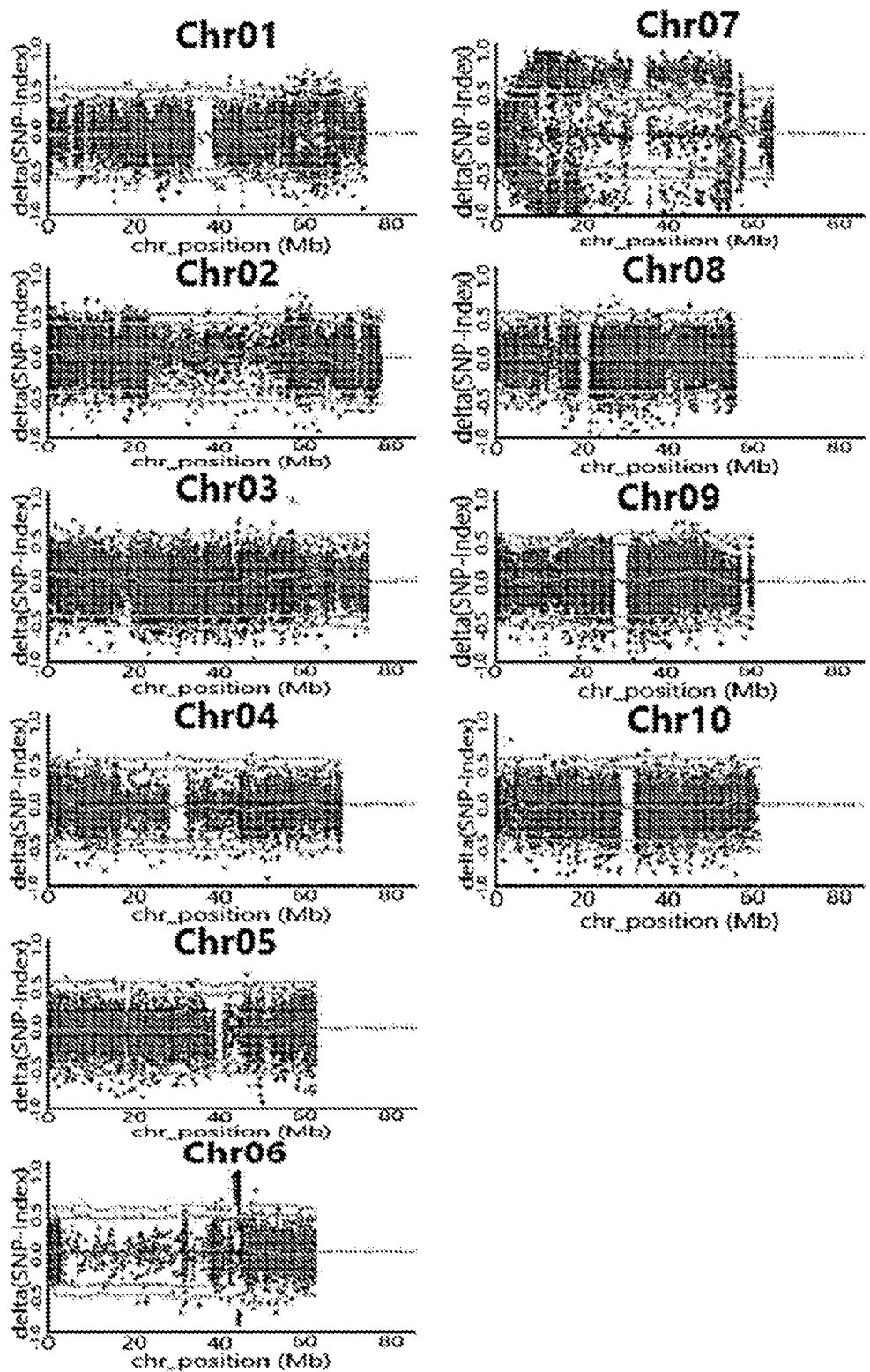

To determine the genomic region associated with resistance, we conducted Quantitative Trait Loci (QTL)-seq analyses using the sequence data from the RB and SB. QTL-seq relies on an estimation of the Single Nucleotide Polymorphism (SNP) index in the RB and SB sequences in order to identify genomic region harboring the major QTL. More than 3 million SNPs were identified based on mapped reads for QTL analysis and these SNPs were unevenly distributed in the genome. The SNP-index of each SNP was determined using QTL-seq pipeline (FIG. 11)[16]. Then the Δ (SNP-index) was calculated on the bases of subtraction of the SNP-index of SB from that of RB (FIG. 1f and FIG. 11e). As expected, the Δ (SNP-index) was zero in most genomic regions, but a few regions exhibited positive or negative values, indicating differences with the reference genome (FIG. 11e). A Δ (SNP-index) higher than 0.44 was observed in the region from 7.15 to 15.80 Mb on Chromosome 7 with P<0.05 under the null hypothesis (FIG. 1f and FIG. 2a). This contrasting pattern of the SNP-index for RB and SB defined a major Cs resistance locus (FIG. 1f and FIG. 11e). In the QTL region from 7.15 to 15.80 Mb on Chromosome 7, all of the resistant RILs carried the SC283 genomic sequences, whereas all of the susceptible RILs contain the TAM428 genomic regions (FIG. 2b and FIG. 12).

Example 3. Identification of Candidate Resistance Gene(s) in the QTL Region

To identify the specific Cs resistance gene, SNPs, insertions and deletions in the QTL region were annotated (see Methods) after filtering the low quality sequences and SNPs with no polymorphisms in the parental lines[17]. Most variation was found in non-coding genomic regions and exhibited no correlation with disease phenotypes. However, 916 sequence variants were mapped to exons, 3'-UTR, and 5'-UTR of 143 genes in the QTL region (FIG. 13). The genomic organization and functional annotation data corresponding to the SNPs in the QTL region were closely analyzed (FIG. 2b). An 8 bp sequence deletion (GGCGACCT) in the first exon of Sobic.007G085350 at position 10,793,251 on Chromosome 7 was identified in the resistant parent SC283 that was not present in the sensitive parent TAM428 (FIG. 2c). The deletion in Sobic.007G085350 in SC283 was also present in RB, but absent in both TAM428 and the SB sequence (FIG. 2, and FIG. 12). Based on these genetic data, the polymorphism at Sobic.007G085350 was considered to be the candidate sequence change underlying the resistance phenotype in SC283. Sobic.007G085350 is predicted to encode a polypeptide of 79 amino acids with unknown function, but no protein product was detected based on our proteomic analysis. Further, this putative polypeptide is unique to sorghum with no significant sequence homology identified in any protein database (data not shown). The likely non-coding corresponding NAT gene is designated CARRIER OF ATHRACNOSE RESISTANCE GENE1 (CARG). Interestingly, however, a second gene, Sobic.007G085400, is nested in the intron of Sobic.007G085350 (FIG. 2b). The Sobic.007G085400 gene encodes a canonical NLR with N-terminal nucleotide binding (NB) and C-terminal leucine rich repeat (LRR) domains (Table 4), making it an excellent candidate, and is hence designated ATHRACNOSE RESISTANCE GENE1 (ARG1). This class of proteins function as intracellular receptors for virulence effector proteins and are key determinants of ETI[18]. The susceptible TAM428 genotype contained a sequence polymorphism that introduced a premature stop codon in the region preceding the LRR domain (FIG. 2c). This ARG1 sequence variation in the susceptible genotypes is linked to an intact CARG gene.

To verify candidate resistance QTLs identified by QTL-seq, sequence-specific PCR markers flanking the sequence deletion in CARG (Sobic.007G085350) were used to analyze co-segregation with the disease responses. The deletion in CARG co-segregated with the resistance phenotype in all the resistant RILs, which provided additional evidence that the polymorphism in CARG is linked to resistance on the same region of chromosome 7 (FIG. 2d). To provide further genetic evidence for a link between the observed phenotype and sequence variation in the resistance locus, whole genome sequences of sorghum genotypes available in the public database were searched to identify additional alleles in the CARG-ARG1 locus. Sorghum lines carrying independent deletions and/or SNPs in the CARG and ARG1 genes were identified from analysis of 81 deep sequenced cultivars, land races, and wild sorghums available in the database tested for disease resistance (FIG. 2c and Table 3). Among the fifteen additional sorghum lines examined, BTX378, KS115, SC35, PI585749, PI586439, and Greenleaf carried the same 8 bp deletion in CARG and intact ARG1 as were observed in SC283 (FIG. 2c). PI585749, PI586439 and Greenleaf carried additional sequence alterations in the CARG gene that are distinct from SC283. On the other hand, all the nine additional sorghum genotypes examined carried intact CARG and ARG1 mutant allele with premature stop codon identical to TAM428 (FIG. 2c).

In addition, the resistant and susceptible RILs as well as the additional alleles from independent sorghum lines were genotyped and their disease responses tested (FIG. 3). The resistance phenotype was observed in the leaves of the resistant RILs and the genotypes carried intact ARG1 but the exception to resistance phenotype displayed on the Greenleaf (FIG. 3b,d). Typical disease symptoms such as chlorotic and necrotic lesions and black spots caused by fungal acervuli (the reproductive structures) appeared to a greater or lesser degree in the susceptible RILs and the genotypes having ARG1 mutant allele (FIG. 3b,d). In comparison, the susceptible genotypes, TMA428, BTX623, Tetron, SQR, PQ434, KP33, ZZZ, and IS9830 showed more severe and advanced disease symptom, while 555 and SRN39 showed mild disease symptom. To determine the relationship between disease symptom and fungal growth, we quantified the fungal growth by using quantitative real-time PCR (qPCR) amplification of the internal transcribe spacer (ITS) region of the fungal ribosomal DNA (rDNA). Overall, fungal growth was identical to disease symptom (FIG. 3e).

These analyses confirmed the sequence data obtained from the database and the disease responses of these mutants were consistent with the genotypes of the TAM428 and SC283 genotypes. Thus, among the genes that map to the QTL region, only the CARG ARG1 gene pair showed consistent sequence polymorphism between the two parental lines and the resistant and susceptible RILs and these genetic association were confirmed using independent sorghum genotypes.

Example 4. The Antisense Regulated ARG1 Gene is the Anthracnose Resistance Gene

Analyses of the genomic organization of CARG ARG1 locus revealed that CARG has two exons, interrupted by two introns, the second of which is quite large. The ARG1 coding region is embedded in this large second intron. In addition, the 5'-UTR of ARG1 overlaps with the 3'-UTR of CARG (FIG. 4a).

RNA-seq analysis of pathogen or mock-inoculated resistant and susceptible lines revealed that SC283 displayed significantly more transcript reads that mapped to ARG1 and significantly fewer that mapped to CARG (FIG. 4a-c). The basal expression of ARG1 was significantly higher in SC283, with further increases after Cs inoculation, while CARG expression was significantly lower before and after infection (FIG. 4b). In contrast, TAM428 exhibited higher CARG expression and much lower ARG1 expression than did SC283 (FIG. 4c). The ratio of expression of ARG1 and CARG was only two fold in the susceptible TAM428 line, compared to at least a 250-fold difference in SC283 based on RNA-seq data (FIG. 4b,c), further supporting the hypothesis that the loss of CARG transcript in SC283 due to the deletion polymorphism results in enhanced expression of ARG1. Mapping of the reads reveal the exon and intron boundaries, which was verified using RT-PCR (FIG. 3a).

The gene expression pattern observed from the RNA-seq was confirmed using quantitative reverse transcription PCR (qRT-PCR) with primers that flank introns in both the CARG and ARG1 genes. In resistant genotypes carrying the CARG deletions, the expression of ARG1 is significantly higher than in lines where CARG is normally expressed. However, despite the CARG mutation in Greenleaf, low level of ARG1 expression was observed both prior to and after Cs infection (FIG. 4d and FIG. 14a). Primers flanking the second CARG intron confirmed CARG expression in the susceptible genotypes and the RILs SSD50, SSD61, and SSD65, all of which exhibited significantly higher levels of expression of CARG than is observed in resistant genotypes (FIG. 4e and FIG. 14b). A second primer pair flanking the first intron of CARG gave similar results (FIG. 14c). In every case with exception of Greenleaf, alleles that abrogate CARG gene expression enhance both ARG1 expression and resistance to anthracnose (FIG. 3b,d). The above data demonstrate that the CARG -ARG1 locus determines resistance in SC283 and other resistant sorghum genotypes. Intriguingly, it appears that resistance results from both the loss of cis-NAT CARG transcript and a concomitant increase in expression of an intact ARG1 allele in the resistant genotypes.

Example 5. The ARG1 Allele in Susceptible Genotypes Express Alternatively Spliced Transcripts Encoding Truncated NLRs To further confirm the RNA-seq findings of ARG1 expression patterns in response to Cs infection, semi-quantitative RT-PCR analysis was performed using primer set for full-length amplification of ARG1. The transcript levels of ARG1 in SC283 and TAM428 displayed a good correlation with the RNA-seq data. In genotypes with CARG polymorphism causing loss of its transcript, a single pathogen inducible ARG1 transcript is observed. However, genotypes that express NAT produce two variant ARG1 transcripts, both of which are pathogen inducible (FIG. 5a). We sequenced all ARG1 transcripts from SC283 and TAM428 to determine the nature of the splice variants of the ARG1 transcript. Interestingly, the larger variant is comparable in size to the ARG1 in the resistant genotypes but it has a stop codon in the middle of gene as noted in FIG. 2c (FIG. 5b and FIG. 15). The second transcript is much smaller and skips the LRR domain and thus retains only the NBs-ARC domain. To validate this, we first analyzed alternative splicing of ARG1 across all genotypes tested for disease assay in our research. This result showed genotype-specific alternative splicing of ARG1 that is all susceptible lines have two different ARG1 transcripts, while all resistance lines have single transcript of ARG1 (FIG. 5c).

We next assessed the genetic relationship of ARG1 gene among many resistant and susceptible lines for which sequences were available from the database and sequencing data. Phylogenetic relationship inferred from Maximum-likelihood analysis revealed a clear separation between the resistant and susceptible lines (FIG. 16a). The resistance lines form three sub-clusters; SC283, Greenleaf, SC35C, and BTX378 form one sub-cluster, while PI585749 and PI586439 form another sub-cluster not closely related to SC283 as shown by the large distance in the phylogenic tree. The last sub-cluster has only KS115 which also displayed large distance from the SC283. The susceptible lines build five sub-clusters; TAM428 and twenty-nine susceptible genotypes make one sub-cluster and 555, Tetron and KP33 were sub-clustered to be close to TAM428. In contrast, third sub-cluster PQ434 and firth sub-cluster SQR and Ai4 were not closely related to TAM428 as shown by very large distances in the phylogenic tree. The last sub-cluster comprised only PI525695 which also displayed very large distance from the TAM428. These results suggest that the presence of variation among sorghum genotypes in the resistance responses to fungal pathogens.

The ARG1 sequence alignment of the 44 genotypes showed the resistant lines carry intact ARG1 and were closely identical to SC283 whereas the susceptible lines were identical or nearly identical to TAM428 carrying ARG1 genomic sequence with a premature stop codon (FIG. 16b).

Figures 6A, 6B, 6C:
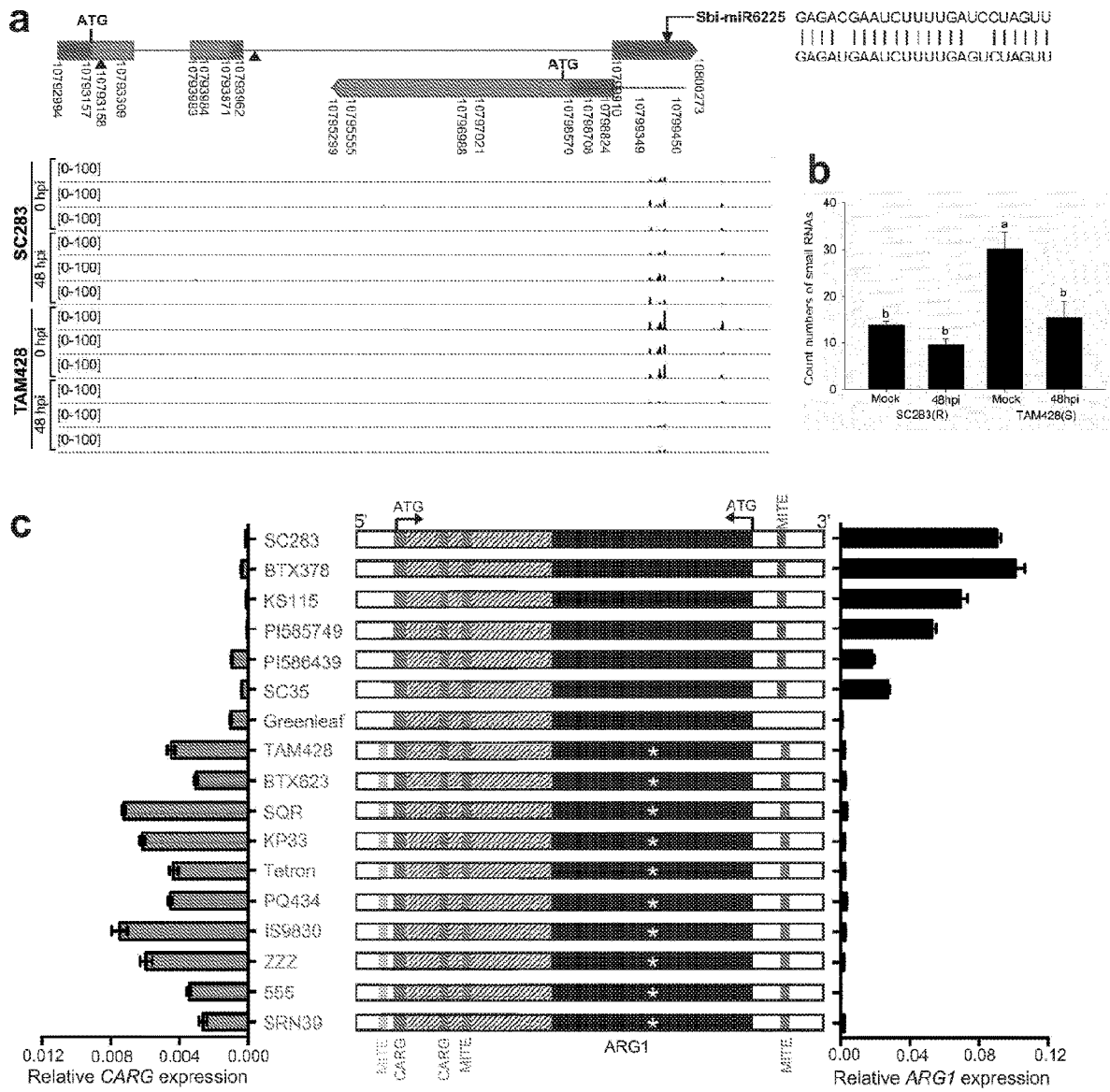

Example 6. The ARG1 and CARG Complementary Region Produces Small RNAs and CARG/ARG1 Overlap Region Regulates the ARG1 Expression via MITEs ARG1-CARG locus have an interesting genomic structure. The entire coding sequence of ARG1 is embedded in the intron of CARG. The 5'-UTR of ARG1 overlaps with the 3'-UTR of CARG (FIG. 3a), raising the possibility of an interaction between the two complementary transcripts. Small RNA profiling of healthy and infected SC283 and TAM428 was conducted to identify small RNA (sRNA) sequences that map to the CARG ARG1 region that may regulate gene expression. Comparison of sRNAs in the two genotypes identified a cluster of sRNAs from a portion of the 3'-UTR of CARG. These sRNAs are likely derived from a high copy number Miniature Inverted-repeat Transposable Element (MITE) in this region (FIG. 17). Interestingly, this MITE shows similarity to a hairpin variant of the MITE that expresses a pre-miRNA that is processed into sbi-mi6225 (miRBase, Verson 21), which is quite similar to the small RNAs present at CARG. Interestingly, the sRNAs showed significantly higher basal expression in TAM428 relative to SC283, suggesting that at least some of these small RNAs are derived from this locus and may have a role in up- or down-regulation of ARG1 and CARG in the sorghum (FIG. 6a). There are two MITE insertions flanking the CARG and ARG1 locus (FIG. 6c, FIG. 17). These two MITE sequences show very low sequence identify revealing their distinct nature (FIG. 18).

In general, MITE insertions have been shown to be associated with reduced gene expression. However, it does not exclude the possibility of that some MITE insertions can positively regulate gene expression. To evaluate the effect of MITE on gene expression, the CARG-ARG1 locus were examined to discover MITE sequences in various sorghum genotypes. Significant differences were observed in the insertion patterns of MITEs between the resistant and susceptible genotypes. Among them, the susceptible genotypes have 275-, 151- and 248-bp MITE insertions in the 5'UTR, second intron and 3'UTR (CARG/ARG1 overlap region), respectively, whereas the resistance lines except for the Greenleaf have 151- and 420-bp MITE insertions in the second intron and 3'UTR (CARG/ARG1 overlap region), respectively (FIG. 6b). Surprisingly, in spite of resistance, the Greenleaf contains only the 151-bp MITE in the second intron which appears to have no polymorphism between the lines. The location of the MITEs relative to the CARG ARG1 genes is shown on FIG. 6b and FIG. 18.

The qRT-PCR analysis revealed high level of CARG transcripts in the susceptible lines with 275-bp MITE insertion in CARG 5'UTR than in the resistant lines with no MITE insertion in CARG 5'UTR, suggesting that the 275-bp MITE may enhance the CARG expression level. In the lines where the 420-bp MITE insertion in the 3'UTR of CARG (CARG/ARG1 overlap region), the ARG1 were more highly expressed (FIG. 6b). In contrast, the 248-bp MITE and no MITE insertions in the 3'UTR of CARG (CARG/ARG1 overlap region), no significant induced levels of ARG1 expression were observed (FIG. 6b). These results imply that the 420-bp MITE in the 3'UTR of CARG (CARG/ARG1 overlap region) may positively regulate ARG1 expression, whereas the 248-bp MITE may negatively regulate ARG1 expression.

Example 7. Discordant Genetic Inheritance, Function and Expression of CARG and ARG1

While the CARG deletion co-segregates with resistance, the CARG wild type allele is linked to reduced levels of ARG1 transcripts that encode truncated proteins, which may be the primary cause of susceptibility. To determine the genetic inheritance of the CARG ARG1 locus with disease resistance, the F1 and multiple selfed progenies from the TAM428×SC283 cross were examined. All the F1 plants were resistant. Out of 409 F2 single plants, 114 individuals were susceptible and 295 were resistant, with the CARG sequence deletion co-segregating with resistance. The values obtained from the analysis of the F2 segregation do not differ significantly from 3 resistant: 1 susceptible segregation ratio ($x^2=1.18$, $P<0.05$) suggesting the monogenic and dominant nature of the mutation causing Cs resistance. These results demonstrate that CARG-arg1 is a recessive allele and the carg-ARG1 allele is dominant for disease resistance. Thus, resistance to Cs is inherited as a dominant mutation that results in the loss of the CARG transcript and upregulation of an intact and functional ARG1 allele.

Figures 7A, 7B, 7C, 7D, 7E:
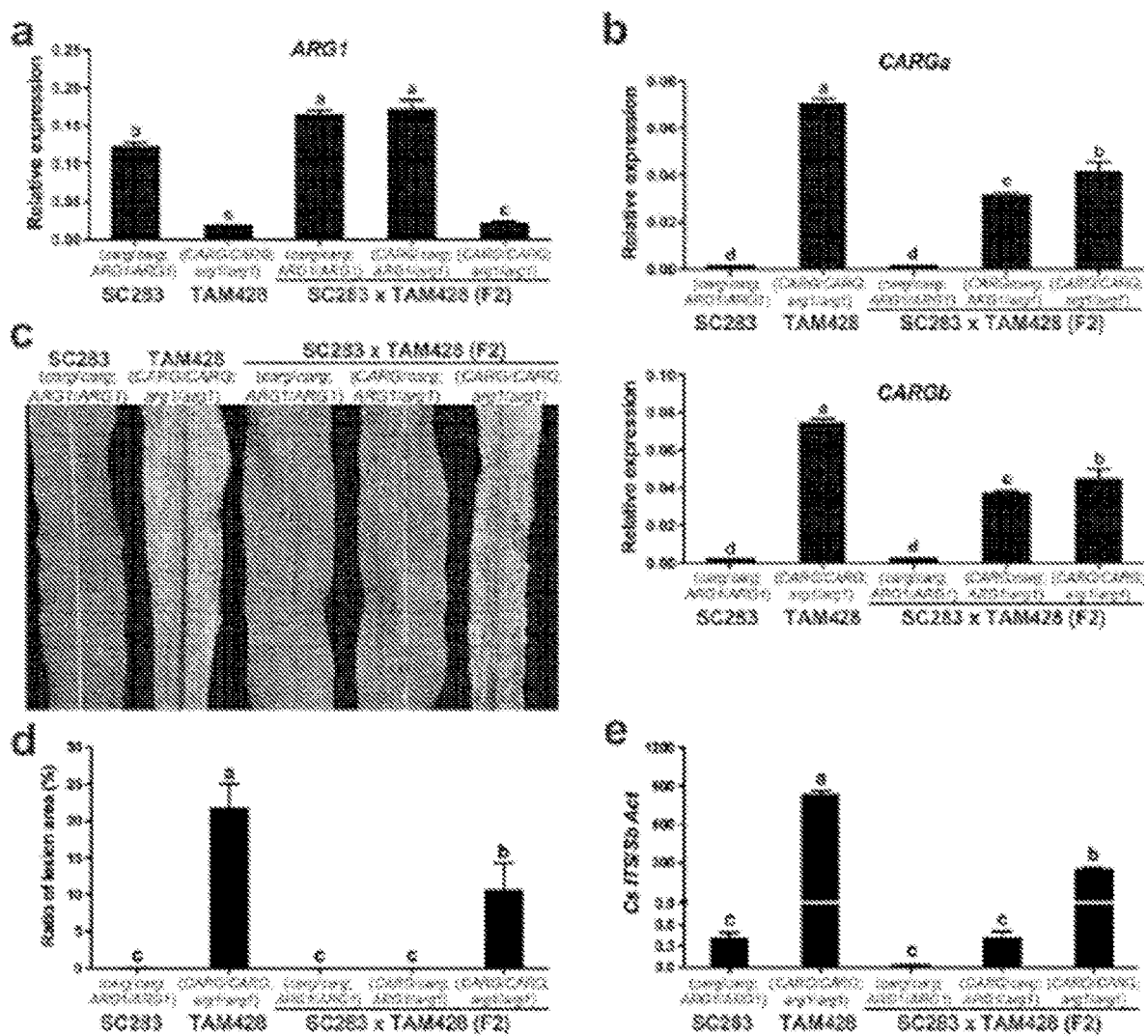

Individual F2 plants from the cross between SC283 and TAM428 were genotyped and plants carrying different CARG and ARG1 alleles were identified. Plants carrying the homozygous CARG deletion (carg/carg;ARG1/ARG1), CARG homozygous wild type (CARG/CARG;arg1/arg1), and heterozygous plants (CARG/carg;ARG1/arg1) were evaluated for gene expression and disease resistance (FIG. 7). In these genotypes ARG1 gene expression levels are negatively correlated with the CARG expression (FIG. 7a,b). However, in CARG/carg; ARG1/arg1 plants, the level of ARG1 expression was comparable to that in carg/carg; ARG1/ARG1 plants, despite an intermediate transcript levels of CARG (FIG. 7a,b). These results suggest that expression of one copy of CARG is insufficient to affect overall levels of ARG1 transcript.

The above F2 plants were also tested for Cs resistance by assessing disease symptoms and fungal growth. Interestingly, F2 carg/carg;ARG1/ARG1 and CARG/carg;ARG1/arg1 plants show comparable levels of resistance, having no disease symptom but the HR response. Both the TAM428 and the F2 CARG/CARG;arg1/arg1 plants display disease symptoms, including microscopic dark spots indicative of fungal acervuli (fungal reproductive structures) and chlorotic leaves, which were quantified by measuring the area of the disease lesion relative to the total leaf area (FIG. 7c,d). Fungal growth was quantified based on the qPCR amplification of the ITS region of the fungal rDNA. The F2 carg/carg;ARG1/ARG1 and CARG/carg;ARG1/arg1 plants were equally resistant based on both fungal growth and quantification of disease symptoms, and shared comparable levels of resistance with SC283 plants (carg/carg;ARG1/ARG1, FIG. 7d,e). The F2 CARG/CARG;arg1/arg1 plants were significantly more susceptible than the F2 carg/carg; ARG1/ARG1 and CARG/carg;ARG1/arg1 plants, but clearly less susceptible than the TAM428 plants carrying the same CARG/CARG;arg1/arg1 alleles (FIG. 7c-e). Similar differences were observed in disease symptoms and fungal growth when the various genotypes were drop inoculated in detached leaf assays (FIG. 19). These results suggest the presence of other factors in the SC283 background that modulate resistance. Overall, we find that resistance is associated with either partial or complete loss of CARG RNA, while susceptibility is primarily attributed to the loss of the wild type ARG1 allele.

Example 8. Chromatin Conducive for Expression at the ARG1 Locus is Correlated With Fungal Resistance To further understand how ARG1 gene expression is regulated, we examined histone H3 lysine methylation (H3Kme) patterns within CARG and ARG1 exons, a region upstream of CARG as well as the overlap region in resistant and susceptible genotypes. H3K4 and H3K36 methylation are generally associated with active transcription whereas H3K9 methylation is a repressive mark associated with transcriptional silencing[19] and is often linked to both DNA methylation and NAT-mediated regulation of gene expression[20]. In general, H3K9me2 is more prevalent in facultative heterochromain in gene rich regions and H3K9me3 is associated with constitutive heterochromatin.

Chromatin Immunoprecipitation (ChIP) was conducted using antibodies specific to H3K4, H3K36 and H3K9 di- and trimethylation, followed by qPCR designed to amplify precipitated products from the indicated regions of the ARG1 and CARG genes to determine the level of the chromatin modifications.

At the CARG/ARG1 overlap region, levels of H3K4me2, H3K4me3 and H3K36me3 were dramatically higher in the resistant genotypes SC283 and SSD4 and reduced in the susceptible genotypes TAM428 and SSD65 (FIG. 8b), closely tracking with the patterns of expression of this ARG1 gene. The chromatin of the ARG1 exon was also significantly enriched for H3K4me2, H3K4me3 and H3K36me3 in the resistant genotypes and were reduced in the susceptible genotypes, correlating with the loss of ARG1 expression in those genotypes. In contrast, H3K36me2 was enriched within the exon of ARG1 in the susceptible genotypes (FIG. 8c). Although H3K36 methylations are commonly associated with active transcription, previous studies reported that they are also implicated in alternative splicing. Here, we also observed alternatively spliced ARG1 transcripts in the susceptible genotype TAM428 (FIG. 5), this is the interesting correlation between H3K36 methylation and alternative splicing suggests that H3K36 methylation might have a role in regulation of alternative splicing in sorghum. Consistence with CARG gene expression, the exon of CARG contained much higher levels of H3K4m2, H3K4me3, H3K36me2, and H3K36me3 in the susceptible genotypes than the resistant genotypes (FIG. 8d).

Figures 9A, 9B, 9C, 9D:
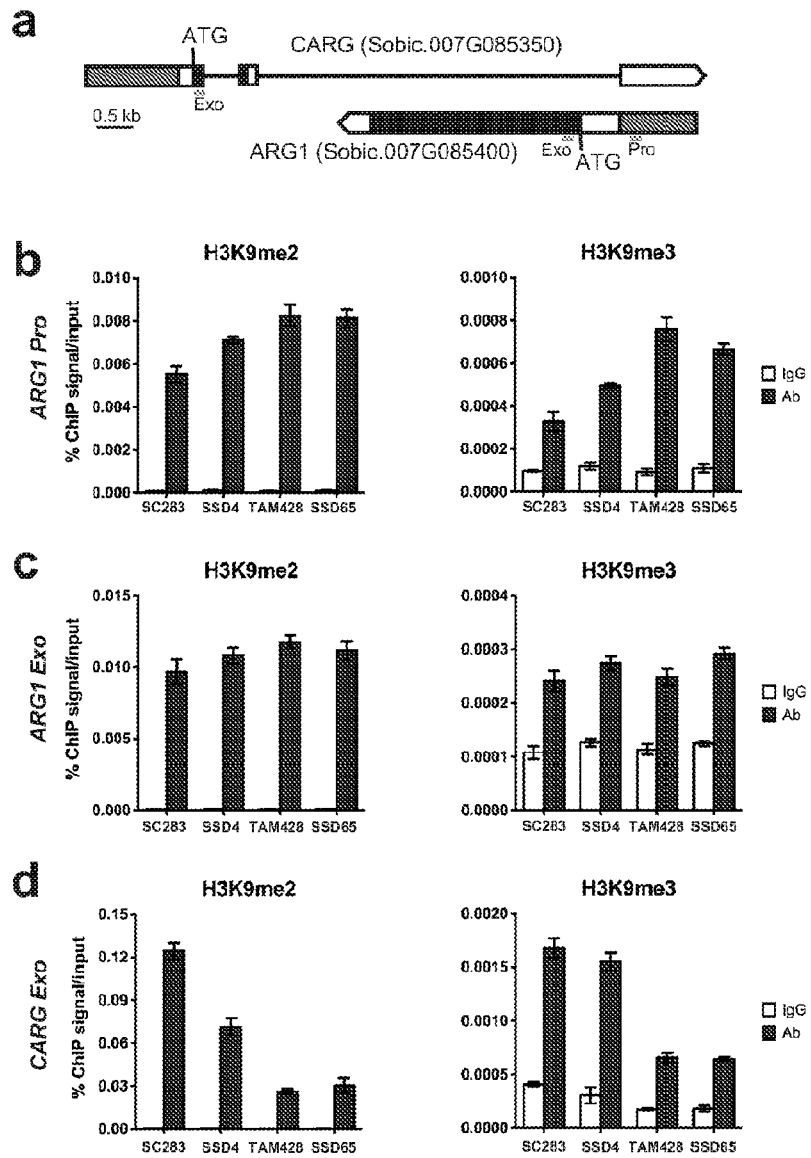

H3K9 methylation is a repressive mark that is triggered by small RNA[21]. In contrast to H3K4 and H3K36 methylation, H3K9me2 and H3K9me3 were higher in the CARG/ARG1 overlap region in susceptible genotypes, which exhibit lower ARG1 expression (FIG. 9b). However, there were no significant differences in H3K9me2 and H3K9me3 at the ARG1 exon in either genotype (FIG. 9c). H3K9me2 and H3K9me3 at the CARG exon were significantly increased in the resistant lines in which CARG expression is reduced, whereas low levels of H3K9 methylations at CARG exon were observed in the susceptible lines where CARG is highly expressed (FIG. 9d). In sum, H3K9 methylation at the CARG locus was lower in susceptible genotypes, which is consistent with their repressive function and low levels of H3K4me2, H3K36me2 and H3K36me3 in this region.

Due to the polymorphism of upstream region of CARG, histone H3 lysine methylations were not examined in the upstream region of CARG in both the resistant and the susceptible genotypes. In all cases, the control experiment was conducted on the same IP protein DNA complex using the primers at the constitutive sorghum Actin gene (Sobic.001G112600), which showed no difference in the level of histone H3 lysine methylation (FIG. 21). Overall, the patterns of histone lysine methylation correlated with gene expression patterns, but it is not clear if these are the causes or consequences of the reduced gene expression. In most cases, the H3K4 and H3K36 methylation levels are inversely correlated with DNA methylation in the exons. All susceptible genotypes showing lower ARG1 expression, also carried lower levels of H3K4 and H3K36 methylation, consistent with reduced gene expression.

Example 9. CARG Regulated ARG1 Confers Resistance to Fungal Pathogens With Distinct Pathogenesis Strategies NLR mediated resistance is often linked to plant immune responses to biotrophic and hemibiotrophic pathogens with race specificity[18]. To determine the specificity of ARG1, we tested the different genotypes for resistance to target spot, a fungal disease of sorghum caused by the necrotrophic fungus *Bipolaris sorghicola* (FIG. 21*a*). Unexpectedly, the plant responses observed for *B. sorghicola* were similar to the one for Cs. Similarly, ARG1 conferred resistance to sorghum rust disease caused by the biotrophic fungus *Puccinia purpurea* (FIG. 21*b*). This resistance is, therefore, broadly effective against three species of fungal pathogens with three distinct modes of action. Resistance to distinct groups of pathogens is unexpected given that NLR are a class of proteins that are generally linked to race specific resistance, and are even known to promote susceptibility to necrotrophic fungi[22]. To our knowledge, this is the first instance of a single R gene causing broad spectrum and complete resistance to multiple unrelated fungal pathogens.

Example 10. ARG1 Localizes to the Plasma Membrane

The ARG1-GFP fusion protein was transiently expressed into Arabidopsis protoplasts to determine its subcellular localization. Expression of the control plasmid, which only carried the GFP, localized to various subcellular compartments without being specific to any subcellular compartment. ARG1-GFP is localized predominantly to the plasma membrane (FIG. 10*a*). ARG1 encodes a typical NLR protein with N-terminal coiled coil, NB-ARC, and two LRR domains (Table 4). Blast searches confirm that ARG1 shares high identity and structural similarity with RPP13 from Arabidopsis and other plant species. RPP13 is a typical NLR that recognizes the *Hyaloperonospora parasitica* effector protein ATR13, which triggers resistance to biotrophic pathogens[23]. A total of 397 NLR encoding genes were identified from predicted gene models for sorghum (FIG. 22) and most of these NLR genes were located on 3 chromosomes (Chr002, Chr005, and Chr008). By contrast, the CARG deduced amino acid or DNA sequence is unique to the sorghum genome with no similarity to other sequences in the database. Proteomic analysis of SC283 and TAM428 lines identified peptides that map to the ARG1 protein in the resistant lines but there was no polypeptide identified that map to the CARG ORF in any of the genotypes, suggesting that this transcript is not translated and functions as non-coding RNA.

Appendix A ARG1 Sequences
Appendix B CARG sequences
Appendix C Primers used for transgenic and genotyping

SEQUENCE LISTING

<160> NUMBER OF SEQ ID NOS: 41

<210> SEQ ID NO 1
<211> LENGTH: 2970
<212> TYPE: DNA
<213> ORGANISM: Sorghum

<400> SEQUENCE: 1

```
atgggctcag tgttgtttag tctatcatcc aaatgccttg acaagcttgc tgtactgctg      60
gaggaggagg ttatgatgac gctttctgtg cgtaaagata tcaggaagct ccatgactac     120
ctcaagtact tcaattccat tcgtgaggat gctgatgctc gggcaatgga acacagagag     180
acgacaggaa tatggtgggg tgacgtgaaa gatgtcatgt atgatgttga tgacatcata     240
gatcttttga gggctcactc tcagaagcaa cgatgttgtg atttacgcat gctctctagg     300
tttgcacaac ttcaatttga ccacatgatt gccagaaaaa tcaagggtgt aaacgaaagg     360
cttgtagaaa tccaaaagaa cagagatatg ttccttcctc cggggttgta tcctcaggct     420
caggcccctc aaacaaacag agttgatagc aggcatctgg ctgcttcggt tgatgaaatc     480
catgttgttg gagcagaaat caaggaagct actgatagta tggtagaaat gatcgtcggc     540
tatggccatc agagcaggat atcagtttat gggatcgttg ggatgggagg aattggcaag     600
acaactttag ctcagaagat atacaatgat cgtaggataa gagagagatt tcaccaggtc     660
ctcatctggc tgtccatttc acagagcatt gccgagaatg atctactcaa ggaggccatc     720
gaaaaggcag gagggcagtg caatcagcac aagagtaagg atcagctcgt gcaaattctg     780
ctacattcca tcagtgggaa gagtgtcttt cttgtgctgg ataacgttac caaccctgat     840
gtgtggatcg atcttctccg ctctccgatg gagaggtgtt tggatgctca tgtacttgtt     900
accacaagga gcggtcacgt attgtcacag atgaatgcgg ttcatgtcaa ggaaatgcat     960
agactaaagg atgctgatgg cctagaactg cttatgaaga gatctttcag aactgaagat    1020
gaagtaaatg tattcagtga tattggagca aaaattgtta agaaatgtga tggccttccg    1080
cttgccatca aggtcattgg gggcgtccta tcatccaggt cgagcaaaga agaatgggag    1140
agaatactgg agagaagatg gtctattgat gggcttccag aagaactaga aggtgctttg    1200
```

-continued

```
tacttaagct acagtgactt acacccacaa ctgaaacagt gcttcctctg gtgtgccttg      1260
ttgccccaga atttcgatat tcaccgagat gtcacatact ggtggattgc tgaaggtctt      1320
gtgaaggaag agaccagtgg accaatacat aacgtcgccg aagattacta ccatgagctg      1380
atcaagagga atctgctaca ggcaaggcca gagtatgtcg acaagggaat atcgacaatg      1440
catgacctgt taaggcaact tggccaattt ctgacaagga atgaagccgt cttcatgaac      1500
gagaagcgtg atcgttgccc ttctagtatt cgccgattag gtgtcgggag cgctgttgac      1560
gaaataccct ctatagaaga aagaagcgc ctacggtgcc tcattgtctt ggatcacgac       1620
acatgcagat cggtgaagag ggacatcttc agaaagctgg tgcatcttcg catcttagtt      1680
ctacgtggag caggcctcga gagcatacct gcatcggtgg gttacttggc gctgctgagg      1740
ctgctggatc tcagctacaa cgagatcaag gagcttccgg ggtccatcgg aaaccttacc      1800
agccttggtt gcctttcagt gtttggttgc acaaagttgg cagctttgcc acaaagtctg      1860
atgaggctga ccacaataag cttcctccag ataggaaaca caggactggc gcaggttccg      1920
aaaggtattg agaatttcag gcagatagat aaccttagat cagttttcca aaacggtact      1980
gatggtttca gattagatga actgagggca ctctccatga tacgacgcct ctgggttatc      2040
cggctggaga cagcgacacc gccaactgag cccgtattgt gcgacaaggg ttacctgaaa      2100
gagctaggcc tgcgctgtac catgggcaag gaagccaatt gtcgaactca ctacccggac      2160
agtaaggtga agaggattga ggagatctac gagagttttt gcccaccgcc aagcctaagc      2220 tacgtctttta ttgatgggtt ccctggtcgc atgtttccaa cttggctatc tttagaaccg     2280
cagaataaac ttccaaacct ggctcatatg cacttctatg actgcatatc ctgcccgaag      2340
cttcccccag caggccagct accgtttctg caggttcttc acgtcaaagg agctgatgca      2400
gtggtgaaca taggtgctga gctcctcgga aacggcatcc catctggaac acataccact      2460
gcttttccaa agctcgagct gcttgagatc ctcgacatgt acaactggca gaattggtca      2520
ctaagcatgg ataccttgtt cgagaacaca caacagcaat ccttatgcc atgccttaca       2580 cgcctgcggc tgataaattg ccccaagttg agagctctcc ctgatcatct tcacagagtt      2640
gtcaatctac aaaggatcca aatagaagga gctgacagcc tgcaggaggt tgtcaaccat     2700
cccggggttg tgtggctcaa ggttaagaac aacaagtcct tgaggaatat atccaaccct     2760
cctaagctgc gcctcttgct tgcacaagat tgccaagaat tgcagcaggc agagaacctt      2820
agctcactca aggccttgta cgttgtcgat tgcccctatgg agcagatact ctggaagtgt     2880
ttccccatag aacaacagag cacgattgtc cgtgttgtca ccactggggc ccatggtcag      2940
gatatttatc ctcttgaatc agtatttcat                                      2970
```

<210> SEQ ID NO 2
<211> LENGTH: 1988
<212> TYPE: DNA
<213> ORGANISM: Sorghum

<400> SEQUENCE: 2

```
ctttgtggat ctaccggact tcagcccgac gaggcgacac ctcgccgccg ctgtccttgt        60
ccgccacatc tgagcatctc tggtgagttt ctactgagta gagagtttgg agtgttagag       120
acatatgctt gaattggtga ttgtagtttg tgaattgctg ctgaatttgt gagtagaata       180
tatagtacag tactgtgtac tgagttgaaa gagtattatt ccctgcaatg tgtctagcta       240
agaataaaag agagaaatag aatgggtgac cagctattga attatatttt agcgggtgtg       300
```

| | |
|---|---|
| atatttcct ctgttgtgac ttgtgaggat gacatggttt acacttttat ggccatgaag | 360 |
| aagcctaaag aaaaagctct aaacgagtat tgtaatcttc tatttatgta ccttatctta | 420 |
| tatctgaaca attttattg tcatttatgc aagttttgaa tttagagctc tttttagaca | 480 |
| ctttatattt tctttactg aactatttat ataattttg tattgaagta tactgtatta | 540 |
| gataatagat ttttttttg ttagtcatac cgtggactcg aatcctgggt ctgctattgt | 600 |
| ggacagctgc accgctacac tctgctaggg tggtggatct acaccggcgt aggctctgcc | 660 |
| ctgctggcac cccgcacccc acacacatgg cagcctcaaa ggccaaggcg gaggctctga | 720 |
| accaggtata caacagtacg gtacaggtac aacaatctct gaccaaactc tcgacgagcc | 780 |
| ataggcccgt agtcaccaaa agtgccttgc gccactcgag taggtaattg atctgaggaa | 840 |
| ttttgattgt gcagatgcta ttgcctatat ggtattttgt atcacggcat tttacaacaa | 900 |
| gtatgaaata taggctaaat taggctctgc aattagtttc tccctttttt tttttctctt | 960 |
| gcataagtag ctaagctctt taattactcc caaaattaca gtgcagccta taactgtaat | 1020 |
| ctttattacc tttttttca gaatatatga taaaggggct tcaaaaaaga caccacaagc | 1080 |
| acaagaattt caacataaca tgcagacaaa aaatgtatcc aacaaaacat aagttatggt | 1140 |
| ttcaactaaa tccatatgga ggacatgtag ttgccttgag aaaaacattg gttatggatg | 1200 |
| gtaaaaacat taaagtaatt cataagttca tcacaactag atagacatta tagagtattt | 1260 |
| atatgggtat ggcgttagaa aatgaagaaa tagagggtgt acatgtgcaa agatgagtag | 1320 |
| ttttgattaa ttgtaggtac taaacacgaa cttctaatac ttacacttat aagattctgc | 1380 |
| ccgtgcatct cttaaaatta ctggccagtg tgtagccaca tgatgatgaa ctatttgta | 1440 |
| gaaacggacg taggcacaag ttccaaacta aaaaacagac acaagaatac gataataggc | 1500 |
| ctctaagaga ctatgtgctg accagattaa tgaaatatac tgattgaaga tgataggtat | 1560 |
| cctgaccaat ttgcacaaac aggtgttttc acaagttatg aatagaaaaa aaggaacgag | 1620 |
| acacaagaat actgtaacat ttctctaaga catcttgtgc tcactataga ttaatgaaat | 1680 |
| actgattcaa gaggataaat atcctgacca tgggccccag tggtgacaac acggacaatc | 1740 |
| gtgctctgtt gttctatggg gaaacacttc cagagtatct gctccatagg gcaatcgaca | 1800 |
| acgtacaagg ccttgagtga gctaaggttc tctgcctgct gcaattcttg gcaatcttgt | 1860 |
| gtaggcaaga ggcgcagctt aggaaggttg gatatattcc tcaaggactt gttgttctta | 1920 |
| accttgagcc acacaacccc gggatggttg acaacctcct gcaggctgtc agctccttct | 1980 |
| atttggat | 1988 |

<210> SEQ ID NO 3
<211> LENGTH: 22
<212> TYPE: DNA
<213> ORGANISM: artificial
<220> FEATURE:
<223> OTHER INFORMATION: forward primer sequence of InDel4 for PCR marker in Sobic.007G085350

<400> SEQUENCE: 3
ctttgtggat ctaccggact tc        22

<210> SEQ ID NO 4
<211> LENGTH: 26
<212> TYPE: DNA
<213> ORGANISM: artificial
<220> FEATURE:
<223> OTHER INFORMATION: reverse primer sequence of InDel4 for PCR marker in the Sobic.007G085350

```
<400> SEQUENCE: 4
tctctaatac tcccaactct ctactc                                              26

<210> SEQ ID NO 5
<211> LENGTH: 18
<212> TYPE: DNA
<213> ORGANISM: artificial
<220> FEATURE:
<223> OTHER INFORMATION: forward primer sequence of InDel5 for PCR
      marker in Sobic.007G085350

<400> SEQUENCE: 5
ccacagtccc acacacat                                                       18

<210> SEQ ID NO 6
<211> LENGTH: 21
<212> TYPE: DNA
<213> ORGANISM: artificial
<220> FEATURE:
<223> OTHER INFORMATION: reverse primer sequence of InDel5 for PCR
      marker in Sobic.007G085350

<400> SEQUENCE: 6
cctatggctc gttgagagtt t                                                   21

<210> SEQ ID NO 7
<211> LENGTH: 29
<212> TYPE: DNA
<213> ORGANISM: artificial
<220> FEATURE:
<223> OTHER INFORMATION: forward primer for transgenic expression of
      ARG1

<400> SEQUENCE: 7
tccccgcggt atgggctcag tgttgttta                                           29

<210> SEQ ID NO 8
<211> LENGTH: 32
<212> TYPE: DNA
<213> ORGANISM: artificial
<220> FEATURE:
<223> OTHER INFORMATION: reverse primer for transgenic expression of
      ARG1

<400> SEQUENCE: 8
ggactagtat gaaatactga ttcaagagga ta                                       32

<210> SEQ ID NO 9
<211> LENGTH: 20
<212> TYPE: DNA
<213> ORGANISM: artificial
<220> FEATURE:
<223> OTHER INFORMATION: forward primer sequence of InDel6 for PCR
      marker in Sorghum

<400> SEQUENCE: 9
ccacacagac gaaagtccct                                                     20

<210> SEQ ID NO 10
<211> LENGTH: 20
<212> TYPE: DNA
<213> ORGANISM: artificial
<220> FEATURE:
<223> OTHER INFORMATION: Reverse primer sequence of InDel6 for PCR
      marker in sorghum
```

<400> SEQUENCE: 10
taaagcgacc tgctactttc                                            20

<210> SEQ ID NO 11
<211> LENGTH: 19
<212> TYPE: DNA
<213> ORGANISM: artificial
<220> FEATURE:
<223> OTHER INFORMATION: qRT-PCR forward primer for CARGa

<400> SEQUENCE: 11
acacatggca gcctcaaag                                             19

<210> SEQ ID NO 12
<211> LENGTH: 22
<212> TYPE: DNA
<213> ORGANISM: artificial
<220> FEATURE:
<223> OTHER INFORMATION: qRT-PCR reverse primer for CARGa

<400> SEQUENCE: 12
tgctgttcaa gagtcactat cc                                         22

<210> SEQ ID NO 13
<211> LENGTH: 20
<212> TYPE: DNA
<213> ORGANISM: artificial
<220> FEATURE:
<223> OTHER INFORMATION: qRT-PCR forward primer for CARGb

<400> SEQUENCE: 13
ccctgacagc aaactttgtg                                            20

<210> SEQ ID NO 14
<211> LENGTH: 21
<212> TYPE: DNA
<213> ORGANISM: artificial
<220> FEATURE:
<223> OTHER INFORMATION: qPCR reverse primer for CARGb

<400> SEQUENCE: 14
caatagcaga cccaggattc g                                          21

<210> SEQ ID NO 15
<211> LENGTH: 22
<212> TYPE: DNA
<213> ORGANISM: artificial
<220> FEATURE:
<223> OTHER INFORMATION: qRT PCR forward primer for ARG1

<400> SEQUENCE: 15
tgttcttaac cttgagccac ac                                         22

<210> SEQ ID NO 16
<211> LENGTH: 23
<212> TYPE: DNA
<213> ORGANISM: artificial
<220> FEATURE:
<223> OTHER INFORMATION: qRT PCR reverse primer for ARG1

<400> SEQUENCE: 16
atccaaatag aaggagctga cag                                        23

<210> SEQ ID NO 17
<211> LENGTH: 22

-continued

```
<212> TYPE: DNA
<213> ORGANISM: artificial
<220> FEATURE:
<223> OTHER INFORMATION: qRT PCR forward primer for Actin

<400> SEQUENCE: 17
cctccagaaa ggaagtacag tg                                              22

<210> SEQ ID NO 18
<211> LENGTH: 20
<212> TYPE: DNA
<213> ORGANISM: artificial
<220> FEATURE:
<223> OTHER INFORMATION: qRT PCR reverse primer for Actin

<400> SEQUENCE: 18
gggcgcaaag aattagaagc                                                 20

<210> SEQ ID NO 19
<211> LENGTH: 22
<212> TYPE: DNA
<213> ORGANISM: artificial
<220> FEATURE:
<223> OTHER INFORMATION: Forward Primer for Actin in Semi-quantitative
      RT-PCR

<400> SEQUENCE: 19
cctccagaaa ggaagtacag tg                                              22

<210> SEQ ID NO 20
<211> LENGTH: 20
<212> TYPE: DNA
<213> ORGANISM: artificial
<220> FEATURE:
<223> OTHER INFORMATION: Reverse Primer for Actin in Semi-quantitative
      RT-PCR

<400> SEQUENCE: 20
gggcgcaaag aattagaagc                                                 20

<210> SEQ ID NO 21
<211> LENGTH: 2970
<212> TYPE: DNA
<213> ORGANISM: Sorghum bicolor

<400> SEQUENCE: 21
atgggctcag tgttgtttag tctatcatcc aaatgccttg acaagcttgc tgtactgctg     60
gaggaggaga ttatgatgac gctatctgtg cgtaaagaga tcaggaagct ccatgactac    120
ctcaagtact ttgattccat tcatgaggat gctgatgctc gggcaatgga acacagagag    180
atgacaggaa tatggtgggg tgacgtgaaa gatgtcatgt atgatgttga tgacatcata    240
gatcttttga gggctcactc tcagaagcaa cgatgttgtg atttacgcat gctctctagg    300
tttgcacaac ttcaatttga ccacatgatt gccagaaaaa tcaagggtgt aaacgaaagg    360
cttgtagaaa tccaaaagaa cagagatatg ttccttcctc cggggttgta tcctcaggct    420
caggcccctc aaacaaacgg agttgatagc aggcatctgg ctgcttcggt tgatgaaatc    480
catgttgttg gagcagaaat caaggaagct actgatagta tggtagaaat gattgtcggt    540
tatggccatc agagcaggat atcagtttat gggatcgttg ggatgggagg aattggtaag    600
acaactttag ctcagaagat atacaatgat cgtaggataa gagagagatt tcaccaggtc    660
ctcatctggc tgtccatttc acagagcatt gccgagaatg atctactcaa ggaggccatc    720
```

```
gaaaaggcag gagggcagtg caatcagcac aagagcaagg atcagctcgt gcaaattctg    780
ctacattcca tcagtgggaa gagtgtcttt cttgtgctgg ataacgttac caaccctgat    840
gtgtggatcg atcttctccg ctctccgatg gagaggtgtt tggatgctca tgtacttgtt    900
accacaagga gcggtcacgt attgtcacag atgaatgcgg tgcatgtcaa ggaaatgcac    960
agactaaagg atgctgatgg cctagaactg cttatgaaga gatctttcag aaccaaagac   1020
gaagtaaatg tattcagtga tattggagca aaaattgtta agaaatgtga tggccttcct   1080
cttgccatca aggtcattgg aggcgtccta tcatccaggt cgagcaaaga agaatgggag   1140
agaatactgg agagaagatg gtctattgat gggcttccag aagaactaga aggtgctttg   1200
tacttaagct acagtgactt acacccacaa ctcaaacagt gcttcctctg ctgtgccctg   1260
ttgcctcaga atttcgatat tcaccgagat gtcacatact ggtggattgc tgaaggtttt   1320
gtgaaggaag agggcagcgg accgatacat aacattgccg aagattacta ccatgagctg   1380
atcaagagga atctgctaca ggcaaggcca gagtatgtcg acaagggagt atcgacaatg   1440
catgacctgt tgaggcaact tggccaattt ctgaaaagaa atgaagccat cttcatgaac   1500
gagaagcgtg aacgttgcct ttgaagtatt cgccgactag tgtcgggag cgctgttgac   1560 gaaatacctt ctatagaaga gaagaagcgc tacggtgcc tcattgtctt gcatcacgac   1620
acatgcagat cggtgaagag ggacatcttc agaaagttgg tgcatcttcg catcttagtt   1680
ctacgtggag caggccttga gagcatacct gcatcggtgg gttacttggc gctgctgagg   1740
ctgctggatc tcagctacaa tgagatcaag gagcttccag ggtccatcgg aaaccttacc   1800
agccttggtt gcctttcagt gtttggttgc acaaagttgg cagctttgcc aacaagtctg   1860
atgaggctga ccacaataag cttcctcaaa ataggaaaca caggactggc gcaggttccg   1920
aaaggtattg agaatttcaa gcagatggat aaccttagat cagttttcca aaacggtact   1980
gatggtttca gattagatga actgagggca ctctctatga tacgacgcct ctgggttatc   2040
cggctggaga cagcgatacc gccaactgag cccatactgt gcgacaaggg ttacctgaaa   2100
gagctaggcc tgcgctgcac catgggtaag gaagccaatt gtcgaactca ctatccggac   2160
agcaaggtga agaggattga ggagatctac gagagttttt gcccaccgcc aagcctaagc   2220
tacgtcttca ttgatgggtt ccctggttgc atgtttccaa cttggctatc ttcagaaccg   2280
cagaataaac tgccaaacct ggctcatatg cacttcaacg actgcatatc ctgcccgaag   2340
cttcccccag caggccagct accgtttctg caggttcttc acgtcaaagg agctgacgca   2400
gtagtgaaca taggtgctga gctcctcgga aacagcatcc catccggaac acataccact   2460
gcttttccaa agctcgagct gcttgagatc ctcgacatgt acaactggca gaattggtca   2520
ctaagcatgg ataccttgtt cgagaaaaca caacagcaat cccttatgcc atgccttaca   2580
cggctgcggc tgataaattg ccccaagttg agagctctcc ctgatcatct tcacagagtt   2640
gtcaatctac aaaggatcca aatagaagga gctgacagcc tgcaggagat tgtcaaccat   2700 cccgggggttg tgtggctcaa ggttaagaac aacaagtcct tgaggaatat atccaacctt   2760
cctaagctgc gcctcttgct tgcacaagat tgccaagaat tgcagcaggc agagaacctt   2820
agctcactca aggccttgta cgttgtcgat tgccctatgg agcagatact ctggaagtgt   2880
ttccccatag aacaacagag cacgattgtc cgtgttgtca ccactggggc ccatggtcag   2940
gatatttatc ctcttgaatc agtatttcat                                     2970
```

<210> SEQ ID NO 22
<211> LENGTH: 1983

<212> TYPE: DNA
<213> ORGANISM: Artificial Sequence
<220> FEATURE:
<223> OTHER INFORMATION: CARG_TAM428

<400> SEQUENCE: 22

```
ctttgtggat ctaccggact tcagcccgac gaggcgacct ggcgacaccc cgccgccgct      60
gtccttgtcc gccacatctg agcatctctg gtgagtttct actgagtaga gagttgggag     120
tattagagac atatgctgaa attggtgatt gtaatttgtg aattgctgct gaatttgtga     180
gtagaatata tagtacagta ctgtactgag ttgaaagagt attccctgca atgtgtctag     240
ctaagaataa aagagagaaa tagaatgggt gaccagctat tgaattatat tttagcgggt     300
gtgatatttt tctctgttgt gaggatgaca tggtttacac ttttatggcc atgaagaagc     360
ctaataaaga aaaagctcta aacgagtatt gtaatcttct atttatgtac cttatcttat     420
gtttgaacaa tttttattgt catttatgca agtttgaat ttagagctct ttttagacac      480
tttatgtttt cttttactga actatttaaa taatttttgt attgaagtat actgtattag     540
ataatagatt tttttttgt tagtcatacc gtggactcga gtcctgggtc tgctattgtg      600
gacagccgca ccactatact ctgctacggt ggtggatcta caccggcgta ggctctgcac     660
tgctggcacc ccgcaccca cagtcccacc cacatggcag cctcaaaggc caaggcggag      720
gctctgaacc agtacggtgc aggtacaaca atctctgacc aaactctcaa cgagccatag     780
gcccatagtc accaaaactt ccttgtgcca ctcgaataga taatcgatcc gaggaatttt     840
gattgtgcac atgctattgc ctactacagt attttttgtat caggcatttt acaacaagta     900
tgaaatatag gctaaattag gctctgcaat tagtttctcc ctttttttc tcttgcataa      960
gtagctaagg ctctttaatt actccctgcg ctccaaaata caagacattt ttatcgttat    1020
tatcttttt tcagaatata tgacaaaggg gcttcaaaaa agataccaca aagcacaaga    1080
atttcaacat aacatgcaga taaaaaatgt atccaacaaa acataaagta atggtttcaa    1140
ctaaatccat atggaggaca tgtaggtgcc ttgagaaaaa caatggttat ggatggtaaa    1200
aacattaaag taattcataa gttcatcaca actggataga cattatagag tatttatatg    1260
ggtatggcgt tagaaaatga agaaatagag ggagtacatg tgcaaagatg agtagttttg    1320
attaattgta ggtactaaac acgaacttct aatacttaca cttataagat cctgcccgtg    1380
catctcttaa aattactggc cagtgtgtag ccacatgatg atgaactatt ttgtagaaac    1440
ggacgtgagc acaagttcca aactaaaaaa cagacacaag aatacggtaa gaggcctcta    1500
agagactatg tgctgaccag attaatgaaa tatactgatt gaagatgata ggtatcctga    1560
ccaatttgca cagacaggtg ttttcacaag ttatgaatag aaaaaaagga aagagacaca    1620
agaatactgt aatatttctc taagacatct tgtgctcact atagattaat gaaatactga    1680
ttcaagagga taaatatcct gaccatgggc cccagtggtg acaacacgga caatcgtgct    1740
ctgttgttct atggggaaac acttccagag tatctgctcc ataggggcaat cgacaacgta    1800
caaggccttg agtgagctaa ggttctctgc ctgctgcaat tcttggcaat cttgtgcaag    1860
caagaggcgc agcttaggaa ggttggatat attcctcaag gacttgttgt tcttaaccctt   1920
gagccacaca accccgggat ggttgacaat ctcctgcagg ctgtcagctc cttctatttg    1980
gat                                                                  1983
```

<210> SEQ ID NO 23
<211> LENGTH: 277
<212> TYPE: DNA

<213> ORGANISM: Sorghum

<400> SEQUENCE: 23

| tagggatgaa aacagtacgg gatattttcc gaccgtattc gagaccgaat tcgtttagag | 60 |
| gggtttaaat ctgtccgtat ccgagtccga atattcaaca tccgataccg tatccgtatc | 120 |
| cgaatactta aatcgtatat ttgtgatgtc gacctccaat catatcttat ccgacatagt | 180 |
| tgacattatc cgtattcgaa tccgaattcg accaaaaata tgaaaacaaa tatgatatca | 240 |
| gtgatattcg tccgtatccg atgcgttttc atccta | 277 |

<210> SEQ ID NO 24
<211> LENGTH: 248
<212> TYPE: DNA
<213> ORGANISM: Sorghum

<400> SEQUENCE: 24

| taaggccttg tttagttcac cttgaaaacc aaaaagtttt caagattccc tgtcacatcg | 60 |
| aattttgtgg cacatgcatg aaatattaaa tatagacgaa acaaaaact aattacacag | 120 |
| tttagctgta aatcacgaga cgaatctttt gatcctagtt agtccatgat tggataatat | 180 |
| ttgtcacaaa caaacgaaag tgctacagta tcgaaaactt ttcactttc ggaadtaaac | 240 |
| aagcctta | 248 |

<210> SEQ ID NO 25
<211> LENGTH: 24
<212> TYPE: RNA
<213> ORGANISM: Sorghum

<400> SEQUENCE: 25

| gagacgaauc uuuugauccu aguu | 24 |

<210> SEQ ID NO 26
<211> LENGTH: 24
<212> TYPE: RNA
<213> ORGANISM: Artificial Sequence
<220> FEATURE:
<223> OTHER INFORMATION: artificial small RNA sequence of a MITE

<400> SEQUENCE: 26

| gagaugaauc uuuugagucu aguu | 24 |

<210> SEQ ID NO 27
<211> LENGTH: 2524
<212> TYPE: DNA
<213> ORGANISM: Artificial Sequence
<220> FEATURE:
<223> OTHER INFORMATION: spliced nucleic acid sequence of Sorghum
    bicolor

<400> SEQUENCE: 27

| atgggctcag tgttgtttag tctatcatcc aaatgccttg acaagcttgc tgtactgctg | 60 |
| gaggaggaga ttatgatgac gctatctgtg cgtaaagaga tcaggaagct ccatgactac | 120 |
| ctcaagtact ttgattccat tcatgaggat gctgatgctc gggcaatgga acacagagag | 180 |
| atgacaggaa tatggtgggg tgacgtgaaa gatgtcatgt atgatgttga tgacatcata | 240 |
| gatcttttga gggctcactc tcagaagcaa cgatgttgtg atttacgcat gctctctagg | 300 |
| tttgcacaac ttcaatttga ccacatgatt gccagaaaaa tcaagggtgt aaacgaaagg | 360 |
| cttgtagaaa tccaaaagaa cagagatatg ttccttcctc cggggttgta tcctcaggct | 420 |

```
caggcccctc aaacaaacgg agttgatagc aggcatctgg ctgcttcggt tgatgaaatc      480
catgttgttg gagcagaaat caaggaagct actgatagta tggtagaaat gattgtcggt      540
tatggccatc agagcaggat atcagtttat gggatcgttg ggatgggagg aattggtaag      600
acaactttag ctcagaagat atacaatgat cgtaggataa agagagagatt tcaccaggtc     660 ctcatctggc tgtccatttc acagagcatt gccgagaatg atctactcaa ggaggccatc      720
gaaaaggcag gagggcagtg caatcagcac aagagcaagg atcagctcgt gcaaattctg      780
ctacattcca tcagtgggaa gagtgtcttt cttgtgctgg ataacgttac caaccctgat      840
gtgtggatcg atcttctccg ctctccgatg gagaggtgtt tggatgctca tgtacttgtt      900
accacaagga gcggtcacgt attgtcacag atgaatgcgg tgcatgtcaa ggaaatgcac      960
agactaaagg atgctgatgg cctagaactg cttatgaaga gatctttcag aaccaaagac     1020
gaagtaaatg tattcagtga tattggagca aaaattgtta agaaatgtga tggccttcct     1080
cttgccatca aggtcattgg aggcgtccta tcatccaggt cgagcaaaga gaatgggag      1140 agaatactgg agagaagatg gtctattgat gggcttccag aagaactaga aggtgctttg     1200
tacttaagct acagtgactt acacccacaa ctcaaacagt gcttcctctg ctgtgccctg     1260
ttgcctcaga atttcgatat tcaccgagat gtcacatact ggtggattgc tgaaggtttt     1320
gtgaaggaag agggcagcgg accgatacat aacattgccg aagattacta ccatgagctg     1380
atcaaggaga atctgctaca ggcaaggcca gagtatgtcg acaagggagt atcgacaatg     1440
catgacctgt tgaggcaact tggccaattt ctgaaaagaa atgaagccat cttcacagat     1500
ggataacctt agatcagttt tccaaaacgg tactgatggt ttcagattag atgaactgag     1560
ggcactctct atgatacgac gcctctgggt tatccggctg gagacagcga taccgccaac     1620
tgagcccata ctgtgcgaca agggttacct gaaagagcta ggcctgcgct gcaccatggg     1680
taaggaagcc aattgtcgaa ctcactatcc ggacagcaag gtgaagagga ttgaggagat     1740
ctacgagagt ttttgcccac cgccaagcct aagctacgtc ttcattgatg ggttccctgg     1800
ttgcatgttt ccaacttggc tatcttcaga accgcagaat aaactgccaa acctggctca     1860
tatgcacttc aacgactgca tatcctgccc gaagcttccc ccagcaggcc agctaccgtt     1920
tctgcaggtt cttcacgtca aaggagctga cgcagtagtg aacataggtg ctgagctcct     1980
cggaaacagc atcccatccg gaacacatac cactgctttt ccaaagctcg agctgcttga     2040
gatcctcgac atgtacaact ggcagaattg gtcactaagc atggatacct tgttcgagaa     2100
aacacaacag caatccctta tgccatgcct tacacggctg cggctgataa attgccccaa     2160
gttgagagct ctccctgatc atcttcacag agttgtcaat ctacaaagga tccaaataga     2220
aggagctgac agcctgcagg agattgtcaa ccatcccggg gttgtgtggc tcaaggttaa     2280
gaacaacaag tccttgagga atatatccaa ccttcctaag ctgcgcctct tgcttgcaca     2340
agattgccaa gaattgcagc aggcagagaa ccttagctca ctcaaggcct tgtacgttgt     2400
cgattgccct atggagcaga actctctggaa gtgtttcccc atagaacaac agagcacgat     2460
tgtccgtgtt gtcaccactg gggcccatgg tcaggatatt tatcctcttg aatcagtatt     2520
tcat                                                                  2524
```

<210> SEQ ID NO 28
<211> LENGTH: 2976
<212> TYPE: DNA
<213> ORGANISM: Sorghum variants P1585749 and P1586439

<400> SEQUENCE: 28

```
atgggctcgg tgttgtttag tctatcatcc aaatgcctta acaagcttgc tgtactgctg      60
gaggaggagg ttatgatgac gctttctgtg cgtaaagata tcaggaagct ccatgaaaac     120
ctcaagtact tcaattccat tcgtgacgat gctgatgctt gggcaatgga acacagagag     180
acgacaggaa tatggtgggg tgacgtgaaa gatgtcatgt atgatgttga tgacatcata     240
gatcttttga gggctcactc tcagaagcaa cgatgttgtg atttacacat gctctctagg     300
tttgcacaac ttcaatttga ccacatgatt gccagaaaaa tcaagggtgt aaacgaaagg     360
cttgtagaaa tccaaaagaa cagagatatg ttccttcctc cggggttgta tcctcaggca     420
caggcccctc aaacaaacag agttgatagc aggcatctag ctgcttcggt tgatgaaatc     480
catgttgttg gagcagaaat caaggaagct actgatagta tggtagaaat gatcgtcggc     540
tatggccatc agagtaggat atcagtttat gggatccttg ggatgggagg aattggcaag     600
acaactttag ctcaaaagat atacaatgat cgtaggataa agagagagatt tcaccaggcc     660 ctcatctggc tgtccattcc acatagcatt gccgagaatg atctactcaa ggaggccatc     720
gaaaaggcag gagggcagtg caatcagcac aagagtaagg atcagctcgt gcaaattctg     780
ctacattccg tcagtgggaa gagtgtcttt cttgtgctgg ataacgttac caaccctgat     840
gtgtggatcg atcttctccg ctctccgatg gagaggtgtt tggatgctca tgtacttgtt     900
accacaagga tcgatggcgt attgtcacag atgaatgcgg ttcatgtcaa ggaaatgcat     960
agactaaagg atgctgatgg cctagaactg cttatgaaga gatcttttcag aactgaagat    1020 gaagtaaatg tattcagtga tattggagca aaaattgtta agaaatgcga gggccttccg    1080
cttgccatca aggtcattgg gggtgtccta tcatccaggt cgagcaaaga agaatgggag    1140
agaatactgg agagaagatg gtctattgat gggcttccaa agaactagaa ggtgctttg     1200 tacttaagct actgtgactt acacccacaa ctgaaacagt gcttcctctg gtgtgccttg    1260
ttgccccaga atttcgatat tcaccgagat gtcacatact ggtggatttc tgaaggtctt    1320
gtgaaggaag agaccagtgg accaatacat aacgtcgccg aagattacta ccatgagctg    1380
atcaagagga atctgctaca ggcaaggcca gagtatgtcg acaagggaat atcaacaatg    1440
catgacctgt taaggcaact tggccagttt ctgacaagga atgaagccgt cttcatgaac    1500
gagaagcgtg atcgttgccc ttctagtatt cgccgattag gtgtcgggag cgctgttgac    1560
gaaatacctt ctatagaaga gaagaagcgc tacggtgcc tcattgtctt ggatcacgac    1620
acatgcagat tggtgaagag ggacatcttc agaaagctgg tgcatcttcg catcttagtt    1680
ctacgtggag caggcctcga gagcatacct gcatcggtgg gttacttggc gctgctgtgg    1740
ctgctggatc tcagctacaa cgagatcaag gagcttccgg ggtccatcgg aaaccttacc    1800
agccttggtt gcctttcagt gtttggttgc acaaagttgg cagctttgcc gcagagtctg    1860
atgaggctga ccacaataag cttcctccag ataggaaaca caggactcgc acaggttccg    1920
aaaggtattg agaattttag gcagatagat aaccttagat cagttttcca aaacagtact    1980
gatggtttca gattagatga actgagggca ctctccatga tacgacgcct ctggtttatc    2040
tggctggaga cagcgacacc gccaactgag tccgtattgt gtgacaaggg ttacctgaaa    2100
gagctaggcc tgcgctgtac catgggcaag gaagccaatt gtcgaactca ctacccggac    2160
agtaaggtga agaggattga ggagatctac gagagttttt gcccaccgcc aagcctaagc    2220
tacgtcttta ttgatgggtt ccctggtcgc gtgtttccaa cttggctatc tttagaaccg    2280
cagaataaac ttccaaaccct ggctcatatg cacttctatg actgcatatc ctgcccgaag    2340
```

```
cttcccccag caggccagct actaccgttt ctgcaggttc ttcacgtcaa aggagctgat    2400
gcagtggtga acataggtgc tgagctcctc ggaaacggca tcccatctgg aacacatacc    2460
actgcttttc caaagctcga gctgcttgag atcctcgaca tgtacaactg cagaattgg     2520 tcactaagca tggatacttt gttcgacaac acacaacagc aattgtttat gccatgcctt    2580
acacgcctgc ggctgataaa ttgccccaag ttgagagctc tccctgatca tcttcataga    2640
gttgtcaatc tacagaggat ccacatgaa ggagctgaca gcctgcagga ggttgtcgat     2700
catcccgggg ttgtgtggct caaggttaag aacaacaagt ccttgaggaa tatatccaac    2760
cttcctaagc tgtgcctctt gcttgcacaa gattgccacg aattgcagca ggcagagaac    2820
cttagctcac tcaaggcctt gtacgttgtc gattgcccta tggagcagat actctggaag    2880
tgtttcccca tagaacaaca gagcacaatt gtccgtgttg tcaccactgg gacccatggt    2940
caggatattt atcctcttga atcagtgttt cattaa                              2976

<210> SEQ ID NO 29
<211> LENGTH: 2976
<212> TYPE: DNA
<213> ORGANISM: Sorghum variant KS115

<400> SEQUENCE: 29
atgggctcag tgttgtttag tctatcatcc aaatgccttg caagcttgc tgtactgctg      60 gaggaggaga ttatgatgac gctatctgtg cgtaaagaga tcaggaagct ccatgactac    120
ctcaagtact ttaattccat tcatgacgat gctgatgctc gggcaatgga acacagagag    180
atgacaggaa tatggtgggg tgacgtgaaa gatgtcatgt atgatgttga tgacatcata    240
gatcttttga gggctcactc tcagaagcaa cgatgttgtg atttacgcat gctctctagg    300
tttgcacaac ttcaatttga ccacatgatt gccagaaaaa tcaagggtgt aaacgaaagg    360
cttgtagaaa tccaaaagaa cagagatatg ttccttcctc cggggttgta tcctcaggct    420
caggcccctc aaacaaacgg agttgatagc aggcatctgg ctgcttcggt tgatgaaatc    480
catgttgttg gagcagaaat caaggaagct actgatagta tggtagaaat gatcgtcggc    540
tatggccatc agagcaggat atcagtttat gggatcgttg ggatgggagg aattggtaag    600
acaactttag ctcagaagat atacaatgat cgtaggataa gagagagatt tcaccaggtc    660
ctcatctggc tgtccatttc acagagcatt gccgagaatg atctactcaa ggaggccatc    720
gaaaaggcag gagggcagtg caatcagcac aagagcaagg atcagctcgt gcaaattctg    780
ctacattcca tcagtgggaa gagtgtcttt cttgtgctgg ataacgttac caaccctgat    840
gtgtggatcg atcttctccg ctctccgatg gagaggtgtt tggatgctca tgtacttgtt    900
accacaagga gcggtcacgt attgtcacag atgaatgcgg tgcatgtcaa ggaaatgcac    960
agactaaagg atgctgatgg cctagaactg cttatgaaga gatcttttcag aaccaaagat   1020 gaagtaaatg tattcagtga tattggagca aaaattgtta agaaatgtga tggccttcct   1080
cttgccatca aggtcattgg aggcgtccta tcatccaggt cgagcaaaga gaatgggag    1140 agaatactgg agagaagatg gtctattgat gggcttccag aagaactaga aggtgctttg   1200
tacttaagct acagtgactt acacccacaa ctcaaacagt gcttcctctg gtgtgccttg   1260
ttgcctcaga atttcgatat tcaccgagat gtcacatact ggtggattgc tgaaggtttt   1320
gtgaaggaag agggcagcgg accgatacat aacattgccg aagattacta ccatgagctg   1380
atcaaggaga atctgctaca ggcaaggcca gagtatgtcg acaagggaat atcgacaatg   1440
catgacctgt taaggcaact tggccaattt ctgacaagga atgaagccgt cttcatgaac   1500
```

```
gagaagcgtg atcgttgccc ttctagtatt cgccgattag gtgtcgggag cgctgttgac    1560
gaaataccct ctatagaaga gaagaagcgc ctacggtgcc tcattgtctt ggatcacgac    1620
acatgcagat cggtgaagag ggacatcttc agaaagctgg tgcatcttcg catcttagtt    1680
ctacgtggag caggcctcga gagcatacct gcatcggtgg gttacttggc gctgctgagg    1740
ctgctggatc tcagctacaa cgagatcaag gagcttccgg ggtccatcgg aaaccttacc    1800
agccttggtt gcctttcagt gtttggttgc acaaagttgg cagctttgcc acaaagtctg    1860
atgaggctga ccacaataag cttcctccag ataggaaaca caggactggc gcaggttccg    1920
aaaggtattg agaatttcag gcagatagat aaccttagat cagttttcca aaacggtact    1980
gatggtttca gattagatga actgagggca ctctccatga tacgacgcct ctgggttatc    2040
cggctggaga cagcgacacc gccaactgag cccgtattgt gcgacaaggg ttacctgaaa    2100
gagctaggcc tgcgctgtac catgggcaag gaagccaatt gtcgaactca ctacccggac    2160
agtaaggtga gaggattga ggaggtctac gagagttttt gcccaccgcc aagcctaagc    2220
tacgtcttta ttgatgggtt ccctggtcgc atgtttccaa cttggctatc tttagaaccg    2280
cagaataaac ttccaaacct ggctcatatg cacttctatg actgcatatc ctgcccgaag    2340
cttcccccag caggccagct actaccgttt ctgcaggttc ttcacgtcaa aggagctgat    2400
gcagtggtga acataggtgc tgagctcctc ggaaacggca tcccatctgg aacacatacc    2460
actgcttttc caaagctcga gctgcttgag atcctcgaca tgtacaactg gcagaattgg    2520
tcactaagca tggatacctt gttcgagaac acacaacagc agttcctttat gccatgcctt    2580 acacgcctgc ggctgataaa ttgccccaag ttgagagctc tccctgatca tcttcacaga    2640
gttgtcaatc tacaaaggat ccaaatgaaa ggagctgaca gcctgcagga ggttgtcaac    2700
catcccgggg ttgtgtggct caaggctaag aacaacaagt ccttgaggaa tatatccaac    2760
cttcctaagc tgcgcctctt gcttgcacaa gattgccaag aattgcagca ggcagagaac    2820
cttagctcac tcaaggcctt gtacgttgtc gattgcccta tggagcagat actctggaag    2880
tgtttcccca tagaacaaca gagcacgatt gtccgtgttg tcaccactgg ggcccatggt    2940
caggatattt atcctcttga atcagtattt cattaa                              2976
```

<210> SEQ ID NO 30
<211> LENGTH: 2976
<212> TYPE: DNA
<213> ORGANISM: Sorghum greenleaf variant

<400> SEQUENCE: 30

```
atgggctcgg tgttgtttag tctatcatcc aaatgccttg acaagcttgc tgtactgctg     60
gaggaggagg ttatgatgac gctttctgtg cgtaaagata tcaggaagct ccatgactac    120
ctcaagtact tcaattccat tcgtgacgat gctgatgctc gggcaatgga acacagagag    180
acgacaggaa tatggtgggg tgacgtgaaa gatgtcatgt atgatgttga tgacatcata    240
gatcttttga gggctcactc tcagaagcaa cgatgttgtg atttacgcat gctctctagg    300
tttgcacaac ttcaatttga ccacatgatt gccagaaaaa tcaagggtgt aaacgaaagg    360
cttgtagaaa tccaaaagaa cagagatatg ttccttcctc cggggttgta tcctcaggct    420
caggcccctc aaacaaacag agttgatagc aggcatctgg ctgcttcggt tgatgaaatc    480
catgttgttg agcagaaaat caaggaagct actgatagta tggtagaaat gatcgtcggc    540
tatggccatc agagcaggat atcagtttat gggatcgttg ggatgggagg aattggcaag    600
```

-continued

```
acaactttag ctcagaagat atacaatgat cgtaggataa gagagagatt tcaccaggtc    660
ctcatctggc tgtccatttc acagagcatt gccgagaatg atctactcaa ggaggccatc    720
gaaaaggcag gagggcagtg caatcagcac aagagtaagg atcagctcgt gcaaattctg    780
ctacattcca tcagtgggaa gagtgtcttt cttgtgctgg ataacgttac caaccctgat    840
gtgtggatcg atcttctccg ctctccgatg gagaggtgtt tggatgctca tgtacttgtt    900
accacaagga gcggtcacgt attgtcacag atgaatgcgg ttcatgtcaa ggaaatgcat    960
agactaaagg atgctgatgg cctagaactg cttatgaaga gatcttttcag aactgaagat   1020 gaagtaaatg tattcagtga tattggagca aaaattgtta agaaatgtga tggccttccg   1080
cttgccatca aggtcattgg gggcgtccta tcatccaggt cgagcaaaga agaatgggag   1140
agaatactgg agagaagatg gtctattgat gggcttccag aagaactaga aggtgctttg   1200
tacttaagct acagtgactt acacccacaa ctgaaacagt gcttcctctg tgtgccttg    1260 ttgccccaga atttcgatat tcaccgagat gtcacatact ggtggattgc tgaaggtctt   1320
gtgaaggaag agaccagtgg accaatacat aacgtcgccg aagattacta ccatgagctg   1380
atcaagagga atctgctaca ggcaaggcca gagtatgtcg acaagggaat atcgacaatg   1440
catgacctgt taaggcaact tggccaattt ctgacaagga atgaagccgt cttcatgaac   1500
gagaagcgtg atcgttgccc ttctagtatt cgccgattag gtgtcgggag cgctgttgac   1560 gaaataccett ctatagaaga gaagaagcgc ctacggtgcc tcattgtctt ggatcacgac   1620
acatgcagat cggtgaagag ggacatcttc agaaagctgg tgcatcttcg catcttagtt   1680
ctacgtggag caggcctcga gagcatacct gcatcggtgg ttacttggc gctgctgagg    1740 ctgctggatc tcagctacaa cgagatcaag gagcttccgg ggtccatcgg aaaccttacc   1800
agccttggtt gcctttcagt gtttggttgc acaaagttgg cagctttgcc acaaagtctg   1860
atgaggctga ccacaataag cttcctccag ataggaaaca caggactggc gcaggttccg   1920
aaaggtattg agaatttcag gcagatagat aaccttagat cagtttttcca aaacggtact   1980 gatggtttca gattagatga actgagggca ctctccatga tacgacgcct ctgggttatc   2040
cggctggaga cagcgacacc gccaactgag cccgtattgt gcgacaaggg ttacctgaaa   2100
gagctaggcc tgcgctgtac catgggcaag gaagccaatt gtcgaactca ctaccccggac   2160 agtaaggtga agaggattga ggagatctac gagagttctt gcccaccgcc aagcctaagc   2220 tacgtctttta ttgatgggtt ccctggtcgc gtgtttccaa cttggctatc tttagaaccg   2280
cagaataaac ttccaaacct ggctcatatg cacttctatg actgcatatc ctgcccgaag   2340
cttcccccag caggccagct actaccgttt ctgcaggttc ttcacgtcaa aggagctgat   2400
gcagtggtga acataggtgc tgagctcctc ggaaacggca tcccatctgg aacacatacc   2460
actgcttttc caaagctcga gctgcttgag atcctcgaca tgtacaactg gcagaattgg   2520
tcactaagca tggatacctt gttcgagaac acacaacagc aattccttat gccatgcctt   2580
acacgcctgc ggctgataaa ttgccccaag ttgagagctc tccctgatca tcttcacaga   2640
gttgtcaatc tacaaaggat ccaaatagaa ggagctgaca gcctgcagga ggttgtcaac   2700
catcccgggg ttgtgtggct caaggttaag aacaacaagt ccttgaggaa tatatccaac   2760
cttcctaagc tgcgcctctt gcttgcacaa gattgccaag aattgcagca ggcagagaac   2820
cttagctcac tcaaggcctt gtacgttgtc gattgcccta tggagcagat actctggaag   2880 tgtttccccca tagaacagca gagcacgatt gtccgtgttg tcaccactgg ggcccatggt   2940
caggatattt atcctcttga atcagtattt cattaa                              2976
```

<210> SEQ ID NO 31
<211> LENGTH: 2976
<212> TYPE: DNA
<213> ORGANISM: Sorghum BTX378 and SC35C variants

<400> SEQUENCE: 31

| | | | | | | |
|---|---|---|---|---|---|---|
| atgggctcgg | tgttgtttag | tctatcatcc | aaatgccttg | acaagcttgc | tgtactgctg | 60 |
| gaggaggagg | ttatgatgac | gctttctgtg | cgtaaagata | tcaggaagct | ccatgactac | 120 |
| ctcaagtact | tcaattccat | tcgtgacgat | gctgatgctc | gggcaatgga | acacagagag | 180 |
| acgacaggaa | tatggtgggg | tgacgtgaaa | gatgtcatgt | atgatgttga | tgacatcata | 240 |
| gatcttttga | gggctcactc | tcagaagcaa | cgatgttgtg | atttacgcat | gctctctagg | 300 |
| tttgcacaac | ttcaatttga | ccacatgatt | gccagaaaaa | tcaagggtgt | aaacgaaagg | 360 |
| cttgtagaaa | tccaaaagaa | cagagatatg | ttccttcctc | cggggttgta | tcctcaggct | 420 |
| caggcccctc | aaacaaacag | agttgatagc | aggcatctgg | ctgcttcggt | tgatgaaatc | 480 |
| catgttgttg | gagcagaaat | caaggaagct | actgatagta | tggtagaaat | gatcgtcggc | 540 |
| tatggccatc | agagcaggat | atcagtttat | gggatcgttg | gatgggagg | aattggcaag | 600 |
| acaactttag | ctcagaagat | atacaatgat | cgtaggataa | gagagagatt | tcaccaggtc | 660 |
| ctcatctggc | tgtccatttc | acagagcatt | gccgagaatg | atctactcaa | ggaggccatc | 720 |
| gaaaaggcag | gagggcagtg | caatcagcac | aagagtaagg | atcagctcgt | gcaaattctg | 780 |
| ctacattcca | tcagtgggaa | gagtgtcttt | cttgtgctgg | ataacgttac | caaccctgat | 840 |
| gtgtggatcg | atcttctccg | ctctccgatg | gagaggtgtt | tggatgctca | tgtacttgtt | 900 |
| accacaagga | gcggtcacgt | attgtcacag | atgaatgcgg | ttcatgtcaa | ggaaatgcat | 960 |
| agactaaagg | atgctgatgg | cctagaactg | cttatgaaga | gatcttttcag | aactgaagat | 1020 |
| gaagtaaatg | tattcagtga | tattggagca | aaaattgtta | agaaatgtga | tggccttccg | 1080 |
| cttgccatca | aggtcattgg | gggcgtccta | tcatccaggt | cgagcaaaga | agaatgggag | 1140 |
| agaatactgg | agagaagatg | gtctattgat | gggcttccag | aagaactaga | aggtgctttg | 1200 |
| tacttaagct | acagtgactt | acacccacaa | ctgaaacagt | gcttcctctg | gtgtgccttg | 1260 |
| ttgccccaga | atttcgatat | tcaccgagat | gtcacatact | ggtggattgc | tgaaggtctt | 1320 |
| gtgaaggaag | agaccagtgg | accaatacat | aacgtcgccg | aagattacta | ccatgagctg | 1380 |
| atcaagagga | atctgctaca | ggcaaggcca | gagtatgtcg | acaagggaat | atcgacaatg | 1440 |
| catgacctgt | taaggcaact | tggccaattt | ctgacaagga | atgaagccgt | cttcatgaac | 1500 |
| gagaagcgtg | atcgttgccc | ttctagtatt | cgccgattag | tgtcgggag | cgctgttgac | 1560 |
| gaaataccct | ctatagaaga | gaagaagcgc | ctacggtgcc | tcattgtctt | ggatcacgac | 1620 |
| acatgcagat | cggtgaagag | ggacatcttc | agaaagctgg | tgcatcttcg | catcttagtt | 1680 |
| ctacgtggag | caggcctcga | gagcataccct | gcatcggtgg | gttacttggc | gctgctgagg | 1740 |
| ctgctggatc | tcagctacaa | cgagatcaag | gagcttccgg | ggtccatcgg | aaaccttacc | 1800 |
| agccttggtt | gcctttcagt | gtttggttgc | acaaagttgg | cagctttgcc | acaaagtctg | 1860 |
| atgaggctga | ccacaataag | cttcctccag | ataggaaaca | caggactggc | gcaggttccg | 1920 |
| aaaggtattg | agaatttcag | gcagatagat | aaccttagat | cagttttcca | aaacggtact | 1980 |
| gatggtttca | gattagatga | actgagggca | ctctccatga | tacgacgcct | ctgggttatc | 2040 |
| cggctggaga | cagcgacacc | gccaactgag | cccgtattgt | gcgacaaggg | ttacctgaaa | 2100 |

```
gagctaggcc tgcgctgtac catgggcaag aagccaatt gtcgaactca ctacccggac    2160
agtaaggtga agaggattga ggagatctac gagagttctt gcccaccgcc aagcctaagc    2220 tacgtctttta ttgatgggtt ccctggtcgc atgtttccaa cttggctatc tttagaaccg    2280
cagaataaac ttccaaacct ggctcatatg cacttctatg actgcatatc ctgcccgaag    2340
cttcccccag caggccagct actaccgttt ctgcaggttc ttcacgtcaa aggagctgat    2400
gcagtggtga acataggtgc tgagctcctc ggaaacggca tcccatctgg aacacatacc    2460
actgcttttc caaagctcga gctgcttgag atcctcgaca tgtacaactg cagaattgg     2520 tcactaagca tggataccct tgttcgagaac acacaacagc aattccttat gccatgcctt    2580
acacgcctgc ggctgataaa ttgccccaag ttgagagctc tccctgatca tcttcacaga    2640
gttgtcaatc tacaaaggat ccaaatagaa ggagctgaca gcctgcagga ggttgtcaac    2700
catcccgggg ttgtgtggct caaggttaag aacaacaagt ccttgaggaa tatatccaac    2760
cttcctaagc tgcgcctctt gcttgcacaa gattgccaag aattgcagca ggcagagaac    2820
cttagctcac tcaaggcctt gtacgttgtc gattgcccta tggagcagat actctggaag    2880 tgtttccccca tagaacaaca gagcacgatt gtccgtgttg tcaccactgg ggcccatggt    2940
caggatattt atcctcttga atcagtattt cattaa                              2976

<210> SEQ ID NO 32
<211> LENGTH: 2976
<212> TYPE: DNA
<213> ORGANISM: Sorghum SC283 variant

<400> SEQUENCE: 32
atgggctcag tgttgtttag tctatcatcc aaatgccttg acaagcttgc tgtactgctg     60
gaggaggagg ttatgatgac gctttctgtg cgtaaagata tcaggaagct ccatgactac    120
ctcaagtact tcaattccat tcgtgacgat gctgatgctc gggcaatgga acacagagag    180
acgacaggaa tatggtgggg tgacgtgaaa gatgtcatgt atgatgttga tgacatcata    240
gatcttttga gggctcactc tcagaagcaa cgatgttgtg atttacgcat gctctctagg    300
tttgcacaac ttcaatttga ccacatgatt gccagaaaaa tcaagggtgt aaacgaaagg    360
cttgtagaaa tccaaaagaa cagagatatg ttccttcctc cggggttgta tcctcaggct    420
caggcccctc aaacaaacag agttgatagc aggcatctgg ctgcttcggt tgatgaaatc    480
catgttgttg gagcagaaat caaggaagct actgatagta tggtagaaat gatcgtcggc    540
tatggccatc agagcaggat atcagtttat gggatcgttg ggatgggagg aattggcaag    600
acaactttag ctcagaagat atacaatgat cgtaggataa gagagagatt tcaccaggtc    660
ctcatctggc tgtccatttc acagagcatt gccgagaatg atctactcaa ggaggccatc    720
gaaaaggcag gagggcagtg caatcagcac aagagtaagg atcagctcgt gcaaattctg    780
ctacattcca tcagtgggaa gagtgtcttt cttgtgctgg ataacgttac caaccctgat    840
gtgtggatcg atcttctccg ctctccgatg gagaggtgtt tggatgctca tgtacttgtt    900
accacaagga gcggtcacgt attgtcacag atgaatgcgg ttcatgtcaa ggaaatgcat    960
agactaaagg atgctgatgg cctagaactg cttatgaaga atctttcag aactgaagat    1020 gaagtaaatg tattcagtga tattggagca aaaattgtta agaaatgtga tggccttccg    1080
cttgccatca aggtcattgg gggcgtccta tcatccaggt cgagcaaaga agaatgggag    1140
agaatactgg agaagaatg gtctattgat gggcttccag aagaactaga aggtgctttg    1200
tacttaagct acagtgactt acacccacaa ctgaaacagt gcttcctctg gtgtgccttg    1260
```

```
ttgccccaga atttcgatat tcaccgagat gtcacatact ggtggattgc tgaaggtctt    1320
gtgaaggaag agaccagtgg accaatacat aacgtcgccg aagattacta ccatgagctg    1380
atcaagagga atctgctaca ggcaaggcca gagtatgtcg acaagggaat atcgacaatg    1440
catgacctgt taaggcaact tggccaattt ctgacaagga atgaagccgt cttcatgaac    1500
gagaagcgtg atcgttgccc ttctagtatt cgccgattag gtgtcgggag cgctgttgac    1560
gaaataccct ctatagaaga gaagaagcgc tacggtgcc tcattgtctt ggatcacgac    1620
acatgcagat cggtgaagag ggacatcttc agaaagctgg tgcatcttcg catcttagtt    1680
ctacgtggag caggcctcga gagcatacct gcatcggtgg gttacttggc gctgctgagg    1740
ctgctggatc tcagctacaa cgagatcaag gagcttccgg ggtccatcgg aaaccttacc    1800
agccttggtt gcctttcagt gtttggttgc acaaagttgg cagctttgcc acaaagtctg    1860
atgaggctga ccacaataag cttcctccag ataggaaaca caggactggc gcaggttccg    1920
aaaggtattg agaatttcag gcagatagat aaccttagat cagttttcca aaacggtact    1980
gatggtttca gattagatga actgagggca ctctccatga tacgacgcct ctgggttatc    2040
cggctggaga cagcgacacc gccaactgag cccgtattgt gcgacaaggg ttacctgaaa    2100
gagctaggcc tgcgctgtac catgggcaag gaagccaatt gtcgaactca ctacccggac    2160
agtaaggtga gaggattga ggagatctac gagagttttt gcccaccgcc aagcctaagc    2220 tacgtctta ttgatgggtt ccctggtcgc atgtttccaa cttggctatc tttagaaccg    2280
cagaataaac ttccaaacct ggctcatatg cacttctatg actgcatatc ctgcccgaag    2340
cttcccccag caggccagct actaccgttt ctgcaggttc ttcacgtcaa aggagctgat    2400
gcagtggtga acataggtgc tgagctcctc ggaaacggca tcccatctgg aacacatacc    2460
actgcttttc caaagctcga gctgcttgag atcctcgaca tgtacaactg cagaattgg    2520 tcactaagca tggatacctt gttcgagaac acacaacagc aattccttat gccatgcctt    2580
acacgcctgc ggctgataaa ttgccccaag ttgagagctc tccctgatca tcttcacaga    2640
gttgtcaatc tacaaaggat ccaaatagaa ggagctgaca gcctgcagga ggttgtcaac    2700
catcccgggg ttgtgtggct caaggttaag aacaacaagt ccttgaggaa tatatccaac    2760
cttcctaagc tgcgcctctt gcttgcacaa gattgccaag aattgcagca ggcagagaac    2820
cttagctcac tcaaggcctt gtacgttgtc gattgcccta tggagcagat actctggaag    2880
tgtttcccca tagaacaaca gagcacgatt gtccgtgttg tcaccactgg ggcccatggt    2940
caggatattt atcctcttga atcagtattt cattaa                              2976

<210> SEQ ID NO 33
<211> LENGTH: 2975
<212> TYPE: DNA
<213> ORGANISM: Sorghum variant P1525695

<400> SEQUENCE: 33
atgggctcgg tgttgtttag tctatcatcc aaatgccttg acaagcttgc tgtactgctg    60
gaggaggagg ttatgatgac gctttctgtg cgtaaagata tcaggaagct ccatgactac    120
ctcaagtact tcaattccat tcgtgacgat gctgatgctc gggcaatgga acacggagag    180
acgacaggaa tatggtgggg tgacgtgaaa gatgtcatgt atgatgttga tgacatcata    240
gatcttttga gggctcaccc tcagaagcaa cgatgttgtg atttacgcat gctctctagg    300
tttgcacaac ttcaatttga ccacatgatt gccagaaaaa tcaagggtgt aaacgaaagg    360
```

-continued

| | |
|---|---|
| cttgtagaaa tccaaaagaa cagagatatg ttccttcctc cggggttgta tcctcaggct | 420 |
| caggcccctc aaacaaacag agttgatagc aggcatctgg ctgcttcggt tgatgaaatc | 480 |
| catgttgttg gagcagaaat caaggaagct actgatagta tggtagaaat gatcgtcggc | 540 |
| tatggccatc agagcaggat atcagtttat gggatcgttg ggatgggagg aattggcaag | 600 |
| acaactttag ctcagaagat atacaatgat tgtaggataa gagagagatt tcaccaggtc | 660 |
| ctcatctggc tgtccatttc acagagcatt gccgagaatg atctactcaa ggaggccatc | 720 |
| gaaaaggcag gagggcagtg caatcagcac aagagtaagg atcagctcgt gcaaattctg | 780 |
| ctacattcca tcagtgggaa gagtgtcttt cttgtgctgg ataacgctac caaccctgat | 840 |
| gtgtggatcg atcttctccg ctctccgatg gagaggtgtt tggatgctca tgtacttgtt | 900 |
| accacaagga gcggtcacgt attgtcacag atgaatgcgg ttcatgtcaa ggaaatgcat | 960 |
| agactaaagg atgctgatgg cctagaactg cttatgaaga gatcttcag aactgaagat | 1020 |
| gaagtaaatg tattcagtga tattggagca aaaattgtta agaaatgtga tggccttccg | 1080 |
| cttgccatca aggtcattgg gggcgtccta tcatccaggt cgagcaaaga agaatgggag | 1140 |
| agaatactgg agagaagatg gtctattgat gggcttccag aagaactaga aggtgctctg | 1200 |
| tacttaagct acagtgactt acacccacaa ctgaaacagt gcttcctctg gtgtgccttg | 1260 |
| ttgccccaga atttcgatat tcaccgagat gtcacatact ggtggattgc tgaaggtctt | 1320 |
| gtgaaggaag agaccagtgg accaatacat aacgtcgccg aagattacta ccatgagctg | 1380 |
| atcaagagga acctgctaca ggcaaggcca gagtatgtcg acaagggagt atcgacaatg | 1440 |
| catgacctgt tgaggcaact tggccaattt ctgacaagaa atgaagccat cttcatgaac | 1500 |
| gagaagcgtg atcgttgccc ttgaagtatt cgccgactag gtgtcgggag cgctgttgac | 1560 |
| gaaataccct ctatagaaga gaagaagcgc tacggtgcc tcattgtctt gcatcacgac | 1620 |
| acatgcagat cggtgaagag ggacatcttc agaaagttgg tgcatcttcg catcttagtt | 1680 |
| ctacgtggag caggccttga gagcataccct gcatcggtgg gttacttggc gctgctgagg | 1740 |
| ctgctggatc tcagctacaa tgagatcaag gagcttccag ggtccatcgg aaaccttacc | 1800 |
| agccttggtt gcctttcagt gtttggttgc acaaagttgg cagctttgcc gacaagtctg | 1860 |
| atgaggctga ccacaataag cttcctcaaa ataggaaaca caggactggc gcaggttccg | 1920 |
| aaaggtattg agaatttcaa gcagatggat aaccttagat cagttttcca aaacggtact | 1980 |
| gatggtttca gattagatga actgagggca ctctctatga tacgacgcct ctgggttatc | 2040 |
| cggctggaga cagcgatacc gccaactgag cccatactgt gcgacaaggg ttacctgaaa | 2100 |
| gagctaggcc tgcgctgcac catgggtaag gaagccaatt gtcgaactca ctatccggac | 2160 |
| agcaaggtga agaggattga ggagatctac gagagttttt gcccaccgcc aagcctaagc | 2220 |
| tacgtcttca ttgatgggtt ccctggttgc atgtttccaa cttggctatc ttcagaaccg | 2280 |
| cagaataaac tgcaaacctg gctcatatgc acttcaacga ctgcatatcc tgcccgaagc | 2340 |
| ttcccccagc aggccagcta ctaccgtttc tgcaggttct tcacgtcaaa ggagctgacg | 2400 |
| cagtagtgag gataggtgct gagctcctcg gaaacagcat cccatccgga acacatacca | 2460 |
| ctgcttttcc aaagctcgag ctgcttgaga tcctcgacat gtacaactgg cagaattggt | 2520 |
| cactaagcat ggataccttg ttcgagaaca cacaacagca attccttatg ccatgcctta | 2580 |
| cacggctgcg gctgataaat tgccccaagt tgagagctct ccctgatcat cttcacagag | 2640 |
| ttgtcaatct acaaaggatc caaatagaag gagctgacga cctgcaggag attgtcaacc | 2700 |
| atcccggggt tgtgtggctc aaggttaaga acaacaagtc cttgaggaat atatccaacc | 2760 |

```
ttcctaagct gcgcctcttg cttgcacaag attgccaaga attgcagcag gcagagaacc    2820
ttagctcact caaggccttg tacgttgtcg attgccctat ggagcagata ctctggaagt    2880
gtttccccat agaacaacag agcacaattg tccgtgttgt caccactggg gcccatggtc    2940
aggatattta tcctcttgaa tcagtatttc attaa                              2975

<210> SEQ ID NO 34
<211> LENGTH: 2975
<212> TYPE: DNA
<213> ORGANISM: Sorghum variant Ai4

<400> SEQUENCE: 34
atgggctcag tgttgtttag tctatcatcc aaatgccttg acaagcttgc tgtactgctg      60
gaggaggaga ttatgatgac gctatctgtg cgtaaagaga tcaggaagct ccatgaaaac     120
ctcaagtact ttaattccat tcatgacgat gctgatgctc gggcaatgga acacagagag     180
atgacaggaa tatggtgggg tgacgtgaaa gatgtcatgt atgatgttga tgacatcata     240
gatcttttga gggctcactc tcagaagcaa cgatgttgtg atttacgcat gctctctagg     300
tttgcacaac ttcaatttga ccacatgatt gccagaaaaa tcaagggtgt aaacgaaagg     360
cttgtagaaa tccaaaagaa cagagatatg ttccttcctc cggggttgta tcctcaggct     420
caggcccctc aaacaaacgg agttgatagc aggcatctgg ctgcttcggt tgatgaaatc     480
catgttgttg gagcagaaat caaggaagct actgatagta tggtagaaat gattgtcggc     540
tatggccatc agagcaggat atcagtttat gggatcgttg ggatgggagg aattggtaag     600
acaactttag ctcagaagat atacaatgat cgtaggataa gagagagatt tcaccaggtc     660
ctcatctggc tgtccatttc acagagcatt gccgagaatg atctactcaa ggaggccatc     720
gaaaaggcag gagggcagtg caatcagcac aagagtaagg atcagctcgt gcaaattctg     780
ctacattcca tcagtgggaa gagtgtcttt cttgtgctgg ataacgttac caaccctgat     840
gtgtggatcg atcttctccg ctctccgatg gagaggtgtt tggatgctca tgtacttgtt     900
accacaagga gcggtcgcgt attgtcacag atgaatgcgg tgcatgtcaa ggaaatgcac     960
agactaaagg atgctgatgg cctagaactg cttatgaaga gatcttttcag aaccaaagat    1020 gaagtaaatg tattcagtga tattggagca aaaattgtta agaaatgtga gggccttcct    1080
cttgccatca aggtcattgg aggcgtccta tcatccaggt cgagcaaaga gaatgggag     1140 agaatactgg agagaagatg gtctattgat gggcttccag aagaactaga aggtgctttg    1200
tacttaagct acagtgactt acacccacaa ctcaaacagt gcttcctctg ctgtgccctg    1260
ttgcctcaga atttcgatat tcaccgagat gtcacatact ggtggattgc tgaaggtttt    1320
gtgaaggaag agggcagcgg accgatacat aacattgccg aagattacta ccatgagctg    1380
atcaagagga atctgctaca ggcaaggcca gagtatgtcg acaagggagt atcgacaatg    1440
catgacctgt tgaggcaact tggccaattt ctgacaagaa atgaagccat cttcatgaac    1500
gagaagcgtg atcgttgcct ttgaagtatt cgccgactag gtgtcgggag cgctgttgac    1560
gaaatacctt ctatagaaga gaagaagcgc tacggtgcc tcattgtctt gcatcacgac     1620
acatgcagat cggtgaagag ggacatcttc agaaagtttg tgcatcttcg catcttagtt    1680
ctacgtggag caggccttga gagcatacct gcatcggtgg gttacttggc gctgctgagg    1740
ctgctggatc tcagctacaa tgagatcaag gagcttccag gtccatcgg aaaccttacc     1800 agccttggtt gcctttcagt gtttggttgc acaaagttgg cagctttgcc gacaagtctg    1860
```

```
atgaggctga ccacaataag cttcctcaaa ataggaaaca caggactggc gcaggttccg      1920
aaaggtattg agaatttcaa gcagatggat aaccttagat cagttttcca aaacagtact      1980
gatggtttca gattagatga actgagggca ctctctatga tacgacgcct ctgggttatc      2040
cggctggaga cagcgatacc gccaactgag cccatactgt gcgacaaggg ttacctgaaa      2100
gagctaggcc tgcgctgcac catgggtaag gaagccaatt gtcgaactca ctatccggac      2160
agcaaggtga agaggattga ggagatctac gagagttttt gcccaccgcc aagcctaagc      2220
tacgtcttca ttgatgggtt ccctggttgc atgtttccaa cttggctatc ttcagaaccg      2280
cagaataaac tgcaaacctg gctcatatgc acttcaacga ctgcatatcc tgcccgaagc      2340
ttcccccagc aggccagcta ctaccgtttc tgcaggttct tcacgtcaaa ggagctgacg      2400
cagtagtgaa cataggtgct gagctcctcg gaaacagcat cccatccgga acacatacca      2460
ctgcttttcc aaagctcgag ctgcttgaga tcctcgacat gtacaactgg cagaattggt      2520
cactaagcat ggataccttg ttcgagaaca cacaacagca attccttatg ccatgcctta      2580
cacggctgcg gctgataaat tgccccaagt tgagagctct ccctgatcat cttcacagag      2640
ttgtcaatct acaaaggatc caaatagaag gagctgacag cctgcaggag attgtcaacc      2700
atcccggggt tgtgtggctc aaggttaaga caacaagtc cttgaggaat atatccaacc       2760
ttcctaagct gtgcctcttg cttgcacaag attgccaaga attgcagcag gcagagaacc      2820
ttagctcact caaggccttg tacgttgtcg attgccctat ggagcagata ctctggaagt      2880
gtttccccat agaacaacag agcacgattg tccgtgttgt caccactggg gcccatggtc      2940
aggatattta tcctcttgaa tcagtatttc attaa                                 2975

<210> SEQ ID NO 35
<211> LENGTH: 2975
<212> TYPE: DNA
<213> ORGANISM: Sorghum variant SQR

<400> SEQUENCE: 35
atgggctcag tgttgtttag tctatcatcc aaatgccttg acaagcttgc tgtactgctg        60
gaggaggaga ttatgatgac gctatctgtg cgtaaagaga tcaggaagct ccatgaaaac       120
ctcaagtact ttaattccat tcatgacgat gctgatgctc gggcaatgga acacagagag       180
atgacaggaa tatggtgggg tgacgtgaaa gatgtcatgt atgatgttga tgacatcata       240
gatcttttga gggctcactc tcagaagcaa cgatgttgtg atttacgcat gctctctagg       300
tttgcacaac ttcaatttga ccacatgatt gccagaaaaa tcaagggtgt aaacgaaagg       360
cttgtagaaa tccaaaagaa cagagatatg ttccttcctc cggggttgta tcctcaggct       420
caggcccctc aaacaaacgg agttgatagc aggcatctgg ctgcttcggt tgatgaaatc       480
catgttgttg gagcagaaat caaggaagct actgatagta tggtagaaat gattgtcggc       540
tatggccatc agagcaggat atcagtttat gggatcgttg ggatgggagg aattggtaag       600
acaactttag ctcagaagat atacaatgat cgtaggataa gagagagatt tcaccaggtc       660
ctcatctggc tgtccatttc acagagcatt gccgagaatg atctactcaa ggaggccatc       720
gaaaaggcag gagggcagtg caatcagcac aagagtaagg atcagctcgt gcaaattctg       780
ctacattcca tcagtgggaa gagtgtcttt cttgtgctgg ataacgttac caaccctgat       840
gtgtggatcg atcttctccg ctctccgatg gagaggtgtt tggatgctca tgtacttgtt       900
accacaagga gcggtcgcgt attgtcacag atgaatgcgg tgcatgtcaa ggaaatgcac       960
agactaaagg atgctgatgg cctagaactg cttatgaaga gatctttcag aaccaaagat      1020
```

```
gaagtaaatg tattcagtga tattggagca aaaattgtta agaaatgtga gggccttcct      1080
cttgccatca aggtcattgg aggcgtccta tcatccaggt cgagcaaaga agaatgggag      1140
agaatactgg agagaagatg gtctattgat gggcttccag aagaactaga aggtgctttg      1200
tacttaagct acagtgactt acacccacaa ctcaaacagt gcttcctctg ctgtgccctg      1260
ttgcctcaga atttcgatat tcaccgagat gtcacatact ggtggattgc tgaaggtttt      1320
gtgaaggaag agggcagcgg accgatacat aacattgccg aagattacta ccatgagctg      1380
atcaagagga atctgctaca ggcaaggcca gagtatgtcg acaagggagt atcgacaatg      1440
catgacctgt tgaggcaact tggccaattt ctgacaagaa atgaagccat cttcatgaac      1500
gagaagcgtg atcgttgcct ttgaagtatt cgccgactag gtgtcgggag cgctgttgac      1560
gaaatacctt ctatagaaga gaagaagcgc tacggtgcc tcattgtctt gcatcacgac       1620
acatgcagat cggtgaagag ggacatcttc agaaagttgg tgcatcttcg catcttagtt      1680
ctacgtggag caggccttga gagcataccct gcatcggtgg gttacttggc gctgctgagg     1740
ctgctggatc tcagctacaa tgagatcaag gagcttccag ggtccatcgg aaaccttacc      1800
agccttggtt gcctttcagt gtttggttgc acaaagttgg cagctttgcc gacaagtctg      1860
atgaggctga ccacaataag cttcctcaaa ataggaaaca caggactggc gcaggttccg      1920
aaaggtattg agaatttcaa gcagatggat aaccttagat cagttttcca aaacagtact      1980
gatggtttca gattagatga actgagggca ctctctatga tacgacgcct ctgggttatc      2040
cggctggaga cagcgatacc gccaactgag cccatactgt gcgacaaggg ttacctgaaa      2100
gagctaggcc tgcgctgcac catgggtaag gaagccaatt gtcgaactca ctatccggac      2160
agcaaggtga agaggattga ggagatctac gagagttttt gcccaccgcc aagcctaagc      2220
tacgtcttca ttgatgggtt ccctggttgc atgtttccaa cttggctatc ttcagaaccg      2280
cagaataaac tgcaaacctg gctcatatgc acttcaacga ctgcatatcc tgcccgaagc      2340
ttcccccagc aggccagcta ctaccgtttc tgcaggttct tcacgtcaaa ggagctgacg      2400
cagtagtgaa cataggtgct gagctcctcg gaaacagcat cccatccgga acacatacca      2460
ctgcttttcc aaagctcgag ctgcttgaga tcctcgacat gtacaactgg cagaattggt      2520
cactaagcat ggatacctg ttcgagaaca cacaacagca attccttatg ccatgcctta      2580
cacggctgcg gctgataaat tgccccaagt tgagagctct ccctgatcat cttcacagag      2640
ttgtcaatct acaaaggatc caaatagaag gagctgacag cctgcaggag attgtcaacc      2700
atcccggggt tgtgtggctc aaggttaaga caacaagtc cttgaggaat atatccaacc      2760
ttcctaagct gtgcctcttg cttgcacaag attgccaaga attgcagcag gcagagaacc      2820
ttagctcact caaggccttg tacgttgtcg attgccctat ggagcagata tctctggaagt      2880 gtttccccat agaacaacag agcacgattg tccgtgttgt caccactggg gcccatggtc      2940
aggatattta tcctcttgaa tcagtatttc attaa                                 2975

<210> SEQ ID NO 36
<211> LENGTH: 2975
<212> TYPE: DNA
<213> ORGANISM: Sorghym variant PQ434

<400> SEQUENCE: 36
atgggctcag tgttgtttag tctatcatcc aaatgccttg acaagcttgc tgtactgctg        60
gaggaggaga ttatgatgac gctatctgtg cgtaaagaga tcaggaagct ccatgactac       120
```

```
ctcaagtact ttaattccat tcatgacgat gctgatgctc gggcaatgga acacagagag    180
atgacaggaa tatggtgggg tgacgtgaaa gatgtcatgt atgatgttga tgacatcata    240
gatcttttga gggctcactc tcagaagcaa cgatgttgtg atttacgcat gctctctagg    300
tttgcacaac ttcaatttga ccacatgatt gccagaaaaa tcaagggtgt aaacgaaagg    360
cttgtagaaa tccaaaagaa cagagatatg ttccttcctc cggggttgta tcctcaggct    420
caggcccctc aaacaaacgg agttgatagc aggcatctgg ctgcttcggt tgatgaaatc    480
catgttgttg gagcagaaat caaggaagct actgatagta tggtagaaat gattgtcggc    540
tatggccatc agagcaggat atcagtttat gggatcgttg gatgggagg aattggtaag     600 acaactttag ctcagaagat atacaatgat cgtaggataa gagagagatt tcaccaggtc    660
ctcatctggc tgtccatttc acagagcatt gccgagaatg atctactcaa ggaggccatc    720
gaaaaggcag gagggcagtg caatcagcac aagagtaagg atcagctcgt gcaaattctg    780
ctacattcca tcagtgggaa gagtgtcttt cttgtgctgg ataacgttac caaccctgat    840
gtgtggatcg atcttctccg ctctccgatg gagaggtgtt tggatgctca tgtacttgtt    900
accacaagga gcggtcgcgt attgtcacag atgaatgcgg tgcatgtcaa ggaaatgcac    960
agactaaagg atgctgatgg cctagaactg cttatgaaga gatcttttcag aaccaaagat   1020 gaagtaaatg tattcagtga tattggagca aaaattgtta agaaatgtga gggccttcct   1080
cttgccatca aggtcattgg aggcgtccta tcatccaggt cgagcaaaga gaatgggag    1140 agaatactgg agagaagatg gtctattgat gggcttccag aagaactaga aggtgctttg   1200
tacttaagct acagtgactt acacccacaa ctcaaacagt gcttcctctg ctgtgccctg   1260
ttgcctcaga atttcgatat tcaccgagat gtcacatact ggtggattgc tgaaggtttt   1320
gtgaaggaag agggcagcgg accgatacat aacattgccg aagattacta ccatgagctg   1380
atcaagagga atctgctaca ggcaaggcca gagtatgtcg acaagggagt atcgacaatg   1440
catgacctgt tgaggcaact tggccaattt ctgacaagaa atgaagccat cttcatgaac   1500
gagaagcgtg atcgttgcct ttgaagtatt cgccgactag gtgtcgggag cgctgttgac   1560
gaaatacctt ctatagaaga gaagaagcgc tacggtgcc tcattgtctt gcatcacgac    1620
acatgcagat cggtgaagag ggacatcttc agaaagttgg tgcatcttcg catcttagtt   1680
ctacgtggag caggccttga gagcatacct gcatcggtgg gttacttggc gctgctgagg   1740
ctgctggatc tcagctacaa tgagatcaag gagcttccag ggtccatcgg aaaccttacc   1800
agccttggtt gcctttcagt gtttggttgc acaaagttgg cagctttgcc gacaagtctg   1860
atgaggctga ccacaataag cttcctcaaa ataggaaaca caggactggc gcaggttccg   1920
aaaggtattg agaatttcaa gcagatggat aaccttagat cagtttttcca aaacggtact   1980 gatggtttca gattagatga actgagggca ctctctatga tacgacgcct ctgggttatc   2040
cggctggaga cagcgatacc gccaactgag cccatactgt gcgacaaggg ttacctgaaa    2100
gagctaggcc tgcgctgcac catgggtaag gaagccaatt gtcgaactca ctatccagac   2160
agcaaggtga agaggattga ggagatctat gagagttttt gcccaccgcc aagcctaagc   2220
tacgtcttca ttgatgggtt ccctggttgc atgtttccaa cttggctatc ttcagaaccg   2280
cagaataaac tgcaaacctg gctcatatgc acttcaacga ctgcatatcc tgcccgaagc   2340
ttcccccagc aggccagcta ctaccatttc tgcaggttct tcacgtcaaa ggagctgacg   2400
cagtagtgaa cataggtgct gagctcctcg gaaacagcat cccatccgga acacatacca   2460
ctgcttttcc aaagctcgag ctgcttgaga tcctcgacat gtacaactgg cagaattggt   2520
```

```
cactaagcat ggataccttg ttcgagaaca cacaacagca attccttatg ccatgcctta    2580
cacggctgcg gctgataaat tgccccaagt tgagagctct ccctgatcat cttcacagag    2640
ttgtcaatct acaaaggatc caaatagaag gagctgacag cctgcaggag attgtcaacc    2700
atcccagggt tgtgtggctc aaggttaaga caacaagtc cttgaggaat atatccaacc     2760
ttcctaagct gcgcctcttg cttgcacaag attgccaaga attgcagcag gcagagaacc    2820
ttagctcact caaggccttg tacgttgtcg attgccctat ggagcagata ctctggaagt    2880
gtttccccat agaacaacag agcacgattg tccgtgttgt caccactggg gcccatggtc    2940
aggatattta tcctcttgaa tcagtatttc attaa                               2975

<210> SEQ ID NO 37
<211> LENGTH: 2975
<212> TYPE: DNA
<213> ORGANISM: Sorghum variants 555, KP33, and Tetron

<400> SEQUENCE: 37
atgggctcag tgttgtttag tctatcatcc aaatgccttg acaagcttgc tgtactgctg    60
gaggaggaga ttatgatgac gctatctgtg cgtaaagaga tcaggaagct ccatgactac    120
ctcaagtact ttaattccat tcatgacgat gctgatgctc gggcaatgga acacagagag    180
atgacaggaa tatggtgggg tgacgtgaaa gatgtcatgt atgatgttga tgacatcata    240
gatcttttga gggctcactc tcagaagcaa cgatgttgtg atttacgcat gctctctagg    300
tttgcacaac ttcaatttga ccacatgatt gccagaaaaa tcaagggtgt aaacgaaagg    360
cttgtagaaa tccaaaagaa cagagatatg ttccttcctc cggggttgta tcctcaggct    420
caggcccctc aaacaaacgg agttgatagc aggcatctgg ctgcttcggt tgatgaaatc    480
catgttgttg gagcagaaat caaggaagct actgatagta tggtagaaat gattgtcggc    540
tatggccatc agagcaggat atcagtttgt gggatcgttg ggatgggagg aattggtaag    600
acaactttag ctcagaagat atacaatgat cgtaggataa gagagagatt tcaccaggtc    660
ctcatctggc tgtccatttc acagggcatt gccgagaatg atctactcaa ggaggccatc    720
gaaaaggcag gagggcagtg caatcagcac aagagtaagg atcagctcgt gcaaattctg    780
ctacattcca tcagtgggaa gagtgtcttt cttgtgctgg ataacgttac caaccctgat    840
gtgtggatcg atcttctccg ctctccgatg gagaggtgtt tggatgctca tgtacttgtt    900
accacaagga gcggtcacgt attgtcacag atgaatgcgg tgcatgtcaa ggaaatgcac    960
agactaaagg atgctgatgg cctagaactg cttatgaaga gatcttttcag aaccaaagat    1020 gaagtaaatg tattcagtga tattggagca aaaattgtta agaaatgtga gtgccttcct    1080
cttgccatca aggtcattgg aggcgtccta tcatccaggt cgagcaaaga gaatgggag    1140 agaatactgg agagaagatg gtctattgat gggcttccag aagaactaga aggtgctttg    1200
tacttaagct acagtgactt acacccacaa ctcaaacagt gcttcctctg ctgtgccctg    1260
ttgcctcaga atttcgatat tcaccgagat gtcacatact ggtggattgc tgaaggtttt    1320
gtgaaggaag agggcagcgg accgatacat aacattgccg aagattacta ccatgagctg    1380
atcaaggaga atctgctaca ggcaaggcca gagtatgtcg acaagggagt atcgacaatg    1440
catgacctgt tgaggcaact tggccaattt ctgaaaagaa atgaagccat cttcatgaac    1500
gagaagcgtg aacgttgcct ttgaagtatt cgccgactag gtgtcgggag cgctgttgac    1560
gaaataccct ctatagaaga gaagaagcgc ctacggtgcc tcattgtctt gcatcacgac    1620
```

-continued

| | |
|---|---|
| acatgcagat cggtgaagag ggacatcttc agaaagttgg tgcatcttcg catcttagtt | 1680 |
| ctacgtggag caggccttga gagcatacct gcatcggtgg gttacttggc gctgctgagg | 1740 |
| ctgctggatc tcagctacaa tgagatcaag gagcttccag ggtccatcgg aaaccttacc | 1800 |
| agccttggtt gcctttcagt gtttggttgc acaaagttgg cagctttgcc aacaagtctg | 1860 |
| atgaggctga ccacaataag cttcctcaaa ataggaaaca caggactggc gcaggttccg | 1920 |
| aaaggtattg agaatttcaa gcagatggat aaccttagat cagttttcca aaacggtact | 1980 |
| gatggtttca gattagatga actgagggca ctctctatga tacgacgcct ctgggttatc | 2040 |
| cggctggaga cagcgatacc gccaactgag cccatactgt gcgacaaggg ttacctgaaa | 2100 |
| gagctaggcc tgcgctgcac catgggtaag gaagccaatt gtcgaactca ccatccggac | 2160 |
| agcaaggtga ggaggattga ggagatctac gagagttttt gcccaccgcc aggcctaagc | 2220 |
| tacgtcttca ttgatgggtt ccctggttgc atgtttccaa cttggctatc ttcagaaccg | 2280 |
| cagaataaac tgcaagcctg gctcatatgc acttcaacga ctgcatatcc tgcccgaagc | 2340 |
| ttcccccagc aggccagcta ctaccgtttc tgcaggttct tcacgtcaaa ggagctgacg | 2400 |
| cagtagtgaa cataggtgct gagctcctcg gaaacagcat cccatccgga acacatacca | 2460 |
| ctgcttttcc aaagctcgag ctgcttgaga tcctcgacat gtacaactgg cagaattggt | 2520 |
| cactaagcat ggatacctg ttcgagaaca cacaacagca attccttatg ccatgcctta | 2580 |
| cacggctgcg gctgataaat tgccccaagt tgagagctct ccctgatcat cttcacagag | 2640 |
| ttgtcaatct acaaaggatc caaatagaag gagctgacag cctgcaggag attgtcaacc | 2700 |
| atcccggggt tgtgtggctc aaggttaaga caacaagtc cttgaggaat atatccaacc | 2760 |
| ttcctaagct gcgcctcttg cttgcacaag attgccaaga attgcagcag cagagaacc | 2820 |
| ttagctcact caaggcctg tacgttgtcg attgccctat ggagcagata tctctggaagt | 2880 |
| gtttccccat agaacaacag agcacgattg tccgtgttgt caccactggg gcccatggtc | 2940 |
| aggatattta tcctcttgaa tcagtatttc attaa | 2975 |

<210> SEQ ID NO 38
<211> LENGTH: 2975
<212> TYPE: DNA
<213> ORGANISM: Sorghum variants 1085, Ajabsido, BTX623, BTX631, BTX642,
ICSV745, IS9830, Ji2731, Keller, M35-1, Macia, P1563516, Rio,
SC23, SC52, SC55, SC56, SC103, SC108C, SC110, SC155, SC170, SC301,
SC326, SC650, SC971, SC1103, SRN39, TAM428, and TX7000

<400> SEQUENCE: 38

| | |
|---|---|
| atgggctcag tgttgtttag tctatcatcc aaatgccttg acaagcttgc tgtactgctg | 60 |
| gaggaggaga ttatgatgac gctatctgtg cgtaaagaga tcaggaagct ccatgactac | 120 |
| ctcaagtact ttaattccat tcatgacgat gctgatgctc gggcaatgga acacagagag | 180 |
| atgacaggaa tatggtgggg tgacgtgaaa gatgtcatgt atgatgttga tgacatcata | 240 |
| gatcttttga gggctcactc tcagaagcaa cgatgttgtg atttacgcat gctctctagg | 300 |
| tttgcacaac ttcaatttga ccacatgatt gccagaaaaa tcaagggtgt aaacgaaagg | 360 |
| cttgtagaaa tccaaaagaa cagagatatg ttccttcctc cggggttgta tcctcaggct | 420 |
| caggcccctc aaacaaacgg agttgatagc aggcatctgg ctgcttcggt tgatgaaatc | 480 |
| catgttgttg gagcagaaat caaggaagct actgatagta tggtagaaat gattgtcggc | 540 |
| tatggccatc agagcaggat atcagtttat gggatcgttg ggatgggagg aattggtaag | 600 |
| acaactttag ctcagaagat atacaatgat cgtaggataa gagagagatt tcaccaggtc | 660 |

```
ctcatctggc tgtccatttc acagagcatt gccgagaatg atctactcaa ggaggccatc    720
gaaaaggcag gagggcagtg caatcagcac aagagtaagg atcagctcgt gcaaattctg    780
ctacattcca tcagtgggaa gagtgtcttt cttgtgctgg ataacgttac caaccctgat    840
gtgtggatcg atcttctccg ctctccgatg gagaggtgtt tggatgctca tgtacttgtt    900
accacaagga gcggtcacgt attgtcacag atgaatgcgg tgcatgtcaa ggaaatgcac    960
agactaaagg atgctgatgg cctagaactg cttatgaaga gatctttcag aaccaaagat   1020
gaagtaaatg tattcagtga tattggagca aaaattgtta agaaatgtga gtgccttcct   1080
cttgccatca aggtcattgg aggcgtccta tcatccaggt cgagcaaaga agaatgggag   1140
agaatactgg agagaagatg gtctattgat gggcttccag aagaactaga aggtgctttg   1200
tacttaagct acagtgactt acacccacaa ctcaaacagt gcttcctctg ctgtgccctg   1260
ttgcctcaga atttcgatat tcaccgagat gtcacatact ggtggattgc tgaaggtttt   1320
gtgaaggaag agggcagcgg accgatacat aacattgccg aagattacta ccatgagctg   1380
atcaagagga atctgctaca ggcaaggcca gagtatgtcg acaagggagt atcgacaatg   1440
catgacctgt tgaggcaact tggccaattt ctgaaaagaa atgaagccat cttcatgaac   1500
gagaagcgtg aacgttgcct tgaagtatt cgccgactag tgtcgggag cgctgttgac    1560
gaaatacctt ctatagaaga gaagaagcgc ctacggtgcc tcattgtctt gcatcacgac   1620
acatgcagat cggtgaagag ggacatcttc agaaagttgg tgcatcttcg catcttagtt   1680
ctacgtggag caggccttga gagcatacct gcatcggtgg gttacttggc gctgctgagg   1740
ctgctggatc tcagctacaa tgagatcaag gagcttccag ggtccatcgg aaaccttacc   1800
agccttggtt gcctttcagt gtttggttgc acaaagttgg cagctttgcc aacaagtctg   1860
atgaggctga ccacaataag cttcctcaaa ataggaaaca caggactggc gcaggttccg   1920
aaaggtattg agaatttcaa gcagatggat aaccttagat cagttttcca aaacggtact   1980
gatggtttca gattagatga actgagggca ctctctatga tacgacgcct ctgggttatc   2040
cggctggaga cagcgatacc gccaactgag cccatactgt gcgacaaggg ttacctgaaa   2100
gagctaggcc tgcgctgcac catgggtaag gaagccaatt gtcgaactca ctatccggac   2160
agcaaggtga agaggattga ggagatctac gagagttttt gcccaccgcc aagcctaagc   2220
tacgtcttca ttgatgggtt ccctggttgc atgtttccaa cttggctatc ttcagaaccg   2280
cagaataaac tgcaaacctg gctcatatgc acttcaacga ctgcatatcc tgcccgaagc   2340
ttcccccagc aggccagcta ctaccgtttc tgcaggttct tcacgtcaaa ggagctgacg   2400
cagtagtgaa cataggtgct gagctcctcg gaaacagcat cccatccgga acacatacca   2460
ctgcttttcc aaagctcgag ctgcttgaga tcctcgacat gtacaactgg cagaattggt   2520
cactaagcat ggataccttg ttcgagaaca cacaacagca attccttatg ccatgcctta   2580
cacggctgcg gctgataaat tgccccaagt tgagagctct ccctgatcat cttcacagag   2640
ttgtcaatct acaaaggatc caaatagaag gagctgacga cctgcaggag attgtcaacc   2700
atcccggggt tgtgtggctc aaggttaaga acaacaagtc cttgaggaat atatccaacc   2760
ttcctaagct gcgcctcttg cttgcacaag attgccaaga attgcagcag gcagagaacc   2820
ttagctcact caaggccttg tacgttgtcg attgccctat ggagcagata ctctggaagt   2880
gtttccccat agaacaacag agcacgattg tccgtgttgt caccactggg gcccatggtc   2940
aggatatttta tcctcttgaa tcagtatttc attaa                            2975
```

```
<210> SEQ ID NO 39
<211> LENGTH: 988
<212> TYPE: PRT
<213> ORGANISM: Sorghum, genotype SC283

<400> SEQUENCE: 39
```

| Met | Gly | Ser | Val | Leu | Phe | Ser | Leu | Ser | Ser | Lys | Cys | Leu | Asp | Lys | Leu |
|---|---|---|---|---|---|---|---|---|---|---|---|---|---|---|---|
| 1 | | | | 5 | | | | | 10 | | | | | 15 | |

| Ala | Val | Leu | Leu | Glu | Glu | Glu | Val | Met | Met | Thr | Leu | Ser | Val | Arg | Lys |
|---|---|---|---|---|---|---|---|---|---|---|---|---|---|---|---|
| | | | 20 | | | | | 25 | | | | | 30 | | |

| Asp | Ile | Arg | Lys | Leu | Ala | Asp | Tyr | Leu | Lys | Tyr | Phe | Asn | Ser | Ile | Arg |
|---|---|---|---|---|---|---|---|---|---|---|---|---|---|---|---|
| | | | 35 | | | | | 40 | | | | | 45 | | |

| Glu | Asp | Ala | Asp | Ala | Arg | Ala | Met | Glu | His | Arg | Glu | Thr | Thr | Gly | Ile |
|---|---|---|---|---|---|---|---|---|---|---|---|---|---|---|---|
| | 50 | | | | | 55 | | | | | 60 | | | | |

| Trp | Trp | Gly | Asp | Val | Lys | Asp | Val | Met | Tyr | Asp | Val | Asp | Asp | Ile | Leu |
|---|---|---|---|---|---|---|---|---|---|---|---|---|---|---|---|
| 65 | | | | | 70 | | | | | 75 | | | | | 80 |

| Asp | Leu | Leu | Arg | Ala | His | Ser | Gln | Lys | Gln | Arg | Cys | Cys | Asp | Leu | Arg |
|---|---|---|---|---|---|---|---|---|---|---|---|---|---|---|---|
| | | | | 85 | | | | | 90 | | | | | 95 | |

| Met | Leu | Ser | Arg | Phe | Ala | Gln | Leu | Gln | Phe | Asp | His | Met | Ile | Ala | Arg |
|---|---|---|---|---|---|---|---|---|---|---|---|---|---|---|---|
| | | | | 100 | | | | | 105 | | | | | 110 | |

| Lys | Ile | Lys | Gly | Val | Asn | Glu | Arg | Leu | Val | Glu | Ile | Gln | Lys | Asn | Arg |
|---|---|---|---|---|---|---|---|---|---|---|---|---|---|---|---|
| | | | 115 | | | | | 120 | | | | | 125 | | |

| Asp | Met | Phe | Leu | Pro | Pro | Gly | Leu | Tyr | Pro | Gln | Ala | Gln | Ala | Pro | Gln |
|---|---|---|---|---|---|---|---|---|---|---|---|---|---|---|---|
| | 130 | | | | | 135 | | | | | 140 | | | | |

| Thr | Asn | Arg | Val | Asp | Ser | Arg | His | Leu | Ala | Ala | Ser | Val | Asp | Glu | Ile |
|---|---|---|---|---|---|---|---|---|---|---|---|---|---|---|---|
| 145 | | | | | 150 | | | | | 155 | | | | | 160 |

| His | Val | Val | Gly | Ala | Glu | Ile | Lys | Glu | Ala | Thr | Asp | Ser | Met | Val | Glu |
|---|---|---|---|---|---|---|---|---|---|---|---|---|---|---|---|
| | | | | 165 | | | | | 170 | | | | | 175 | |

| Met | Ile | Val | Gly | Tyr | Gly | His | Gln | Ser | Arg | Ile | Ser | Val | Tyr | Gly | Ile |
|---|---|---|---|---|---|---|---|---|---|---|---|---|---|---|---|
| | | | 180 | | | | | 185 | | | | | 190 | | |

| Val | Gly | Met | Gly | Gly | Ile | Gly | Lys | Thr | Thr | Leu | Ala | Gln | Lys | Ile | Tyr |
|---|---|---|---|---|---|---|---|---|---|---|---|---|---|---|---|
| | | 195 | | | | | 200 | | | | | 205 | | | |

| Asn | Asp | Arg | Arg | Ile | Arg | Glu | Arg | Phe | His | Gln | Val | Leu | Ile | Trp | Leu |
|---|---|---|---|---|---|---|---|---|---|---|---|---|---|---|---|
| | 210 | | | | | 215 | | | | | 220 | | | | |

| Ser | Ile | Ser | Gln | Ser | Ile | Ala | Glu | Asn | Asp | Leu | Leu | Lys | Glu | Ala | Ile |
|---|---|---|---|---|---|---|---|---|---|---|---|---|---|---|---|
| 225 | | | | | 230 | | | | | 235 | | | | | 240 |

| Glu | Lys | Ala | Gly | Gly | Gln | Cys | Asn | Gln | His | Lys | Ser | Lys | Asp | Gln | Leu |
|---|---|---|---|---|---|---|---|---|---|---|---|---|---|---|---|
| | | | | 245 | | | | | 250 | | | | | 255 | |

| Val | Gln | Ile | Leu | Leu | His | Ser | Ile | Ser | Gly | Lys | Ser | Val | Phe | Leu | Glu |
|---|---|---|---|---|---|---|---|---|---|---|---|---|---|---|---|
| | | | 260 | | | | | 265 | | | | | 270 | | |

| Leu | Asp | Asn | Val | Thr | Asn | Pro | Asp | Val | Trp | Ile | Asp | Leu | Leu | Arg | Ser |
|---|---|---|---|---|---|---|---|---|---|---|---|---|---|---|---|
| | | 275 | | | | | 280 | | | | | 285 | | | |

| Pro | Met | Glu | Arg | Cys | Leu | Asp | Ala | His | Val | Leu | Val | Thr | Thr | Arg | Ser |
|---|---|---|---|---|---|---|---|---|---|---|---|---|---|---|---|
| | 290 | | | | | 295 | | | | | 300 | | | | |

| Gly | His | Val | Leu | Ser | Gln | Met | Asn | Ala | Val | His | Val | Lys | Glu | Met | His |
|---|---|---|---|---|---|---|---|---|---|---|---|---|---|---|---|
| 305 | | | | | 310 | | | | | 315 | | | | | 320 |

| Arg | Leu | Lys | Asp | Ala | Asp | Gly | Leu | Glu | Leu | Leu | Met | Lys | Arg | Ser | Phe |
|---|---|---|---|---|---|---|---|---|---|---|---|---|---|---|---|
| | | | | 325 | | | | | 330 | | | | | 335 | |

| Arg | Thr | Glu | Asp | Glu | Val | Asn | Val | Phe | Ser | Asp | Ile | Gly | Ala | Lys | Ile |
|---|---|---|---|---|---|---|---|---|---|---|---|---|---|---|---|
| | | | | 340 | | | | | 345 | | | | | 350 | |

| Val | Lys | Lys | Cys | Asp | Gly | Leu | Pro | Leu | Ala | Ile | Lys | Val | Ile | Gly | Gly |
|---|---|---|---|---|---|---|---|---|---|---|---|---|---|---|---|
| | | | 355 | | | | | 360 | | | | | 365 | | |

| Val | Leu | Ser | Ser | Arg | Ser | Ser | Lys | Glu | Glu | Trp | Glu | Arg | Ile | Leu | Glu |
|---|---|---|---|---|---|---|---|---|---|---|---|---|---|---|---|
| | 370 | | | | | 375 | | | | | 380 | | | | |

-continued

```
Arg Arg Trp Ser Ile Asp Gly Leu Pro Glu Glu Leu Glu Gly Ala Leu
385                 390                 395                 400

Tyr Leu Ser Tyr Ser Asp Leu His Pro Gln Leu Lys Gln Cys Phe Leu
            405                 410                 415

Trp Cys Ala Leu Leu Pro Gln Asn Phe Asp Ile His Arg Asp Val Thr
            420                 425                 430

Tyr Trp Trp Ile Ala Glu Gly Leu Val Lys Glu Thr Ser Gly Pro
        435                 440                 445

Ile His Asn Val Ala Glu Asp Tyr Tyr His Glu Leu Ile Lys Arg Asn
450                 455                 460

Leu Leu Gln Ala Arg Pro Glu Tyr Val Asp Lys Gly Ile Ser Thr Met
465                 470                 475                 480

His Asp Leu Leu Arg Gln Leu Gly Gln Phe Leu Thr Arg Asn Glu Ala
            485                 490                 495

Val Phe Met Asn Glu Lys Arg Asp Arg Cys Pro Ser Ser Ile Arg Arg
            500                 505                 510

Leu Gly Val Gly Ser Ala Val Asp Glu Ile Pro Ser Ile Glu Glu Lys
            515                 520                 525

Lys Arg Leu Arg Cys Leu Ile Val Leu Asp His Asp Thr Cys Arg Ser
530                 535                 540

Val Lys Arg Asp Ile Phe Arg Lys Leu Val His Leu Arg Ile Leu Val
545                 550                 555                 560

Leu Arg Gly Ala Gly Leu Glu Ser Ile Pro Ala Ser Val Gly Tyr Leu
            565                 570                 575

Ala Leu Leu Arg Leu Leu Asp Leu Ser Tyr Asn Glu Ile Lys Glu Leu
            580                 585                 590

Pro Gly Ser Ile Gly Asn Leu Thr Ser Leu Gly Cys Leu Ser Val Phe
            595                 600                 605

Gly Cys Thr Lys Leu Ala Ala Leu Pro Gln Ser Leu Met Arg Leu Thr
            610                 615                 620

Thr Ile Ser Phe Leu Gln Ile Gly Asn Thr Gly Leu Ala Gln Val Pro
625                 630                 635                 640

Lys Gly Ile Glu Asn Phe Arg Gln Ile Asp Asn Leu Arg Ser Phe Gln
            645                 650                 655

Asn Gly Thr Asp Gly Phe Arg Leu Asp Glu Leu Arg Ala Leu Ser Met
            660                 665                 670

Ile Arg Arg Leu Trp Val Ile Arg Leu Glu Thr Ala Thr Pro Pro Thr
            675                 680                 685

Glu Pro Val Leu Cys Asp Lys Gly Tyr Leu Lys Glu Leu Gly Leu Arg
            690                 695                 700

Cys Thr Met Gly Lys Glu Ala Asn Cys Arg Thr His Pro Asp Ser Lys
705                 710                 715                 720

Val Lys Arg Ile Glu Glu Ile Tyr Glu Ser Phe Cys Pro Pro Pro Ser
            725                 730                 735

Leu Ser Tyr Val Phe Ile Asp Gly Phe Pro Gly Arg Met Phe Pro Thr
            740                 745                 750

Trp Leu Ser Leu Glu Pro Gln Asn Lys Leu Pro Asn Leu Ala His Met
            755                 760                 765

His Phe Tyr Asp Cys Ile Ser Cys Pro Lys Leu Pro Ala Gly Gln
            770                 775                 780

Leu Pro Phe Leu Gln Val Leu His Val Lys Gly Ala Asp Ala Val Val
785                 790                 795                 800

Asn Ile Gly Ala Glu Leu Leu Gly Asn Gly Ile Pro Ser Gly Thr His
```

```
                    805                 810                 815
Thr Thr Ala Phe Pro Lys Leu Glu Leu Leu Glu Ile Leu Asp Met Tyr
            820                 825                 830

Asn Trp Gln Asn Trp Ser Leu Ser Met Asp Thr Leu Phe Glu Asn Thr
            835                 840                 845

Gln Gln Gln Phe Leu Met Pro Cys Leu Thr Arg Leu Arg Leu Ile Asn
            850                 855                 860

Cys Pro Lys Leu Arg Ala Leu Pro Asp His Leu His Arg Val Val Asn
865                 870                 875                 880

Leu Gln Arg Ile Gln Ile Glu Gly Ala Asp Ser Leu Gln Glu Val Val
                    885                 890                 895

Asn His Pro Gly Val Val Trp Leu Lys Val Lys Asn Asn Lys Ser Leu
            900                 905                 910

Arg Asn Ile Ser Asn Leu Pro Lys Leu Arg Leu Leu Ala Gln Asp
            915                 920                 925

Cys Gln Glu Leu Gln Gln Ala Glu Asn Leu Ser Ser Leu Lys Ala Leu
            930                 935                 940

Tyr Val Val Asp Cys Pro Met Glu Gln Ile Leu Trp Lys Cys Phe Pro
945                 950                 955                 960

Ile Glu Gln Gln Ser Thr Ile Val Arg Val Val Thr Thr Gly Ala His
                    965                 970                 975

Gly Gln Asp Ile Tyr Pro Leu Glu Ser Val Phe His
            980                 985

<210> SEQ ID NO 40
<211> LENGTH: 988
<212> TYPE: PRT
<213> ORGANISM: Sorghum, genotype TAM428

<400> SEQUENCE: 40

Met Gly Ser Val Leu Phe Ser Leu Ser Ser Lys Cys Leu Asp Lys Leu
1               5                   10                  15

Ala Val Leu Leu Glu Glu Glu Ile Met Met Thr Leu Ser Val Arg Lys
            20                  25                  30

Glu Ile Arg Lys Leu Ala Asp Tyr Leu Lys Tyr Phe Asp Ser Ile His
        35                  40                  45

Glu Asp Ala Asp Ala Arg Ala Met Glu His Arg Glu Met Thr Gly Ile
    50                  55                  60

Trp Trp Gly Asp Val Lys Asp Val Met Tyr Asp Val Asp Asp Ile Leu
65                  70                  75                  80

Asp Leu Leu Arg Ala His Ser Gln Lys Gln Arg Cys Cys Asp Leu Arg
                85                  90                  95

Met Leu Ser Arg Phe Ala Gln Leu Gln Phe Asp His Met Ile Ala Arg
            100                 105                 110

Lys Ile Lys Gly Val Asn Glu Arg Leu Val Glu Ile Gln Lys Asn Arg
        115                 120                 125

Asp Met Phe Leu Pro Pro Gly Leu Tyr Pro Gln Ala Gln Ala Pro Gln
    130                 135                 140

Thr Asn Gly Val Asp Ser Arg His Leu Ala Ala Ser Val Asp Glu Ile
145                 150                 155                 160

His Val Val Gly Ala Glu Ile Lys Glu Ala Thr Asp Ser Met Val Glu
                165                 170                 175

Met Ile Val Gly Tyr Gly His Gln Ser Arg Ile Ser Val Tyr Gly Ile
            180                 185                 190
```

-continued

Val Gly Met Gly Gly Ile Gly Lys Thr Thr Leu Ala Gln Lys Ile Tyr
        195                 200                 205

Asn Asp Arg Arg Ile Arg Glu Arg Phe His Gln Val Leu Ile Trp Leu
210                 215                 220

Ser Ile Ser Gln Ser Ile Ala Glu Asn Asp Leu Leu Lys Glu Ala Ile
225                 230                 235                 240

Glu Lys Ala Gly Gly Gln Cys Asn Gln His Lys Ser Lys Asp Gln Leu
                245                 250                 255

Val Gln Ile Leu Leu His Ser Ile Ser Gly Lys Ser Val Phe Leu Glu
            260                 265                 270

Leu Asp Asn Val Thr Asn Pro Asp Val Trp Ile Asp Leu Leu Arg Ser
        275                 280                 285

Pro Met Glu Arg Cys Leu Asp Ala His Val Leu Val Thr Thr Arg Ser
    290                 295                 300

Gly His Val Leu Ser Gln Met Asn Ala Val His Val Lys Glu Met His
305                 310                 315                 320

Arg Leu Lys Asp Ala Asp Gly Leu Glu Leu Leu Met Lys Arg Ser Phe
                325                 330                 335

Arg Thr Lys Asp Glu Val Asn Val Phe Ser Asp Ile Gly Ala Lys Ile
            340                 345                 350

Val Lys Lys Cys Asp Gly Leu Pro Leu Ala Ile Lys Val Ile Gly Gly
        355                 360                 365

Val Leu Ser Ser Arg Ser Ser Lys Glu Glu Trp Glu Arg Ile Leu Glu
    370                 375                 380

Arg Arg Trp Ser Ile Asp Gly Leu Pro Glu Glu Leu Glu Gly Ala Leu
385                 390                 395                 400

Tyr Leu Ser Tyr Ser Asp Leu His Pro Gln Leu Lys Gln Cys Phe Leu
                405                 410                 415

Cys Cys Ala Leu Leu Pro Gln Asn Phe Asp Ile His Arg Asp Val Thr
            420                 425                 430

Tyr Trp Trp Ile Ala Glu Gly Phe Val Lys Glu Gly Ser Gly Pro
        435                 440                 445

Ile His Asn Ile Ala Glu Asp Tyr Tyr His Glu Leu Ile Lys Arg Asn
    450                 455                 460

Leu Leu Gln Ala Arg Pro Glu Tyr Val Asp Lys Gly Val Ser Thr Met
465                 470                 475                 480

His Asp Leu Leu Arg Gln Leu Gly Gln Phe Leu Lys Arg Asn Glu Ala
                485                 490                 495

Ile Phe Met Asn Glu Lys Arg Glu Arg Cys Leu Ser Ser Ile Arg Arg
            500                 505                 510

Leu Gly Val Gly Ser Ala Val Asp Glu Ile Pro Ser Ile Glu Glu Lys
        515                 520                 525

Lys Arg Leu Arg Cys Leu Ile Val Leu His His Asp Thr Cys Arg Ser
    530                 535                 540

Val Lys Arg Asp Ile Phe Arg Lys Leu Val His Leu Arg Ile Leu Val
545                 550                 555                 560

Leu Arg Gly Ala Gly Leu Glu Ser Ile Pro Ala Ser Val Gly Tyr Leu
                565                 570                 575

Ala Leu Leu Arg Leu Leu Asp Leu Ser Tyr Asn Glu Ile Lys Glu Leu
            580                 585                 590

Pro Gly Ser Ile Gly Asn Leu Thr Ser Leu Gly Cys Leu Ser Val Phe
        595                 600                 605

Gly Cys Thr Lys Leu Ala Ala Leu Pro Thr Ser Leu Met Arg Leu Thr

```
            610                 615                 620
Thr Ile Ser Phe Leu Lys Ile Gly Asn Thr Gly Leu Ala Gln Val Pro
625                 630                 635                 640

Lys Gly Ile Glu Asn Phe Lys Gln Met Asp Asn Leu Arg Ser Phe Gln
                645                 650                 655

Asn Gly Thr Asp Gly Phe Arg Leu Asp Glu Leu Arg Ala Leu Ser Met
                660                 665                 670

Ile Arg Arg Leu Trp Val Ile Arg Leu Glu Thr Ala Ile Pro Pro Thr
                675                 680                 685

Glu Pro Ile Leu Cys Asp Lys Gly Tyr Leu Lys Glu Leu Gly Leu Arg
690                 695                 700

Cys Thr Met Gly Lys Glu Ala Asn Cys Arg Thr His Pro Asp Ser Lys
705                 710                 715                 720

Val Lys Arg Ile Glu Glu Ile Tyr Glu Ser Phe Cys Pro Pro Pro Ser
                725                 730                 735

Leu Ser Tyr Val Phe Ile Asp Gly Phe Pro Gly Arg Met Phe Pro Thr
                740                 745                 750

Trp Leu Ser Leu Glu Pro Gln Asn Lys Leu Pro Asn Leu Ala His Met
                755                 760                 765

His Phe Tyr Asp Cys Ile Ser Cys Pro Lys Leu Pro Pro Ala Gly Gln
                770                 775                 780

Leu Pro Phe Leu Gln Val Leu His Val Lys Gly Ala Asp Ala Val Val
785                 790                 795                 800

Asn Ile Gly Ala Glu Leu Leu Gly Asn Ser Ile Pro Ser Gly Thr His
                805                 810                 815

Thr Thr Ala Phe Pro Lys Leu Glu Leu Leu Glu Ile Leu Asp Met Tyr
                820                 825                 830

Asn Trp Gln Asn Trp Ser Leu Ser Met Asp Thr Leu Phe Glu Lys Thr
                835                 840                 845

Gln Gln Gln Ser Leu Met Pro Cys Leu Thr Arg Leu Arg Leu Ile Asn
850                 855                 860

Cys Pro Lys Leu Arg Ala Leu Pro Asp His Leu His Arg Val Val Asn
865                 870                 875                 880

Leu Gln Arg Ile Gln Ile Glu Gly Ala Asp Ser Leu Gln Glu Ile Val
                885                 890                 895

Asn His Pro Gly Val Val Trp Leu Lys Val Lys Asn Asn Lys Ser Leu
                900                 905                 910

Arg Asn Ile Ser Asn Leu Pro Lys Leu Arg Leu Leu Ala Gln Asp
                915                 920                 925

Cys Gln Glu Leu Gln Gln Ala Glu Asn Leu Ser Ser Leu Lys Ala Leu
                930                 935                 940

Tyr Val Val Asp Cys Pro Met Glu Gln Ile Leu Trp Lys Cys Phe Pro
945                 950                 955                 960

Ile Glu Gln Gln Ser Thr Ile Val Arg Val Thr Thr Gly Ala His
                965                 970                 975

Gly Gln Asp Ile Tyr Pro Leu Glu Ser Val Phe His
                980                 985
```

-continued

```
<210> SEQ ID NO 41
<211> LENGTH: 16
<212> TYPE: DNA
<213> ORGANISM: Sorghum variant ZZZ (truncated)

<400> SEQUENCE: 41
tgccctttga agtatt                                                    16
```

The invention claimed is:

1. An isolated polynucleotide comprising of SEQ ID NO:1 (ARG1) that confers sorghum broad resistance to fungal infection when expressed in a susceptible sorghum plant.

2. The isolated polynucleotide of claim 1, wherein said polynucleotide is within an expression cassette, the expression cassette generated using a pair of primers comprising SEQ ID Nos: 7-8.

3. A method of generating a transgenic sorghum plant with resistance to fungal infection, comprising genetically transforming a susceptible sorghum with the isolated polynucleotide of claim 1, and growing the transformed sorghum into a transgenic sorghum plant.

4. The isolated polynucleotide of claim 1, wherein the polynucleotide is expressed within a plant cell.

5. The isolated polynucleotide of claim 4, wherein the plant is a monocot.

6. The isolated polynucleotide of claim 4, wherein the plant is wheat, barley, rice, maize, sorghum, oats, rye or millet.

7. The isolated polynucleotide of claim 1, wherein the fungal infection is caused by a biotrophic fungus, a hemibiotrophic fungus, or a necrotrophic fungus.

8. The isolated polynucleotide of claim 1, wherein the fungal infection is caused by a biotrophic fungus, a hemibiotrophic fungus, or a necrotrophic fungus.

9. The isolated polynucleotide of claim 1, wherein said polynucleotide is reversely embedded in SEQ ID NO: 2 (CARG).

10. The method of claim 3, wherein the isolated polynucleotide is reversely embedded in SEQ ID NO: 2 (CARG).

* * * * *